(12) United States Patent
Mehrkhodavandi et al.

(10) Patent No.: US 10,280,185 B2
(45) Date of Patent: May 7, 2019

(54) MONONUCLEAR SALEN INDIUM CATALYSTS AND METHODS OF MANUFACTURE AND USE THEREOF

(71) Applicant: THE UNIVERSITY OF BRITISH COLUMBIA, Vancouver (CA)

(72) Inventors: Parisa Mehrkhodavandi, Vancouver (CA); Dinesh C. Aluthge, Vancouver (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 88 days.

(21) Appl. No.: 15/323,884

(22) PCT Filed: Jun. 26, 2015

(86) PCT No.: PCT/CA2015/050601
§ 371 (c)(1),
(2) Date: Apr. 10, 2017

(87) PCT Pub. No.: WO2016/000071
PCT Pub. Date: Jan. 7, 2016

(65) Prior Publication Data
US 2017/0137442 A1 May 18, 2017

Related U.S. Application Data

(60) Provisional application No. 62/021,071, filed on Jul. 4, 2014.

(51) Int. Cl.
  *C07F 5/00* (2006.01)
  *C08G 63/08* (2006.01)
  *C08G 63/84* (2006.01)
  *C08G 63/82* (2006.01)

(52) U.S. Cl.
  CPC ............... *C07F 5/003* (2013.01); *C07F 5/00* (2013.01); *C08G 63/08* (2013.01); *C08G 63/823* (2013.01); *C08G 63/84* (2013.01)

(58) Field of Classification Search
  CPC .......... C07F 5/003; C08G 63/08; C08G 63/84
  See application file for complete search history.

(56) References Cited

FOREIGN PATENT DOCUMENTS

WO   2013/134877 A1   9/2013

OTHER PUBLICATIONS

Zhong, Z., et al.; Angewandte Chemie International Edition, 2002, vol. 41, No. 23, p. 4510-4513.*
Zhang, L., et al.; Journal of the American Chemical Society, 2007, vol. 129, p. 12610-12611.*
Stanford, M.J., et al.; Chemical Society Reviews, 2010, vol. 39, p. 486-494.*
International Search Report issued in PCT/CA2015/050601 dated Sep. 2, 2015 (2 pages).
Written Opinion of the International Searching Authority issued in PCT/CA2015/050601 dated Sep. 2, 2015 (5 pages).
Aluthge, D.C. et al.; "A highly active and site selective indium catalyst for lactide polymerization"; Chem. Commun., 2013, (published online May 31, 2012) vol. 49, pp. 4295-4297 (3 pages).
Maudoux, N. et al.; "Chiral (1,2)-Diphenylethylene-Salen Complexes of Triel Metals: Coordination Patterns and Mechanistic Considerations in the Isoselective ROP of Lactide"; Chemistry—A European Journal, 2014 (published online: Apr. 7, 2014), vol. 20, pp. 6131-6147 (18 pages).
Dinesh C. Aluthge et al., "A highly active and site selective indium catalyst for lactide polymerization"; The Royal Society of Chemistry; Chem. Commun., 49; pp. 4295-4297; 2012 (3 pages).
Dinesh C. Aluthge et al., "PLA-PHB-PLA Triblock Copolymers: Synthesis by Sequential Addition and Investigation of Mechanical and Rheological Properties"; American Chemical Society; Macromolecules, 46; pp. 3695-3974; May 15, 2013 (10 pages).
Dinesh C. Aluthge et al., "Role of Aggregation in the Synthesis and Plymerization Activity of SalBinap Indium Alkoxide Complexes"; American Chemical Society; Inorganic Chemistry, 53; pp. 6828-6836; Jun. 10, 2014 (9 pages).
David A. Atwood et al., "A New Class of Aluminum Cations Based upon Tetradentate (N2O2) Chelating Liquids"; American Chemical Society; Inorganic Chemistry, 35; pp. 63-70; 1996 (8 pages).
David A. Atwood et al., "The First Structurally Characterized Salen-Indium Complexes"; The Chemical Society of Japan; Bull. Chem. Soc. Jpn., 70; pp. 2093-2100; 1997 (8 pages).
David A. Atwood et al., "Group 13 Compounds Incorporation Salen Ligands"; American Chemical Society; Chemical Reviews, vol. 101, No. 1; pp. 37-52; Dec. 20, 2010 (16 pages).
Clare Bakewell et al., "Yttrium Phosphasalen Initiators for rac-Lactide Polymerization: Excellent Rates and High Iso-Selectives"; Journal of the American Chemical Society, 134; pp. 20577-20580; Dec. 11, 2012 (4 pages).

(Continued)

*Primary Examiner* — Robert S Jones
(74) *Attorney, Agent, or Firm* — Ferguson Braswell Fraser Kubasta PC

(57) ABSTRACT

The present application provides salen indium catalysts of the following general structure wherein R is a coordinating alkoxide comprising at least one coordinating atom that forms a dative bond with In. The mononuclear salen indium catalysts are particularly useful in catalyzing ring-opening polymerizations of cyclic ester monomers, such as lactides. Also provided herein are methods of using the mononuclear salen indium complexes to catalyze polymerization of cyclic ester monomers. Of particular interest is the successful polymerization of lactides using the mononuclear salen indium catalysts to produce poly(lactic acid) having high isotacticity.

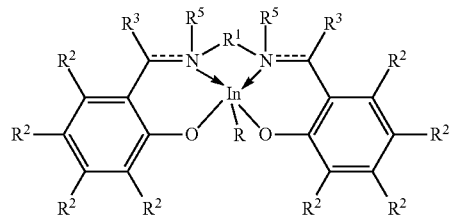

47 Claims, 13 Drawing Sheets

(56) References Cited

OTHER PUBLICATIONS

Clare Bakewell et al., "Metal-Size Influence in Iso-Selective Lactide Polymerization"; Angewandte Chemie International Edition, 53; pp. 9226-9230; 2014 (5 pages).

Matthew P. Blake et al., "Sulfonamide, Phenolate, and Directing Ligand-Free Indium Initiators for the Ring-Opening Polymerization of rac-Lactide"; American Chemical Society; Organometallics, vol. 30, No. 5; pp. 1202-1214; Feb. 18, 2011 (13 pages).

F.A. Bovey et al., "NMR of Polymers"; Academic Press; pp. 133-143; San Diego, USA; 1996 (11 pages).

Jean-Charles Buffet et al., "Initiators for the stereoselective ring-opening polymerization of meso-lactide"; The Royal Society of Chemistry; Polymer Chemistry, 2; pp. 2758-2763; Aug. 18, 2011 (6 pages).

Chen-Xin Cai et al., "Stereoselective ring-opening polymerization of racemic lactide using alkoxy-amino-bis(phenolate) group 3 metal complexes"; The Royal Society of Chemistry; Chem. Commun.; pp. 330-331; Jan. 8, 2004 (2 pages).

Laetitia Canali et al., "Utilisation of homogeneous and supported chiral metal(salen) complexes in asymmetric catalysis"; Chem. Soc. Rev., 28; pp. 85-93; Published Jan. 1, 1999 (9 pages).

Bradley M. Chamberlain et al., "Polymerization of Lactide with Zinc and Magnesium B-Diiminate Complexes: Stereocontrol and Mechanism"; American Chemical Society; J. Am. Chem. Soc., vol. 123, No. 14; pp. 3229-3238; Published Mar. 16, 2001 (10 pages).

Hang-Chang Chen et al., "Diffusion of Crown Ethers in Alcohols"; American Chemical Society; The Journal of Physical Chemistry, vol. 88, No. 21; pp. 5518-5121; 1984 (4 pages).

Malcolm H. Chisholm et al., "Concerning the relative importance of enantiomorphic site vs. chain end control in the stereoselective polymerization of lactides: reactions of (R,R-salen)- and (S,S-salen)-aluminium alkoxides LAIOCH2R , complexes (R=CH3 and S-CHMeCl)"; The Royal Society of Chemistry; Chem. Commun.; pp. 127-129; Published Nov. 25, 2004 (3 pages).

Claire T. Cohen et al., "Copolymerization of cyclohexene oxide and carbon dioxide using (salen)Co(III) complexes: synthesis and characterization of syndiotactic poly(cyclohexene carbonate)"; The Royal Society of Chemistry; Dalton Transactions; pp. 237-249; Published Nov. 24, 2005 (13 pages).

J. Coudane et al., "More about the Stereodependence of DD and LL Pair Linkages during the Ring-Opening Polymerization of Racemic Lactide"; J. Polym. Sci., Part A: Polym. Chem.; pp. 1651-1658; 1997 (8 pages).

Samuel Dagorne et al., "Gallium and indium complexes for ring-opening polymerization of cyclic ethers, esters and carbonates"; Coordination Chemistry Reviews 257; pp. 1869-1886; 2013 (18 pages).

Odile Dechy-Cabaret et al., "Controlled Ring-Opening Polymerization of Lactide and Glycolide"; American Chemical Society; Chemical Reviews, vol. 104, No. 12; pp. 6147-6176; Published Oct. 5, 2004 (30 pages).

Pieter Jelle Dijkstra et al., "Single site catalysts for stereoselective ring-opening polymerization of lactides"; The Royal Society of Chemistry; Polymer Chemistry, 2; pp. 520-527; Published Sep. 8, 2010 (8 pages).

Amy F. Douglas et al., "A Highly Active Chiral Indium Catalyst for Living Lactide Polymerization"; Angewandte Chemie International Edition, 47; pp. 2290-2293; 2008 (4 pages).

Jian Fang et al., "Theoretical Investigation of Lactide Ring-Opening Polymerization Induced by a Dinuclear Indium Catalyst"; American Chemical Society; Organometallics, 32; pp. 6950-6956; Published Nov. 14, 2013 (7 pages).

Kazuki Fukushima et al., "Stereocomplexed polylactides (Neo-PLA) as high-performance bio-based polymers: their formation, properties, and application"; Society of Chemical Industry; Polymer International, 55; pp. 626-642; Apr. 6, 2006 (17 pages).

Anna M. Goldys et al., "Organocatalytic Ring-Opening Polymerization of Cyclic Esters Mediated by Highly Active Bifunctional Iminophosphorane Catalysts"; American Chemical Society; Macromolecules, 47; pp. 1277-1284; Published Feb. 6, 2014 (8 pages).

Bhuvanesh Gupta et al., "Poly(lactic acid) Fiber: an Overview"; Progress in Polymer Science; (2007) (84 pages).

Pimpa Hormnirun et al., "Study of ligand substituent effects on the rate and stereoselectivity of lactide polymerization using aluminum salen-type initiators"; PNAS, vol. 103, No. 42; pp. 15343-15348; Oct. 17, 2006 (6 pages).

Eric N. Jacobsen et al., "Electronic Tunic of Asymmetric Catalysts"; American Chemical Society; J. Am. Chem. Soc, 113; pp. 6703-6704; May 22, 1991 (2 pages).

Jay F. Larrow et al., "(R,R)-N,N'-Bis(3,5-DI-tert-Butylsalicylidene)-1,2-Cyclohexanediamino Manganese (III) Chloride, A Highly Enantioselective Epdxidation Catalyst"; Organic Synthesis, Coll. vol. 10, p. 96 (2004); vol. 75, p. 1-7 (1998) (7 pages).

Tryg R. Jensen et al., "Stereoelective polymerization of D,L-lactide using N-heterocyclic carbene based compounds"; The Royal Society of Chemistry; Chem. Commun.; pp. 2504-2505; Published Sep. 8, 2004 (2 pages).

Hans R. Kricheldorf et al., "Polylactones: 23. Polymerization of racemic and meso D,L-lactide with various organotin Catalysts-stereochemical aspects"; Polymer, vol. 33, No. 13; pp. 2817-2824;1992 (8 pages).

Alceo Macchioni et al., "Determining accurate molecular sizes in solution through NMR diffusion spectroscopy"; The Royal Society of Chemistry; Chem. Soc. Rev., 37; pp. 479-489; Published Oct. 11, 2007 (11 pages).

Michael. S. Hill et al., "Synthesis and Reactivity of Five-Coordinate Indium Halides and Alkyls"; Main Group Chemistry, vol. 2; No. 3, pp. 191-202; 1998 (13 pages).

Nicolas Maudoux et al., "Chiral (1,2)-Diphenylethylene-Salen Complexes of Triel Metals: Coordination Patterns and Mechanistic Considerations in the Isoselective ROP of Lactide"; Chem. Eur. J., 20; pp. 6131-6147; 2014 (17 pages).

Jung Kwon Oh, "Polylactide (PLA)-based amphiphilic block copolymers: synthesis, self-assembly, and biomedical applications"; The Royal Society of Chemistry; Soft Matter, 7; pp. 5096-5108; Published Mar. 24, 2011 (13 pages).

Kimberly M. Osten et al., "Effects of ligand tuning on dinuclear indium catalysts for lactide polymerization"; The Royal Society of Chemistry; Dalton Transactions, 41; pp. 8123-8134; Published Mar. 8, 2012 (13 pages).

Kimberly M. Osten et al., "Probing the Role of Secondary versus Tertiary Amine Donor Ligands for Indium Catalysts in Lactide Polymerization"; American Chemical Society; Inorganic Chemistry, 53; pp. 9897-9906; 2014 (10 pages).

K. M. Osten et al., "The effect of steric changes on the isoselectivity of dinuclear indium catalysts for lactide polymerization"; The Royal Society of Chemistry; Dalton Transactions, 44; pp. 6126-6139; Published Mar. 2, 2015 (14 pages).

Tina M. Ovitt et al., "Stereochemistry of Lactide Polymerization with Chiral Catalysts: New Opportunities for Stereocontrol Using Polymer Exchange Mechanisms"; American Chemical Society; J. Am. Chem. Soc., vol. 124, No. 7; pp. 1316-1326; 2002 (11 pages).

Ilja Peckermann et al., "Indium Complexes Supported by 1,omega-Dithiaalkanediyl-Bridged Bis(phenolato) Ligands: Synthesis, Structure, and Controlled Ring-Opening Polymerization of L-Lactide"; American Chemical Society; Inorganic Chemistry, 48; pp. 5526-5534; Published May 8, 2009 (9 pages).

Agostino Pietrangelo et al.,"Mechanistic Study of the Stereoselective Polymerization of D,L-Lactide Using Indium(III) Halides"; American Chemical Society; J. Am. Chem. Soc., vol. 132, No. 33; pp. 11649-11657; 2010 (9 pages).

Valentyn Rudzevich et al., "Carbamoylmethylphosphinoxide Derivatives Based on the Triphenylmethane Skeleton. Synthesis and Extraction Properties"; American Chemical Society; Journal of Organic Chemistry , vol. 70, No. 15; pp. 6027-6033; Published Jun. 25, 2005 (7 pages).

M. Schlosser, "Generation of Organometallic Reagents and Intermediates"; Organometallics in Synthesis: A Manual, 2nd ed.; p. 262; Wiley Publishing; 2002 (1 page).

Matthew J. Stanford et al., "Stereocontrolled ring-opening polymerisation of lactide"; The Royal Society of Chemistry; Chemical Society Reviews, 39; pp. 486-494; Published Oct. 1, 2009 (9 pages).

(56) References Cited

OTHER PUBLICATIONS

"Dispersity in polymer science (IUPAC Recommendation 2009)"; International Union of Pure and Applied Chemistry; Society of Chemical Industry; Polymer International, vol. 59; pp. 23-24; 2010 (2 pages).

Avinash N. Thadani et al., "Expedient, High-Yielding Synthesis of Silyl-Substituted Salen Ligands"; American Chemical Society; Organic Letters, vol. 9, No. 20; pp. 3873-3876; Published Sep. 1, 2007 (4 pages).

Khalid A. M. Thakur et al., "An alternative interpretation of the HETCOR NMR spectra of poly(lactide)"; Chem. Commun.; pp. 1913-1914; Published Jan. 1, 1998 (2 pages).

Christophe M. Thomas, "Stereocontrolled ring-opening polymerization of cyclic esters: synthesis of new polyester microstructures"; The Royal Society of Chemistry; Chem. Soc. Rev., 39; pp. 165-173; Published Sep. 28, 2009 (9 pages).

Cuiling Xu et al., "Highly controlled immortal polymerization of b-butyrolactone by a dinuclear indium catalyst"; The Royal Society of Chemistry; Chem. Commun., 48; pp. 6806-6808; 2012 (3 pages).

Xiaoquan Yao et al., "Substituted salen-Ru(II) complexes as catalysts in the asymmetric cyclopropanation of styrene by ethyl diazoacetate: the influence of substituents and achiral additives on activity and enantioselectivity"; Tetrahedron: Asymmetry 12; pp. 197-204; 2001 (8 pages).

Jae Woong Yoon et al., "(1R,2R)-(-)-N,N'-Bis(3,5-di-tert-butylsalicylidene )-1,2-cyclohexanediamine: a Salen Ligand of Jacobsen's Catalyst"; Acta Crystallographica Section C; pp. 1685-1687; 1997 (3 pages).

Insun Yu et al., "Mechanism of Living Lactide Polymerization by Dinuclear Indium Catalysts and Its Impact on Isoselectivity"; American Chemical Society; Journal of the American Chemical Society, 134; pp. 12758-12773; Published Jul. 5, 2012 (16 pages).

Haobing Wang et al., "Stereoselectivity Switch between Zinc and Magnesium Initiators in the Polymerization of rac-Lactide: Different Coordination Chemistry, Different Stereocontrol Mechanisms"; American Chemical Society; Macromolecules, 47; pp. 7750-7764; Published Nov. 3, 2014 (15 pages).

Mark T. Zell et al., "Unambiguous Determination of the 13C and 1H NMR Stereosequence Assignments of Polylactide Using High-Resolution Solution NMR Spectroscopy"; American Chemical Society; Macromolecules, vol. 35, No. 20; pp. 7700-7707; Published Aug. 24, 2002 (8 pages).

* cited by examiner

MONONUCLEAR SALEN INDIUM CATALYSTS AND METHODS OF MANUFACTURE AND USE THEREOF

FIELD OF THE INVENTION

The present invention pertains to mononuclear salen indium complexes. More particularly, the present invention pertains to mononuclear salen indium complexes that are useful as catalysts, for example, in ring opening polymerizations, such as stereoselective polymerization of lactide to give isotactically enriched polylactic acid.

BACKGROUND

Poly(lactic acid), or poly(lactide), commonly referred to as PLA, is a commercially important biodegradable polyester that has many potential medical, agricultural, and packaging applications because of its biocompatibility and biodegradability. Concern about the environmental impact and increasing cost of petroleum based polymers has renewed interest in polymers derived from natural products, such as PLA.

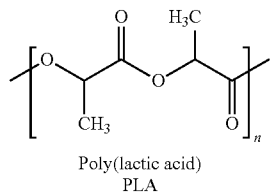

Poly(lactic acid)
PLA

PLA is produced by the ring opening polymerization (ROP) of the six-membered cyclic ester lactide (Dechy-Cabaret, O.; Martin-Vaca, B.; Bourissou, D. Chem. Rev. 2004, 104, 6147-6176; Gupta, B.; Revagade, N.; Hilborn, J. Prog. Poly. Sci. 2007, 32, 455-482; Oh, J. K. Soft Matter 2011, 7, 5096-5108). Lactic acid (LA) is produced in chiral and racemic forms by fermentation of corn and other agricultural products. Lactides are the cyclic diesters of lactic acid and are prepared by the dehydration of lactic acid. When lactide is prepared from racemic lactic acid, the three isomers that result are R-lactide (D-lactide), S-lactide (L-lactide) and meso-lactide; rac-lactide is a 50:50 mixture of R-lactide and S-lactide.

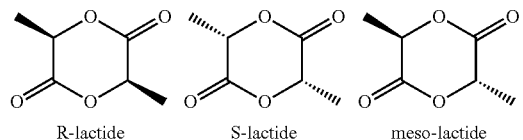

R-lactide          S-lactide          meso-lactide

The stereochemistry of PLAs determines, at least in part, their mechanical, physical and thermal properties, as well as their rates of degradation. The bulk properties of PLAs, especially their melting points, are intrinsically linked to the polymer microstructure. Poly(R-lactic acid) and poly(S-lactic acid) are both crystalline polymers with melting points of about 180° C., while atactic PLA produced from the polymerization of RS-lactide is an amorphous polymer with no melting point. The ability to control the polymer tacticity can have an enormous impact on the properties and applications of the final polymer (Dijkstra, P. J.; Du, H. Z.; Feijen, J. Polym. Chem. 2011, 2, 520-527; Buffet, J. C.; Okuda, J. Polym. Chem. 2011, 2, 2758-2763; Thomas, C. M. Chem. Soc. Rev. 2010, 39, 165-173; Stanford, M. J.; Dove, A. P. Chem. Soc. Rev. 2010, 39, 486-494).

Isotactic PLA derived solely from L-lactide ($P_m$=0.8, where $P_m$ is the probability of finding a pair of adjacent structural units in a polymer that have the same stereochemistry) has a melting point of 178° C., while all heterotactic polymers generated to date through chain end control are amorphous (Buffet, J. C.; Okuda, J. Polym. Chem. 2011, 2, 2758-2763; Fukushima, K; Kimura, Y. Polym. Int. 2006, 55, 626-642). Stereoblock polymers, generated from rac-LA using selective chiral aluminum salen complexes, can have melting points of well over 200° C., displaying the power of stereoselective ROP catalysts (Fukushima, K.; Kimura, Y. Polym. Int. 2006, 55, 626-642).

Chiral catalysts can be used to selectively polymerize one stereoisomer in a racemic mixture of lactides to produce isotactically enriched PLA. For example, metal-salen complexes have been used in asymmetric catalysis, including stereoselective polymerization of rac-lactide (Canali, L.; Sherrington, D. C. Chem. Soc. Rev. 1999, 28, 85; Dechy-Cabaret, O.; Martin-Vaca, B.; Bourissou, D. Chem. Rev. 2004, 104, 6147).

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the application is to provide a mononuclear salen indium catalyst and methods of manufacture and use thereof. These catalysts are useful in catalyzing ring-opening polymerizations, such as the polymerization of lactide. It has been found that indium complexes bearing a salen ligand demonstrate a combination of site-selectivity and activity for the ring opening polymerization of lactide.

In accordance with one aspect, there is provided a complex having a structure of formula (Ia):

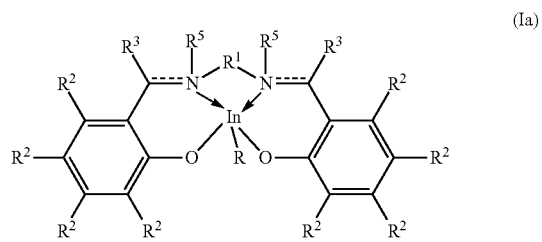

wherein
the dashed line represents an optional double bond;
$R^1$ is an optionally substituted $C_{2-5}$ alkylene,

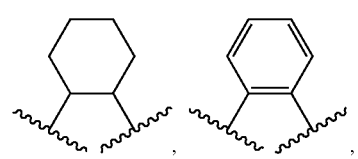

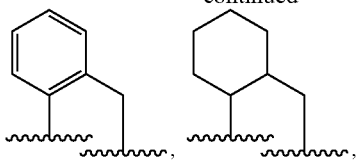,

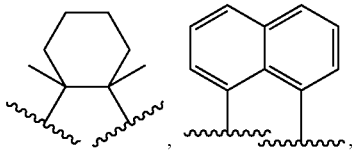,

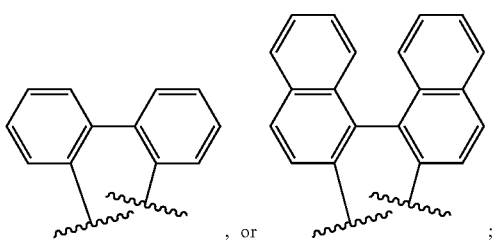, or ;

each $R^2$ is independently hydrogen, halogen, optionally substituted linear or branched $C_{1-18}$ alkyl (e.g., $C_{1-10}$ alkyl), optionally substituted cyclic $C_{3-18}$ alkyl (e.g., cyclic $C_{3-12}$ alkyl), or optionally substituted phenyl or SiR', where R' is alkyl or aryl;

each $R^3$ is hydrogen or optionally substituted linear or branched $C_{1-18}$ alkyl (e.g., $C_{1-10}$ alkyl), or optionally substituted cyclic $C_{3-18}$ alkyl (e.g., cyclic $C_{3-12}$ alkyl);

R is a coordinating alkoxide of formula $OR^4$, wherein $R^4$ comprises at least one coordinating atom that forms a dative bond with In; and each $R^5$ is independently hydrogen, optionally substituted linear or branched $C_{1-18}$ alkyl (e.g., $C_{1-10}$ alkyl), optionally substituted cyclic $C_{3-18}$ alkyl (e.g., cyclic $C_{3-12}$ alkyl) or, when there is a C—N double bond, absent.

In accordance with one embodiment, the complex has a structure of formula (Ib):

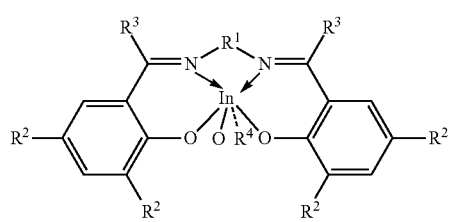

(Ib)

wherein, the dashed line represents a dative bond between a coordinating atom in $R^4$ and In;

$R^4$ is bonded to O, and is an optionally substituted aminoalkyl or aminoaryl, optionally substituted thioalkyl or thioaryl, optionally substituted phosphinoalkyl or phosphinoaryl, or optionally substituted ether radical, which forms a dative bond with In via the respective heteroatom; or, $R^4$ is bonded to O, and has the structure of formula (Ic)

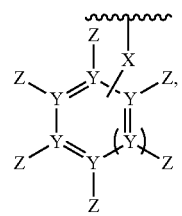

(Ic)

wherein n is 0 to 8;

each Z is independently absent, at least one lone pair of electrons, or a hydrogen, halogen, hydroxide, optionally substituted linear or branched $C_{1-18}$ alkyl (e.g., $C_{1-10}$ alkyl), optionally substituted cyclic $C_{3-18}$ alkyl (e.g., cyclic $C_{3-12}$ alkyl), optionally substituted phenyl or SiR', where R' is alkyl or aryl, optionally substituted heteroaryl, optionally substituted $C_{1-8}$ amino, $C_{1-18}$ alkyl alkoxide; or, any two Z, together with the atoms to which they are attached, combine to form a cycle or heterocycle;

X is absent, optionally substituted linear or branched $C_{1-8}$ alkyl, optionally substituted cyclic $C_{3-8}$ alkyl, optionally substituted aryl, or optionally substituted heteroaryl; and each Y is independently C or a coordinating atom, wherein at least two Y are C, and at least one Y coordinates to In.

In accordance with one embodiment, $R^1$ is

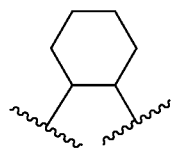.

In accordance with one embodiment, $R^1$ is chiral. In accordance with an alternative embodiment, the stereochemistry of $R^1$ is (R,R). Alternatively, the $R^1$ is racemic.

In accordance with another embodiment, the complex comprises a ligand selected from the following structures:

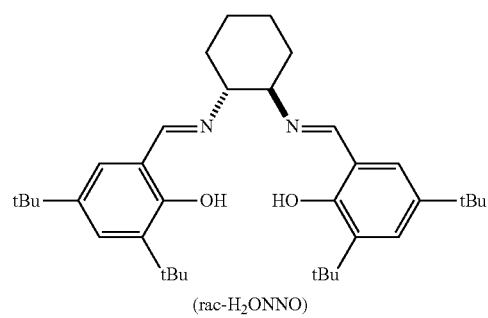

(rac-$H_2$ONNO)

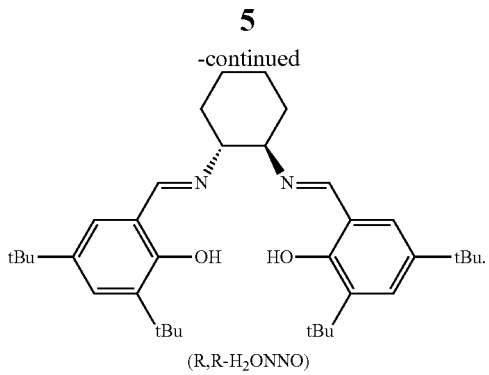

(R,R-H₂ONNO)

In accordance with another aspect, there is provided a method of ring-opening polymerization comprising polymerizing a cyclic ester monomer, or combination of two or more cyclic ester monomers, in the presence of a complex of formula Ia, under conditions suitable for ring-opening polymerization.

In accordance with another aspect, there is provided a method of making poly(lactic acid) comprising polymerizing lactide in the presence of a complex of formula Ia.

In accordance with another aspect, there is provided a method for preparing a block copolymer, comprising:

(a) polymerizing a first cyclic ester monomer using a first complex of formula Ia under conditions suitable for ring-opening polymerization of the first cyclic ester monomer to form a first polymer block of the block copolymer; and (b) polymerizing a second cyclic ester monomer, different from the first cyclic ester monomer, using a second complex of formula Ia, under conditions suitable for ring-opening polymerization of the second cyclic ester monomer to form a second polymer block of the block copolymer.

In accordance with another aspect, there is provided a method of making a complex having the structure of formula Ia comprising:

a) reacting a compound of formula (IIa) with a strong base to give a diphenoxide

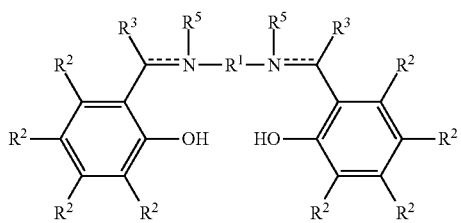

b) complexing the diphenoxide of step a) with an indium salt $InX_3$ to give an indium complex of formula (IIb),

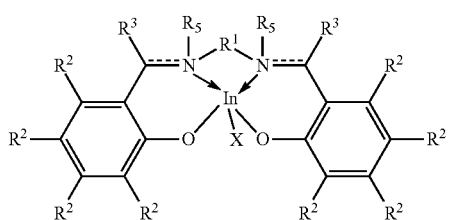

wherein X is an anion, and c) reacting the indium complex of formula (IIb) with a salt of $R^4OM$, wherein M is a metal cation, such as $Li^+$, $Na^+$ or $K^+$, or $NR^6_4{}^+$, wherein $R^6$ is an alkyl.

In one embodiment, the indium salt is $InX_3$, wherein each X is independently an acceptable anion, such as, but not limited to, a halide (e.g., $Cl^-$), triflate, or an alkoxide (e.g., ethoxide). In accordance with one embodiment, the indium salt is an indium halide. In one another embodiment, the indium salt is indium triflate. In one embodiment, the indium salt is indium chloride.

In accordance with another aspect, there is provided a method of producing a complex having the structure of formula (Ia):

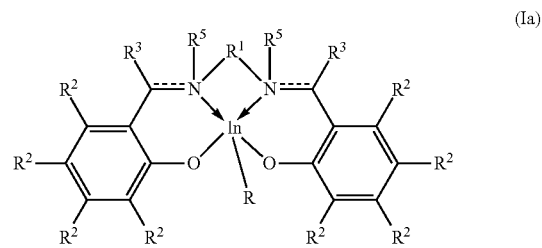

wherein the dashed line represents an optional double bond;

$R^1$ is an optionally substituted $C_{2-5}$ alkylene,

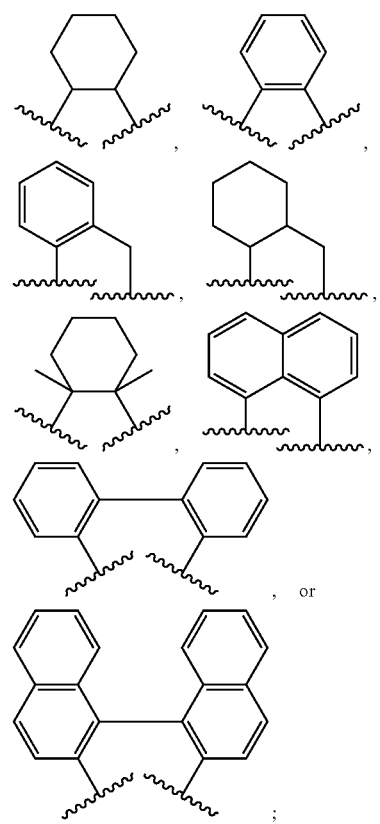

each $R^2$ is independently hydrogen, halogen, optionally substituted linear or branched $C_{1-18}$ alkyl (e.g., $C_{1-10}$ alkyl), optionally substituted cyclic $C_{3-18}$ alkyl (e.g., cyclic $C_{3-12}$ alkyl), optionally substituted phenyl or SiR', where R' is alkyl or aryl;

each $R^3$ is hydrogen or optionally substituted linear or branched $C_{1-18}$ alkyl (e.g., $C_{1-10}$ alkyl), optionally substituted cyclic $C_{3-18}$ alkyl (e.g., cyclic $C_{3-12}$ alkyl);

R is a coordinating alkoxide of formula $OR^4$, wherein $R^4$ comprises at least one coordinating atom that forms a dative bond with In; and each $R^5$ is independently hydrogen, optionally substituted linear or branched $C_{1-18}$ alkyl (e.g., $C_{1-10}$ alkyl), optionally substituted cyclic $C_{3-18}$ alkyl (e.g., cyclic $C_{3-12}$ alkyl) or, when there is a C—N double bond, absent, comprising:

a) reacting a compound of formula (IIa)

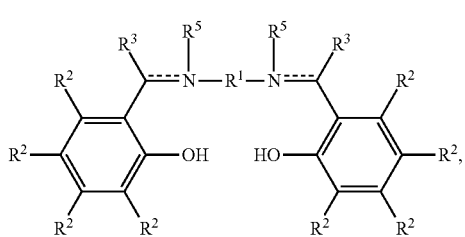

wherein $R^2$, $R^3$, and $R^5$ are as defined above,
with an indium salt $InX_3$; and
a salt of $R^4OM$ wherein M is a metal cation, such as $Li^+$, $Na^+$ or $K^+$, or $NR^6_4{}^+$, wherein $R^6$ is an alkyl, and $R^4$ is as defined above.

BRIEF DESCRIPTION OF THE FIGURES AND TABLES

For a better understanding of the present invention, as well as other aspects and further features thereof, reference is made to the following description which is to be used in conjunction with the accompanying drawings and tables, where:

Figure 6:
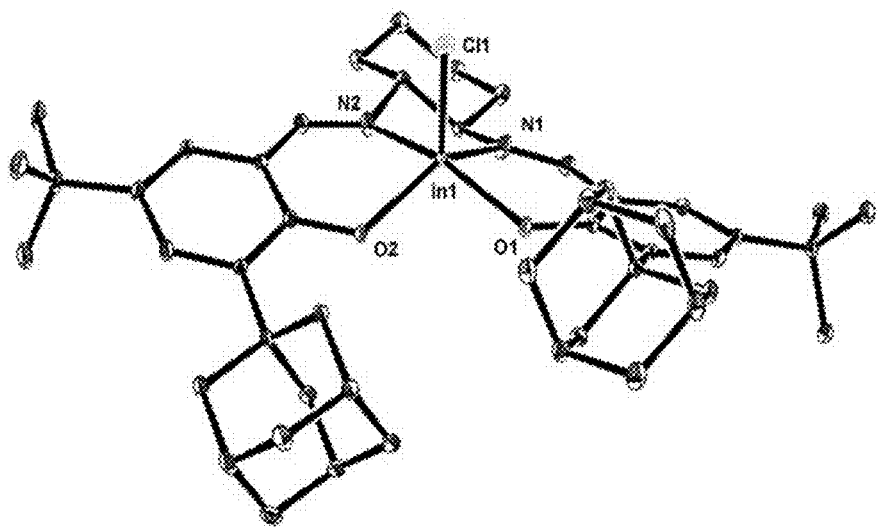
Figure 7:
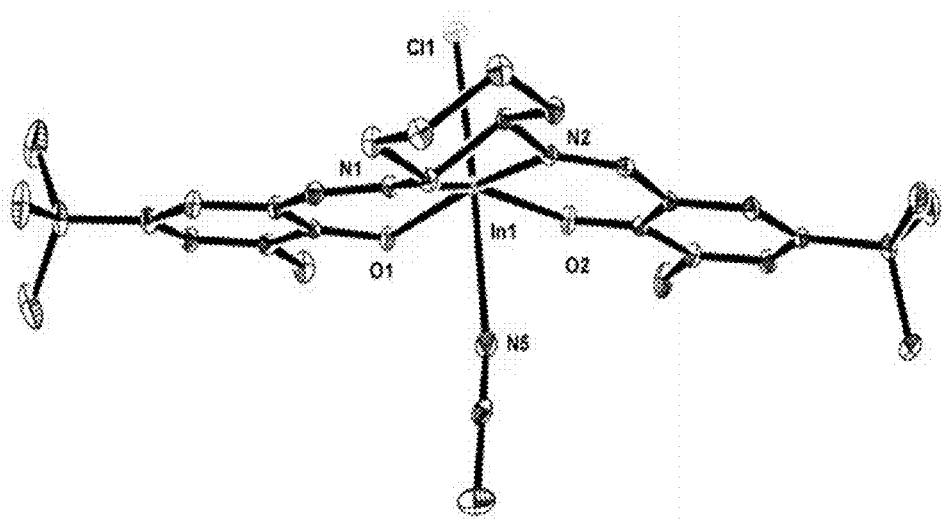
Figure 8:
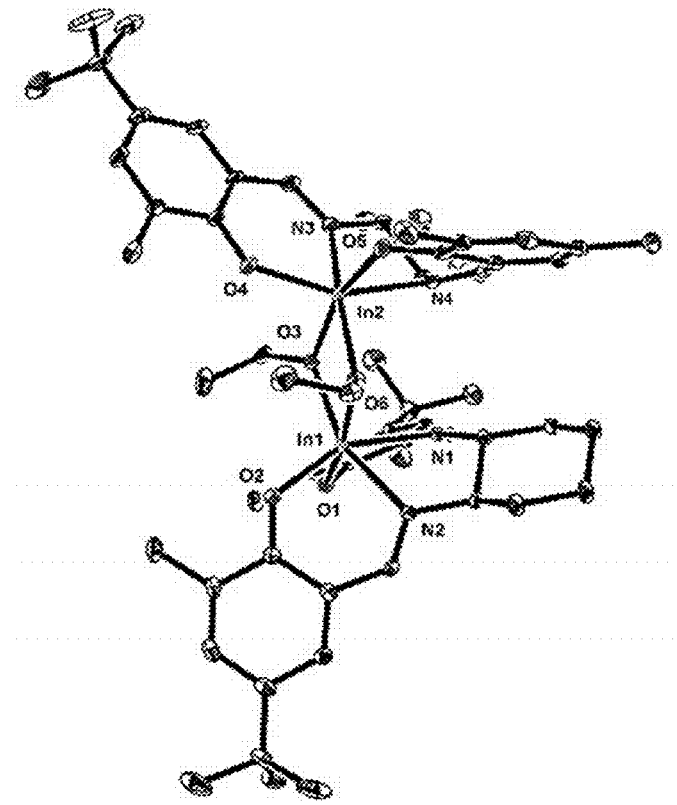
Figure 9:
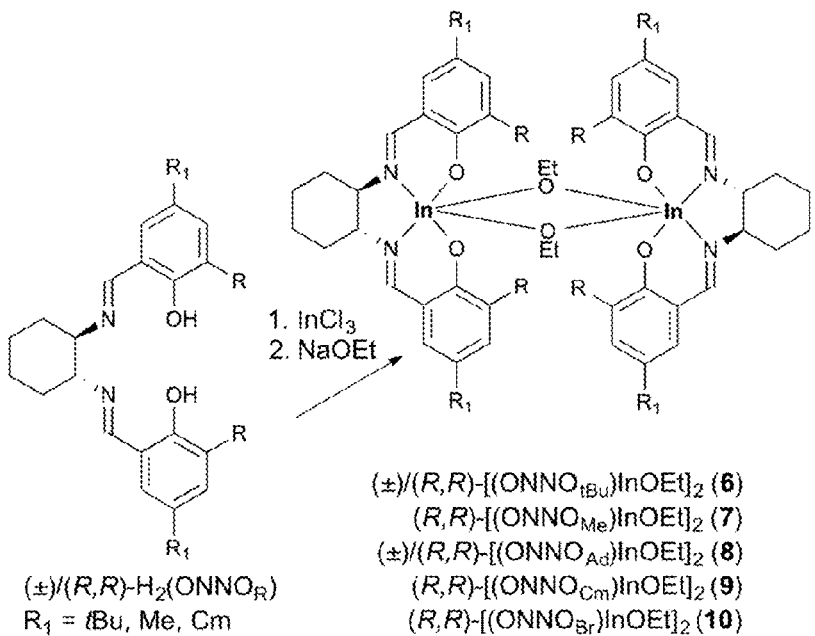
Figure 10:
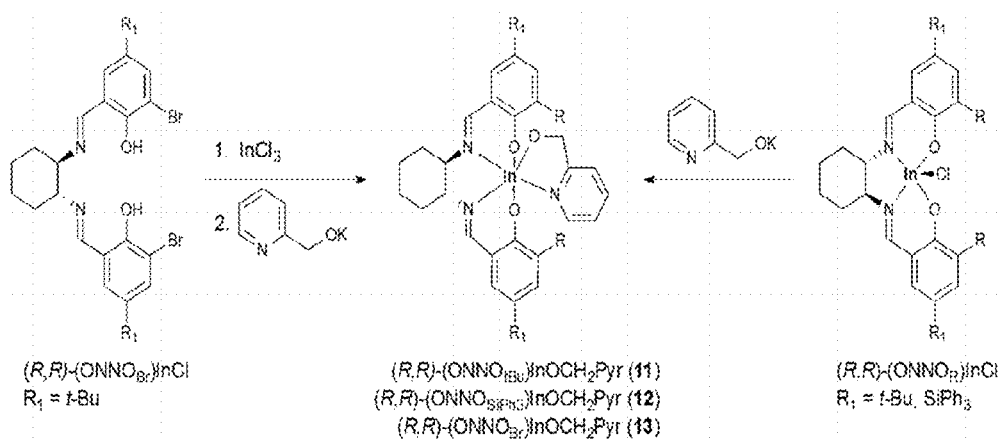
Figure 11:
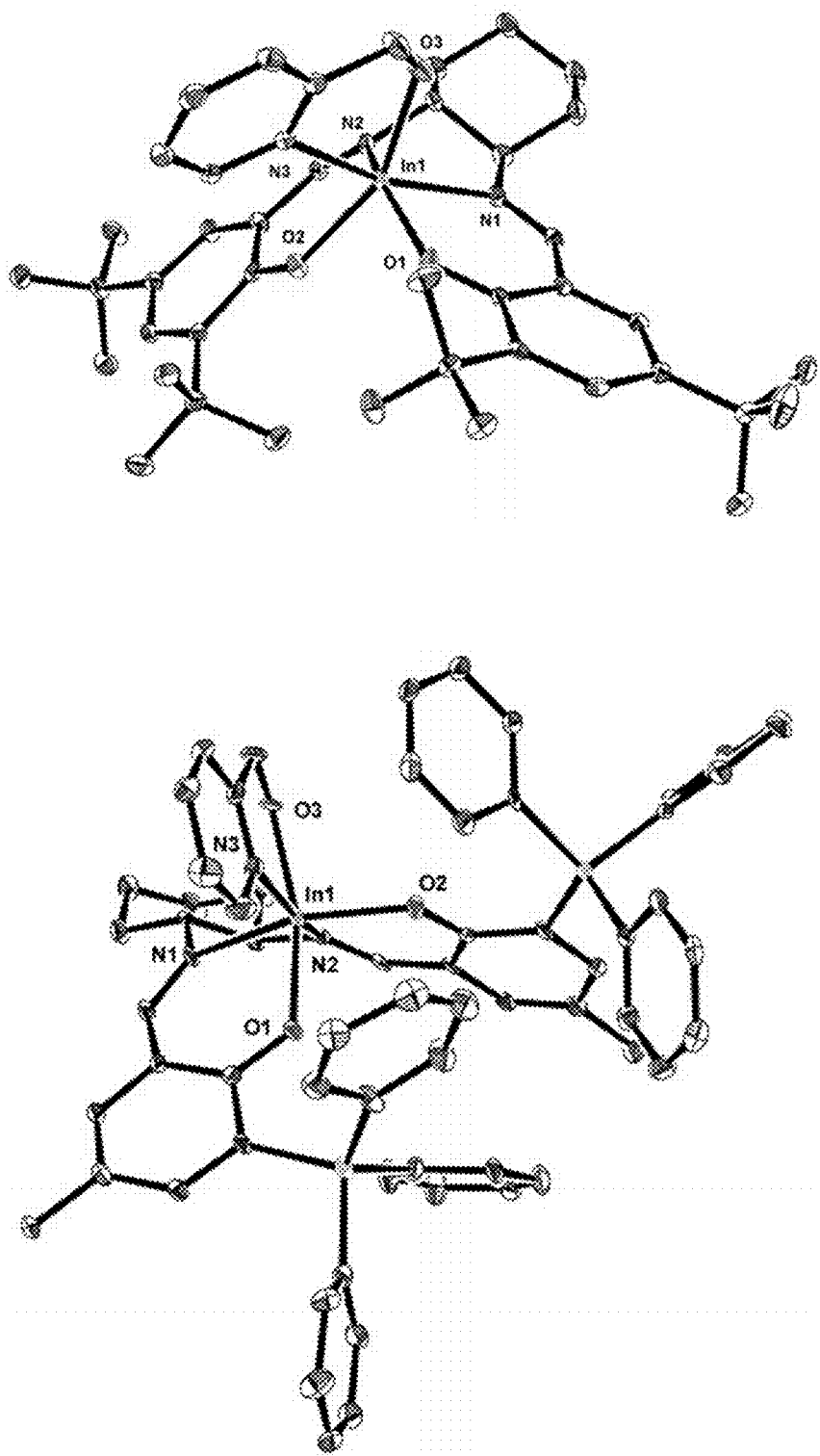
Figure 12:
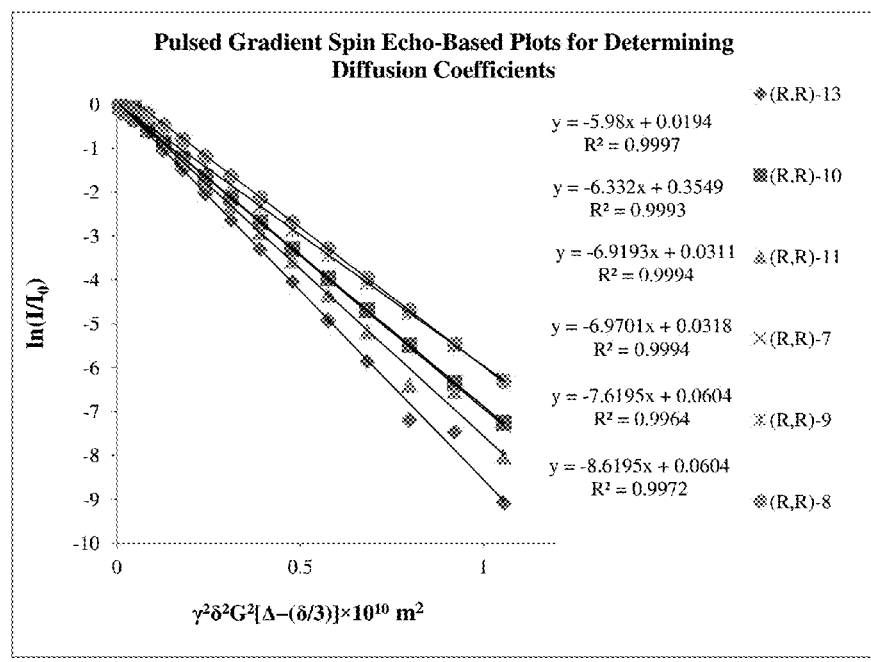
Figure 13:
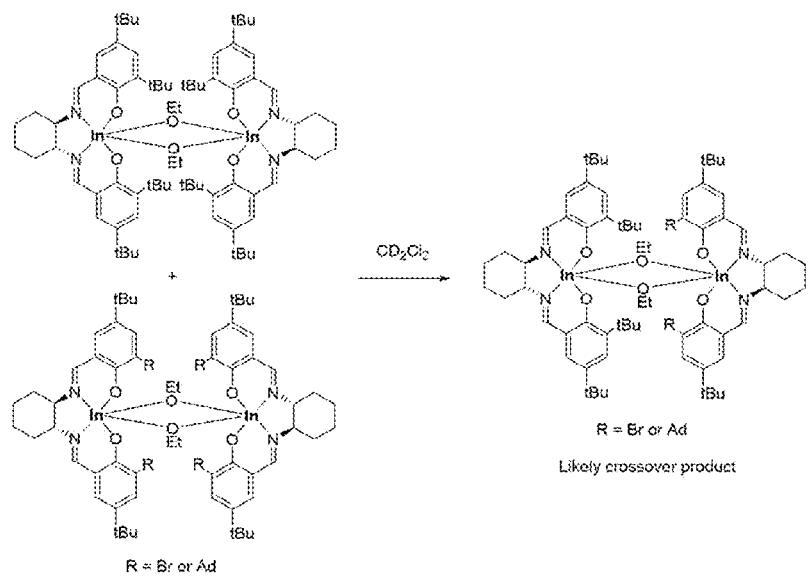
Figure 14:
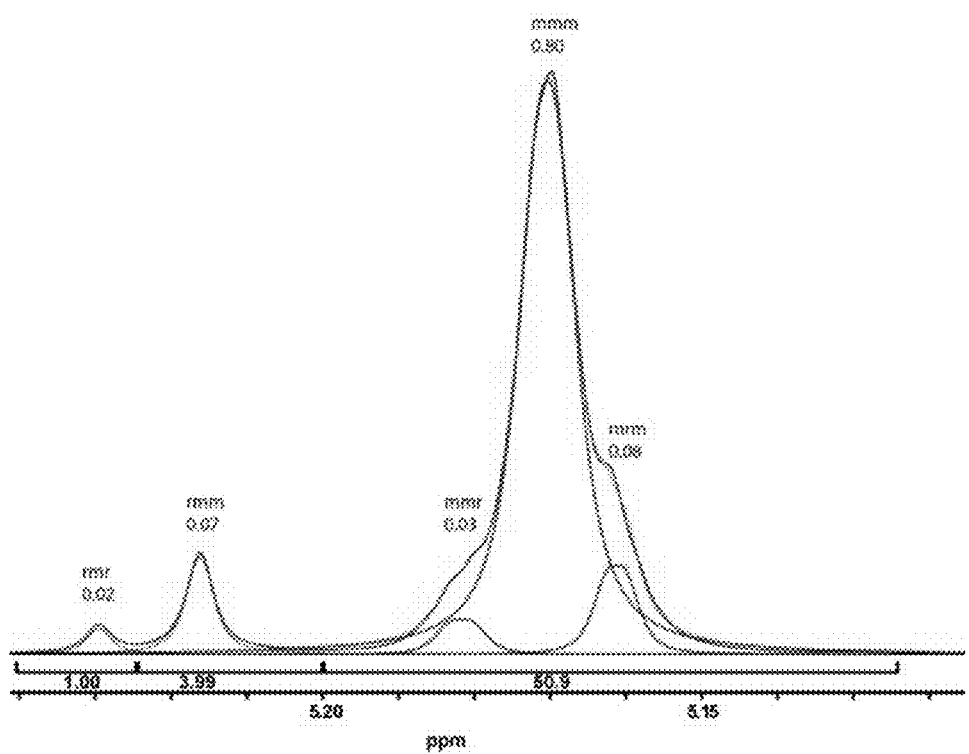
Figure 15:
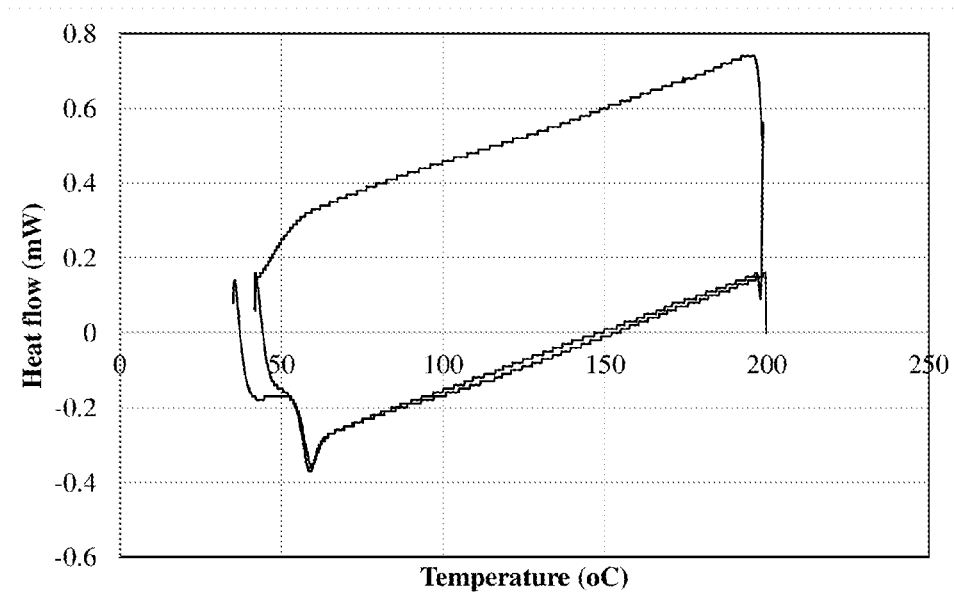
Figure 16:
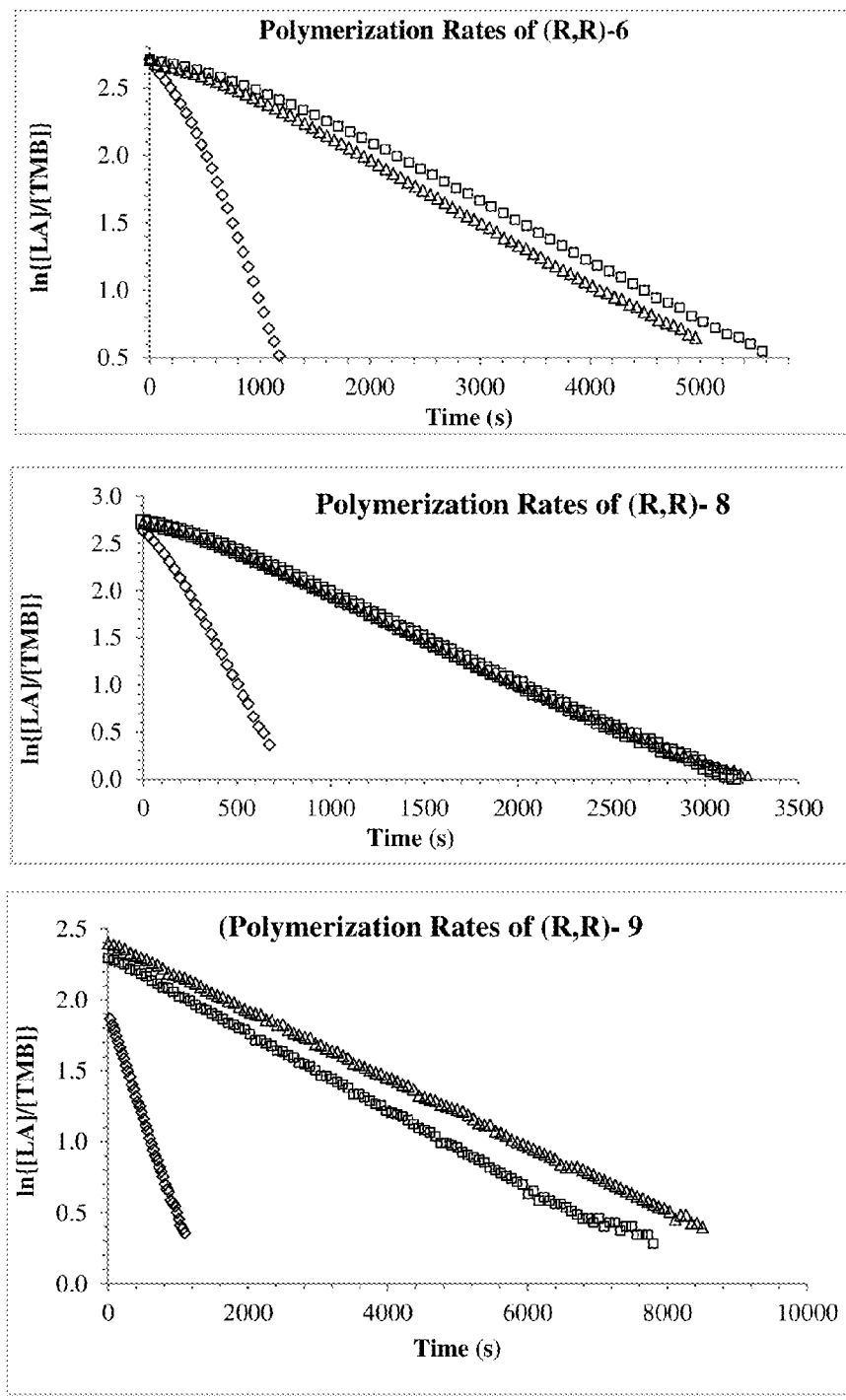
Figure 17:
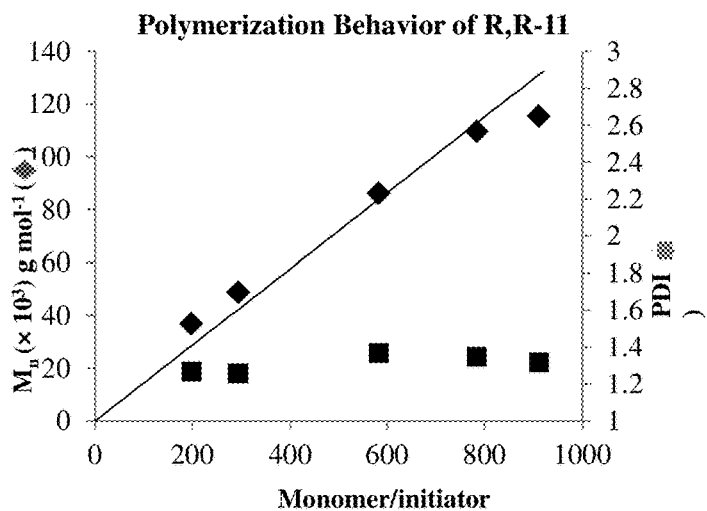
Figure 18:
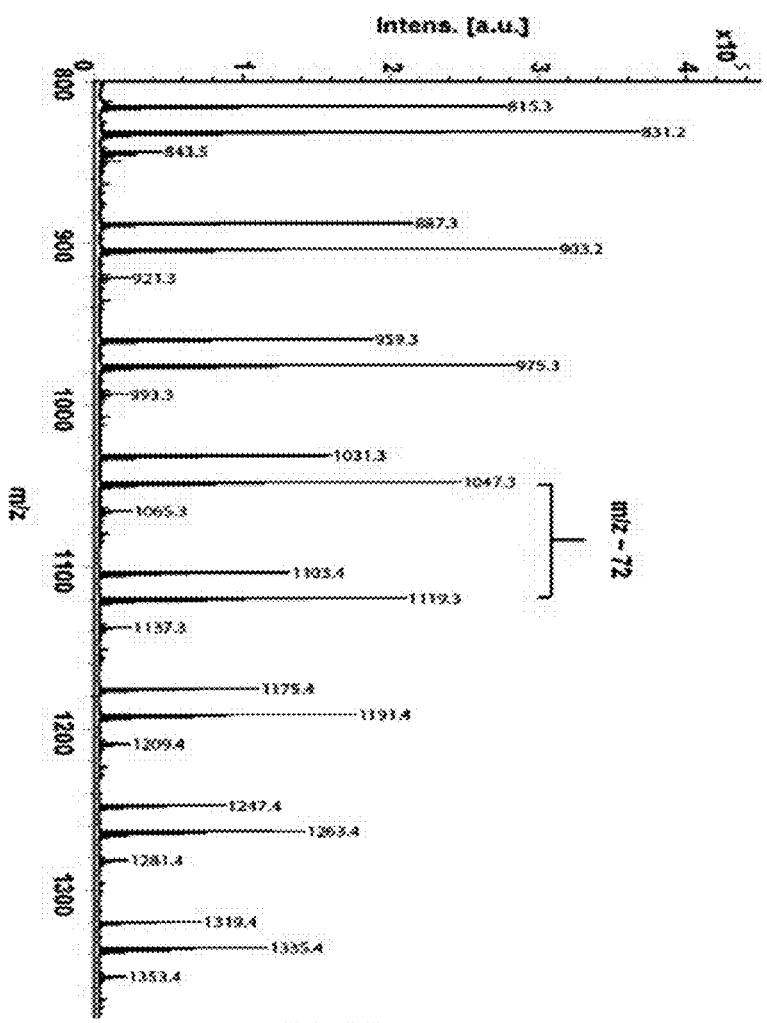
Figure 19:
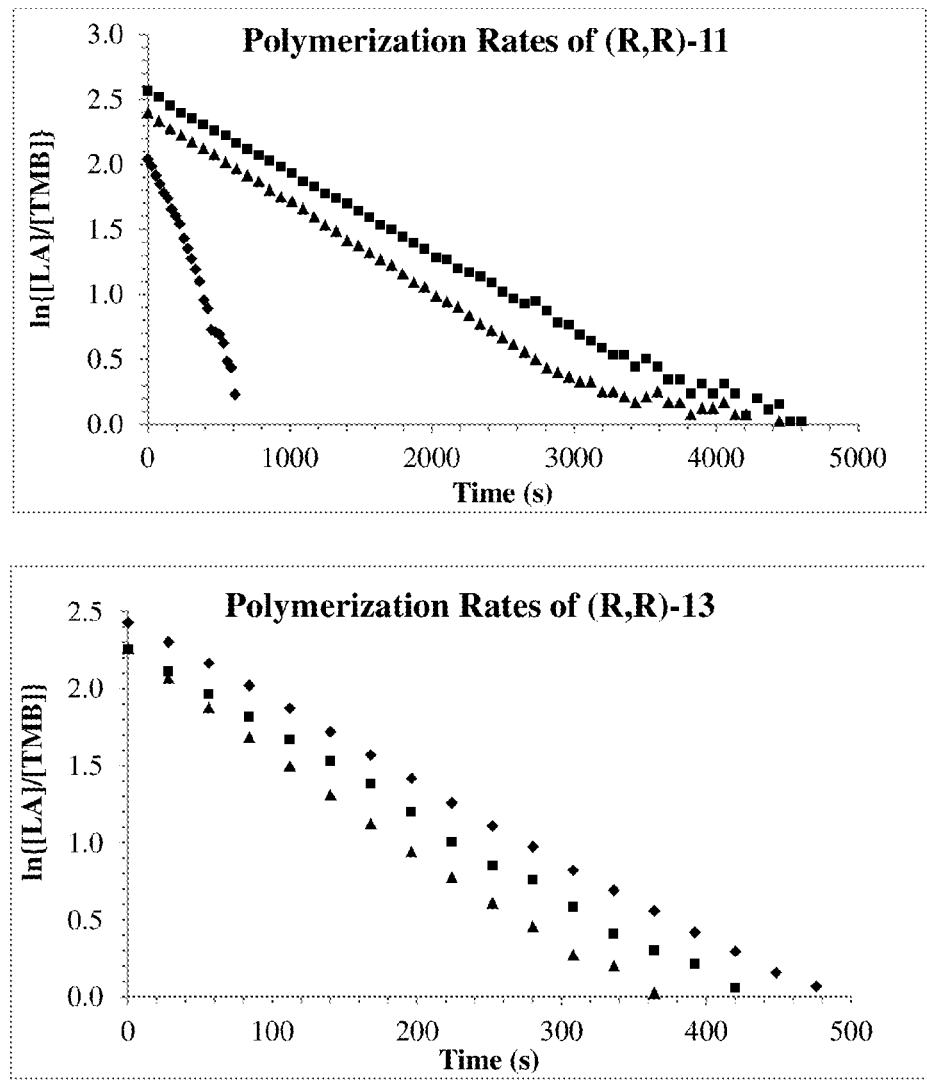
Figure 20:
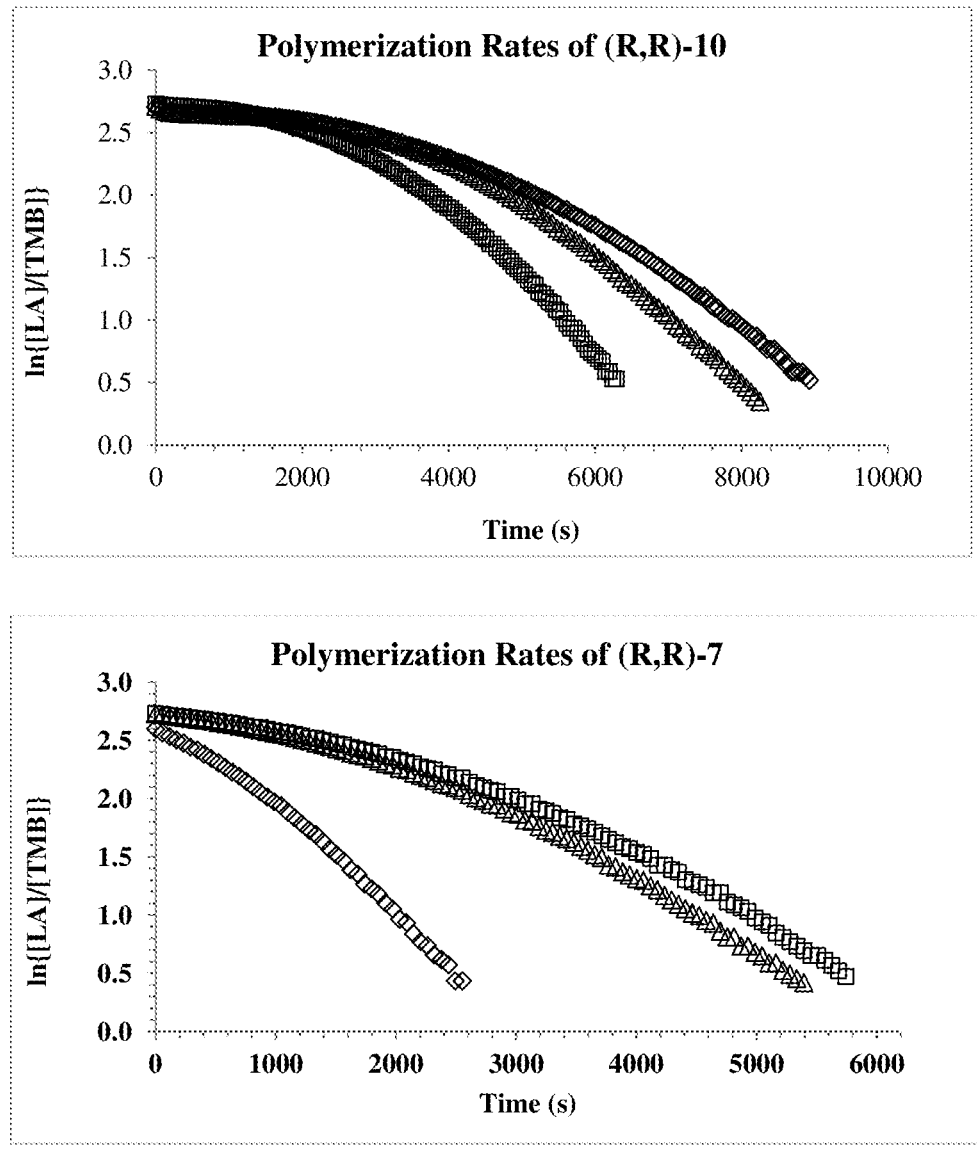
Figure 21:
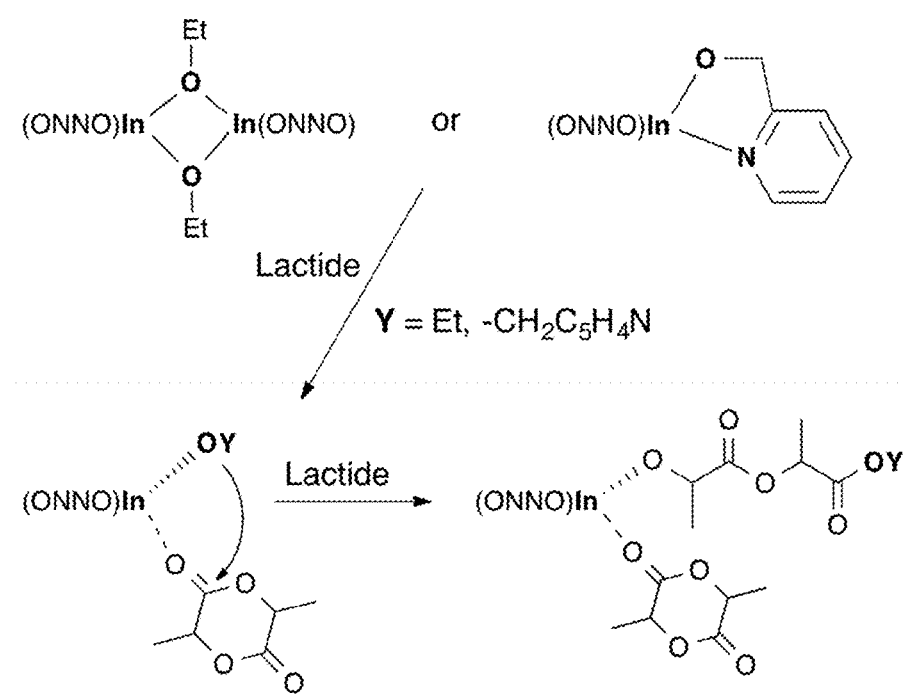

FIG. 6 depicts molecular structure of Salen-In complex ±-3, depicted with ellipsoids at 50% probability (H atoms omitted for clarity), selected bond lengths (Å) and angles (°) for ±-3: In1-Cl1 2.3704(7), In1-N1 2.194(2), In1-O1 2.0661 (16), In1-N2 2.194(2), In1-O2 2.0648(16), O2-In1-Cl1 112.57(6), O2-In1-N1 133.07(9), N1-In1-Cl1 100.29(7), O1-In1-N1 85.27(7), N2-In1-Cl1 112.57(6), O2-In1-N2 83.93(7), O2-In1-O1 95.88(7), O1-In1-N2 151.87(8);

FIG. 7 depicts molecular structures of Salen-In complex (R,R)-2.CH$_3$CN depicted with ellipsoids at 50% probability (H atoms omitted for clarity), selected bond lengths (Å) and angles (°) for (R,R)-2: In1-Cl1 2.470(1), In1-N1 2.213(3), In1-O1 2.066(3), In1-N2 2.181(3), In1-O2 2.071(3), In1-N5 2.521(4), O1-In1-Cl1 95.41(8), O2-In1-N1 157.36(11), O2-In1-Cl1 100.68(8), O1-In1-N1 87.62(11), N1-In1-Cl1 98.59(8), O2-In1-N2 89.52(12), N2-In1-Cl1 96.93(9), O1-In1-N2 161.07(11), O2-In1-O1 102.24(11), N1-In1-N2 76.40(12), Cl1-In1-N5 175.44(9), O1-In1-N5 84.85(11);

FIG. 8 depicts molecular structure of (R,R)-7 depicted with ellipsoids at 50% probability (H atoms and solvent molecules omitted for clarity);

FIG. 9 depicts a one-pot synthesis of Salen-In complexes 6-10;

FIG. 10 depicts synthesis of (R,R)—(ONNO$_R$)InOCH$_2$Pyr homonuclear In complexes;

FIG. 11 depicts (top) molecular structure of (R,R)-11 depicted with ellipsoids at 50% probability (H atoms and solvent molecules omitted for clarity), and (bottom) molecular structure of (R,R)-12 depicted with ellipsoids at 50% probability (H atoms omitted for clarity);

FIG. 12 depicts a graph plotting $\ln(I/I_0)$ vs. $\gamma^2\delta^2G^2[\Delta-(\delta/3)]\times10^{-10}$ (m$^2$ s) from PGSE experiment for complexes (R,R)-7-11, 13 in CD$_2$Cl$_2$ at 25° C.; intensities of four well separated peaks were individually plotted to obtain the above trend lines; slopes from the trend line for each peak were averaged to obtain the translational diffusion coefficient ($D_t$); I=observed spin echo intensity, I$_0$=intensity in the absence of a gradient, G=gradient strength, γ=gyromagnetic ratio, δ=length of gradient pulse, Δ=delay between gradient midpoints;

FIG. 13 depicts cross over experiments of complexes (R,R)-6 with (R,R)-8 or (R,R)-10;

FIG. 14 depicts $^1$H{H} NMR spectrum (CDCl$_3$, 25° C., 600 MHz) of methine region of PLA generated with (R,R)-6;

FIG. 15 depicts a heat flow vs. temperature curve for PLA formed from polymerization of rac-lactic acid with (R,R)-6 at a monomer:initiator ratio of 400 at 25° C. in CH$_2$Cl$_2$ (P$_m$=0.77); curve shows a glass transition temperature of 55° C. and no melting point;

FIG. 16 depicts plots for rate of polymerization (ROP) of 200 equiv L-LA (♦), D-LA (■) and rac-LA (▲) vs. time for (R,R)-6 (top) (R,R)-8 (middle) and (R,R)-9 (bottom); all reactions were carried out in CD$_2$Cl$_2$ at 25° C. and followed to 90% conversion by $^1$H NMR spectroscopy; [Catalyst]=0.0011 M, [LA]=0.45 M; value of k$_{obs}$ was determined from slope of plots of ln([LA]/[TMB]) vs. time (TMB=1,3,5-trimethoxybenzene);

FIG. 17 depicts a plot of observed PLA M$_n$ (♦) and molecular weight distribution (■) as functions of lactide:ethoxide in polymerizations with (R,R)-11 (M$_n$=number averaged molecular weight, PDI=polydispersity index); line indicates calculated M$_n$ values based on the lactide:ethoxide ratio; all reactions were carried out at room temperature in CH$_2$Cl$_2$ and polymer samples obtained at >90% conversion;

FIG. 18 depicts MALDI-TOF mass spectrum of a PLA oligomer grown with (R,R)-11;

FIG. 19 depicts plots for ROP of 200 equiv L-LA (♦), D-LA (■) and rac-LA (▲) vs. time for (ONNO$_{tBu}$)InOCH$_2$Pyr (R,R)-11 (top) and (ONNO$_{Br}$)InOCH$_2$Pyr (R,R)-13 (bottom); all reactions were carried out in CD$_2$Cl$_2$ at 25° C. and followed to 90% conversion by $^1$H NMR spectroscopy; [Catalyst]=0.0011 M, [LA]=0.45 M; k$_{obs}$ determined from slope of plots of ln([LA]/[TMB]) vs. time (TMB=1,3,5-Trimethoxybenzene);

FIG. 20 depicts plots for the ROP of 200 equiv L-LA (♦), D-LA (■) and rac-LA (▲) vs. time for [(ONNO$_{Br}$)InOEt]$_2$ (R,R)-10 (top) and [(ONNO$_{Me}$)InOEt]$_2$ (R,R)-7 (bottom); all reactions were carried out in CD$_2$Cl$_2$ at 25° C. and followed to 90% conversion by $^1$H NMR spectroscopy; [Catalyst]=0.0011 M, [LA]=0.45 M; value of k$_{obs}$ was determined from slope of plots of ln([LA]/[TMB]) vs. time (TMB=1,3,5-trimethoxybenzene);

FIG. 21 depicts a proposed initiation mechanism for polymerization reactions comprising the herein described catalyst systems;

Table 1 delineates polymerization data from Initial Studies of Homonuclear Salen-In Catalysts;

Table 2 delineates selected crystallographic parameters of X-ray structures for Salen-In complexes (R,R)-2, -3, -7, -11, and -13;

Table 3 delineates diffusion constants and hydrodynamic radii of compounds calculated using PGSE NMR spectroscopy;

Table 4 delineates polymerization of rac-lactide with Salen-In complexes;

Table 5 delineates GPC data for depolymerisation experiments; and

Table 6 delineates rate constants for polymerization of D-, L-, and rac-LA with (R,R)-8, (RR)-9, (R,R)-11 and (R,R)-13.

DETAILED DESCRIPTION OF THE INVENTION

Definitions

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, "halogen", "halide", or "halo" refers to F, Cl, Br or I.

As used herein, "alkyl" refers to a linear, branched or cyclic, saturated, unsaturated, or partially unsaturated hydrocarbon group, which can be unsubstituted or is optionally substituted with one or more substituent. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl and 1-octyl. As used herein the term "alkyl" encompasses cyclic alkyls, or cycloalkyl groups. The term "cycloalkyl" as used herein refers to a non-aromatic, saturated monocyclic, bicyclic or tricyclic hydrocarbon ring system containing at least 3 carbon atoms. Examples of $C_3$-$C_{12}$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, the term "alkenyl" refers to a straight, branched or cyclic hydrocarbon group containing at least one double bond, which can be unsubstituted or optionally substituted with one or more substituents.

As used herein, "alkynyl" refers to an unsaturated, straight or branched chain hydrocarbon group containing at least one triple bond, which can be unsubstituted or optionally substituted with one or more substituents.

As used herein, "allenyl" refers to a straight or branched chain hydrocarbon group containing a carbon atom connected by double bonds to two other carbon atoms, which can be unsubstituted or optionally substituted with one or more substituents.

As used herein, "aryl" refers to hydrocarbons derived from benzene or a benzene derivative that are unsaturated aromatic carbocyclic groups of from 6 to 100 carbon atoms, or from which may or may not be a fused ring system, in some embodiments 6 to 50, in other embodiments 6 to 25, and in still other embodiments 6 to 15. The aryls may have a single or multiple rings. The term "aryl" as used herein also includes substituted aryls. Examples include, but are not limited to phenyl, naphthyl, xylene, phenylethane, substituted phenyl, substituted naphthyl, substituted xylene, substituted phenylethane and the like. As used herein, "heteroaryl" refers to an aryl that includes from 1 to 10, in other embodiments 1 to 4, heteroatoms selected from oxygen, nitrogen and sulfur, which can be substituted or unsubstituted.

As used herein, "cycle" refers to an aromatic or nonaromatic monocyclic or multicyclic (e.g., bicyclic or tricyclic) ring of carbon atoms, and which can be substituted or unsubstituted. Included within the term "cycle" are cycloalkyls and aryls, as defined above.

As used herein, a "heterocycle" is an aromatic or non-aromatic monocyclic or multicyclic (e.g., bicyclic or tricyclic) ring of carbon atoms and from 1 to 4 heteroatoms selected from oxygen, nitrogen and sulfur, and which can be substituted or unsubstituted. Included within the term "heterocycle" are heteroaryls, as defined above. Examples of 3- to 9-membered heterocycles include, but are not limited to, aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl.

As used herein, "aminoalkyl" refers to a moiety with a structure —R'''—NR'R'', where R''' is selected from alkyl, alkenyl, alkynyl, allenyl, aryl or heteroaryl as defined above, and R' and R'' are independently selected from hydrogen or alkyl or alkenyl or alkynyl or aryl or heteroaryl as defined above.

As used herein, "aminoaryl" refers to a moiety with a structure —R'''—NR'R'', where R''' is selected from alkyl, alkenyl, alkynyl, allenyl, aryl or heteroaryl as defined above, and R' and R'' are independently selected from hydrogen or alkyl or alkenyl or alkynyl or aryl or heteroaryl as defined above, wherein at least one of R', R'' and R''' is aryl as defined above.

As used herein, "thioalkyl" refers to a moiety with a structure —R'''—SR', where R''' is selected from alkyl, alkenyl, alkynyl, allenyl, aryl or heteroaryl as defined above, and R' is selected from hydrogen or alkyl or alkenyl or alkynyl or aryl or heteroaryl as defined above.

As used herein, "thioaryl" refers to a moiety with a structure —R'''—SR', where R''' is selected from alkyl, alkenyl, alkynyl, allenyl, aryl or heteroaryl as defined above, and R' is selected from hydrogen or alkyl or alkenyl or alkynyl or aryl or heteroaryl as defined above, wherein at least one of R' and R''' is aryl as defined above.

As used herein, "phosphinoalkyl" refers to a moiety with a structure —R'''—PR'R", where R''' is selected from alkyl, alkenyl, alkynyl, allenyl, aryl or heteroaryl as defined above, and R' and R" are independently selected from hydrogen or alkyl or alkenyl or alkynyl or aryl or heteroaryl as defined above.

As used herein, "phosphinoaryl" refers to a moiety with a structure —R'''—PR'R" where R''' is selected from alkyl, alkenyl, alkynyl, allenyl, aryl or heteroaryl as defined above, and R' and R" are independently selected from hydrogen or alkyl or alkenyl or alkynyl or aryl or heteroaryl as defined above, wherein at least one of R" and R''' is aryl as defined above.

As used herein, "ether radical" refers to a moiety with a structure —R'''—OR' where R''' is selected from alkyl, alkenyl, alkynyl, allenyl, aryl or heteroaryl as defined above, and R' is selected from hydrogen or alkyl or alkenyl or alkynyl or aryl or heteroaryl as defined above.

As used herein, "substituted" refers to the structure having one or more substituents. A substituent is an atom or group of bonded atoms that can be considered to have replaced one or more hydrogen atoms attached to a parent molecular entity. In the present case, a substituent does not negatively affect the connectivity of the ligand. Examples of substituents include, but are not limited to, aliphatic groups (e.g., alkyl, alkenyl, alkynyl, etc.), halide, carbonyl, acyl, dialkylamino, arylcarbonyloxy, alkoxycarbonyloxy, aryloxycarbonyloxy, alkoxycarbonyl, amido, alkylthiocarbonyl, alkoxy, aryloxy, phosphate ester, phosphonato, phosphinato, cyano, amino, acylamino, tertiary amido, imino, alkylthio, arylthio, sulfonato, sulfamoyl, tertiary sulfonamido, nitrile, trifluoromethyl, trifluoromethoxy, heterocyclics, aromatic, and heteroaromatic moieties, ether, ester, boron-containing moieties, tertiary phosphines, and silicon-containing moieties. Silicon-containing moieties include silylated complexes such as $SiR_3$ where R is an alkyl or aryl or combinations thereof.

The terms "dispersity" and "polydispersity" refer to the dispersions of distributions of molar masses (or relative molecular masses, or molecular weights) and degrees of polymerization in polymeric systems. (INTERNATIONAL UNION OF PURE AND APPLIED CHEMISTRY—Dispersity in polymer science IUPAC Recommendations 2009; Pure Appl. Chem., Vol. 81, No. 2, pp. 351-353, 2009) The polydispersity index (PDI) is defined as the weight-average molecular weight divided by the number-average molecular weight ($M_w/M_n$). Both the $M_w$ and the $M_n$ can be determined by gel permeation chromatography or GPC. GPC can also be used in conversion experiments to determine the molecular weights of polymer samples. Polydispersity can be measured using GPC, providing a distribution of molecular weights ($M_n$). Molecular weights are measured versus standards and corrected ($M_n^c$) for changes in elution times.

The term "tacticity," as used herein, refers to the relative stereochemistry of adjacent chiral centres within a polymer. Two adjacent structural units in a polymer are referred to as a dyad. When the two structural units have the same stereochemistry, the dyad is a "meso" dyad. If the two adjacent structural units have different stereochemistry, the dyad is a "racemic" dyad. Isotacticity is the extent to which a polymer is isotactic, where an isotactic polymer is one composed of meso dyads. The degree of isotacticity of a polymer can be quantified using $P_m$ values, where $P_m$ is the probability of finding meso dyads in a polymer. A $P_m$ of 1 is a polymer that is 100% isotactic and a $P_m$ of 0.5 is a polymer with no tacticity, in other words it is atactic.

As used herein, a "coordinating atom" refers to an atom having a lone pair of electrons capable of coordinating, or forming a dative bond, with a metal atom.

The term "coordinating alkoxide" as used herein, refers to an alkoxide ligand substituted with at least one other metal-coordinating moiety, such as, but not limited to, a thio group, amino group, phosphino group, ethereal group, and/or heteroaryl group, such that the alkoxide oxygen and the at least one metal-coordinating moiety each form a coordination bond with the indium metal center.

As used herein the term "indium salt" refers to any salt of indium capable of reacting with the salen ligands presently described to form an indium complex. It is understood that indium, which has a valence of +3, would be added to the reaction as $InX_3$, wherein each X is independently an acceptable anion. Acceptable anions for the indium salt can be, for example, halogen, alkoxide (e.g., ethoxide) or triflate.

Mononuclear Salen Indium Complexes

The term "salen ligand" is typically used to refer to a class of chelating ligands derived from salicylaldehydes, and their corresponding complexes. Salen ligands comprise two imine nitrogens. However, for the sake of simplicity, the terms "salen ligand" and "salen complex" are used to also refer to "salan" ligands and complexes, in which the two nitrogens are saturated (i.e., they include two amine nitrogens rather than two imine nitrogens) and "salalen" ligands and complexes, in which one nitrogen is an imine nitrogen and the other is an amine nitrogen.

Described herein are mononuclear salen indium complexes that are useful as catalysts, for example, in stereoselective polymerization of lactide, methods of synthesis thereof, and methods of synthesizing isotactically enriched polylactic acid. Complexes similar to those described herein were disclosed in PCT application No. PCT/CA2013/050191, entitled 'Salen Indium Catalysts and Methods of Manufacture and Use Thereof (incorporated herein by reference in its entirety). PCT application PCT/CA2013/050191 disclosed both dinuclear and mononuclear salen indium complexes (where the dimeric forms optionally retained their dimeric form in solution and in solid state). The complexes provided in the present application have been found to exhibit particular desirable characteristics, in terms of structure, ease and cost of synthesis, stability in air and water, and duration of initiation period when employed as catalysts, which were not disclosed or contemplated in PCT/CA2013/050191.

In accordance with one aspect, there is provided a complex having the structure of formula Ia:

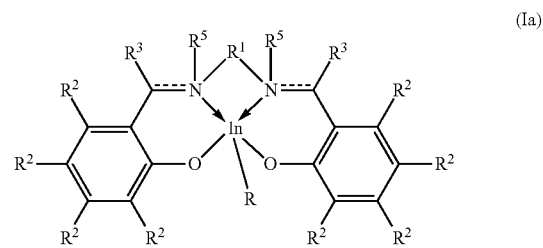

(Ia)

wherein
the dashed line represents an optional double bond;
R¹ is an optionally substituted $C_{2-5}$ alkylene,

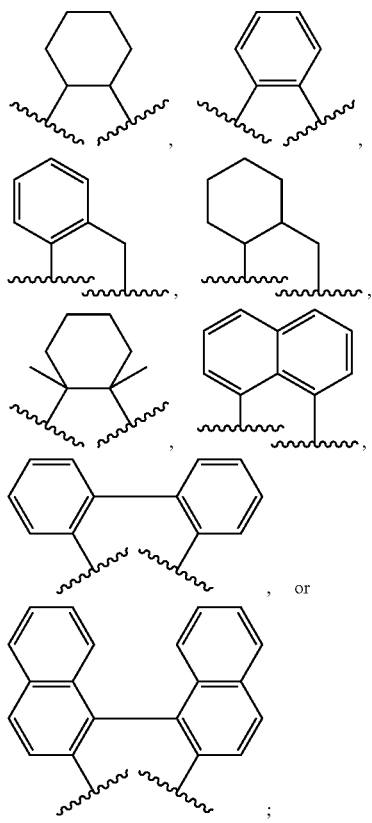

, or

;

each $R^2$ is independently hydrogen, halogen, optionally substituted linear or branched $C_{1-18}$ alkyl (e.g., $C_{1-10}$ alkyl), optionally substituted cyclic $C_{3-18}$ alkyl (e.g., cyclic $C_{3-12}$ alkyl), or optionally substituted phenyl or SiR', where R' is alkyl or aryl;

each $R^3$ is hydrogen or optionally substituted linear or branched $C_{1-18}$ alkyl (e.g., $C_{1-10}$ alkyl), or optionally substituted cyclic $C_{3-18}$ alkyl (e.g., cyclic $C_{3-12}$ alkyl);

R is a coordinating alkoxide of formula $OR^4$, wherein $R^4$ comprises at least one coordinating atom that forms a dative bond with In; and each $R^5$ is independently hydrogen, optionally substituted linear or branched $C_{1-18}$ alkyl (e.g., $C_{1-10}$ alkyl), optionally substituted cyclic $C_{3-18}$ alkyl (e.g., cyclic $C_{3-12}$ alkyl) or, when there is a C—N double bond, absent.

Without wishing to be bound by theory, it appears that the present mononuclear complexes benefit from inclusion of the coordinating alkoxide as a ligand, which saturates vacant coordination sites about the In, thus forming a stable, mononuclear, 6-coordinate complex, and preventing formation of a dimer system as disclosed in PCT application PCT/CA2013/050191, and/or preventing complex-aggregation, a phenomenon observed with other indium alkoxides (Yu, I.; Acosta Ramírez, J. A.; Mehrkhodavandi, P. *J. Am. Chem. Soc.* 2012, 134(30), 12758-12773; Aluthge, D. C.; Yan, E. X., Ahn, J.-M.; Mehrkhodavandi, P. *Inorg. Chem.* 2014, *Inorg. Chem.* 2014, 53(13), 6828-6836

The present inventors have found that complexes described herein can offer faster polymerization rates due to shorter, or negligible, initiation periods, relative to those obtained using the complexes disclosed in PCT application PCT/CA2013/050191. Without wishing to be bound by theory, it appears that the dimers previously disclosed in PCT/CA2013/050191 dissociate in order to commence polymerization. Since the coordinating alkoxide ligand of the complexes described herein appear to function, at least in part, to prevent formation of dimers, no such dissociation step is required, thereby increasing polymerization rates.

Further, the present studies demonstrate that complexes described herein can be more air and water stable than those disclosed in PCT application PCT/CA2013/050191; without wishing to be bound by theory, it has been postulated that this stability is a potential consequence of the indium metal center being coordinatively saturated.

It is also anticipated that the complexes described herein will be cheaper and easier to produce on a larger scale, given that only one salen ligand will be bound to the metal centre, and chemical procedures for adding a coordinating alkoxide ligand to the indium complex is a reasonably facile, one step process.

In one embodiment, the mononuclear indium complex of the present application has a structure of formula (Ib):

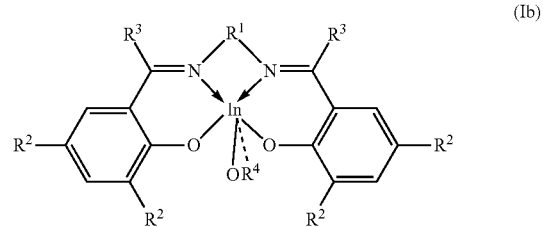

(Ib)

wherein,
the dashed line represents a dative bond between a coordinating atom in $R^4$ and In;

$R^4$ is bonded to O, and is an optionally substituted aminoalkyl or aminoaryl, optionally substituted thioalkyl or thioaryl, optionally substituted phosphinoalkyl or phosphinoaryl, or optionally substituted ether radical, which forms a dative bond with In via the respective heteroatom; or, $R^4$ is bonded to O, and has the structure of formula (Ic)

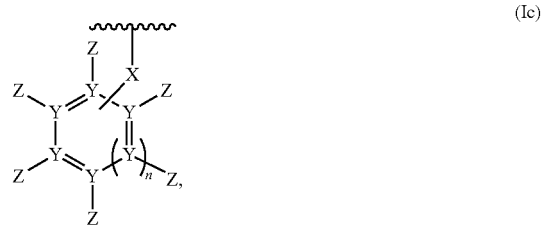

(Ic)

wherein
n is 0 to 8;
each Z is independently absent, at least one lone pair of electrons, or a hydrogen, halogen, hydroxide, optionally substituted linear or branched $C_{1-18}$ alkyl (e.g., $C_{1-10}$ alkyl), optionally substituted cyclic $C_{3-18}$ alkyl (e.g., cyclic $C_{3-12}$ alkyl), optionally substituted phenyl or SiR', where R' is alkyl or aryl, optionally substituted heteroaryl, optionally substituted $C_{1-18}$ amino, $C_{1-18}$ alkyl alkoxide; or, any two Z, together with the atoms to which they are attached, combine to form a cycle or heterocycle;

X is absent, optionally substituted linear or branched $C_{1-8}$ alkyl, optionally substituted cyclic $C_{3-8}$ alkyl, optionally substituted aryl, or optionally substituted heteroaryl; and each Y is independently C or a coordinating atom, wherein at least two Y are C, and at least one Y coordinates to In.

In one embodiment, $R^4$ of formula (Ic) has the general structure of formula (Id)

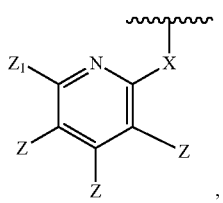

(Id)

wherein X and each Z are as defined above; and $Z_1$ is the same as Z, or $Z_1$ is a sterically bulky group, such as, but not limited to, a sterically substituted linear or branched $C_{1-18}$ alkyl (e.g., $C_{1-10}$ alkyl), sterically substituted cyclic $C_{3-18}$ alkyl (e.g., cyclic $C_{3-12}$ alkyl), sterically substituted phenyl or SiR', where R' is alkyl or aryl, sterically substituted heteroaryl, sterically substituted $C_{1-18}$ amino, $C_{1-18}$ alkyl alkoxide; or, any one of $Z_1$ and Z, together with the atoms to which they are attached, combine to form a cycle or heterocycle, each of which may be sterically substituted.

Without wishing to be bound by theory, it has been considered that varying the steric bulk adjacent to the coordinating atom(s) of $R^4$, such as, for example, with respect to structures of formula (Id), then the degree of coordination, and thus lability of the pyridine ring can be controlled: that with increasing steric bulk, the pyridine ring may coordinate less strongly.

The complex of formula Ib is depicted above as a salen complex. However, as noted above, also encompassed in the present application are the corresponding "salan" complexes, in which the two nitrogens are saturated (i.e., they include two amine nitrogens rather than two imine nitrogens) and "salalen" and complexes, in which one nitrogen is an imine nitrogen and the other is an amine nitrogen.

In accordance with one embodiment, the complex has one of the following structures:

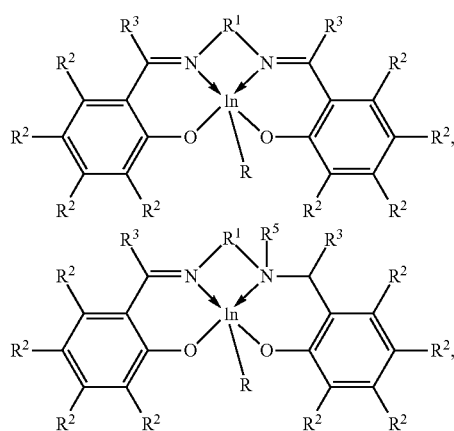

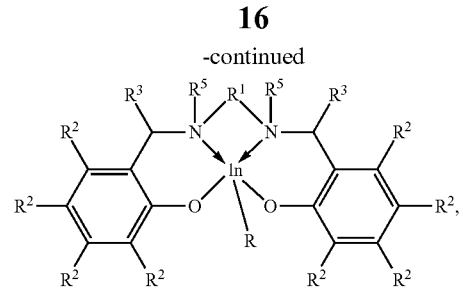

wherein substituent R is a coordinating alkoxide comprising at least one other coordinating atom that forms a dative bond with In.

For example, when R is of formula $OR^4$, and $R^4$ is a pyridyl-substituted alkylene, the mononuclear catalyst would have the structure

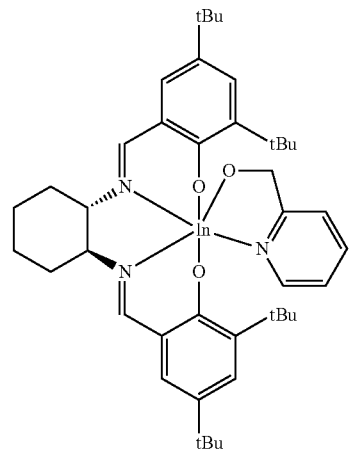

In accordance with other embodiments, $R^4$ can alternatively comprise optionally substituted aminoalkyls or amino aryls, thioalkyls or thioaryls, phosphinoalkyls or phosphinoaryls, or ether radicals that form a dative bond with In via their respective heteroatom(s).

In accordance with one embodiment, $R^1$ is

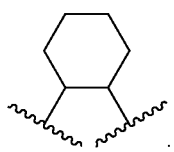

In accordance with another embodiment, at least $R^2$ is an optionally substituted $C_{1-5}$ alkyl, an optionally substituted aryl, an optionally substituted $C_3$-$C_{12}$ cyclic alkyl, or Si(aryl)$_3$; $R^3$ is H and $R^4$ is $C_{1-3}$ alkyl.

Specific, non-limiting, examples of chiral mononuclear salen indium catalysts are:

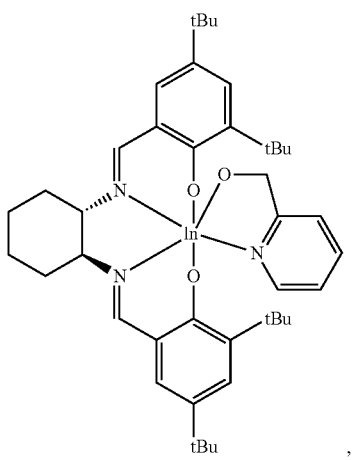

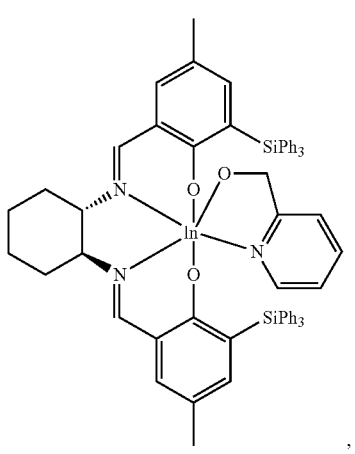

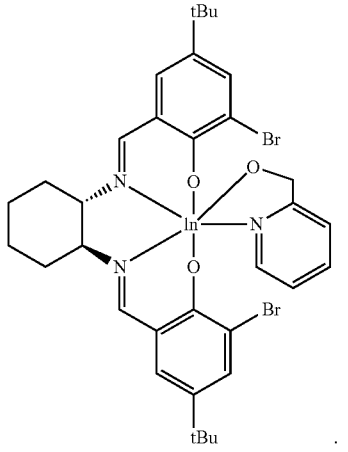

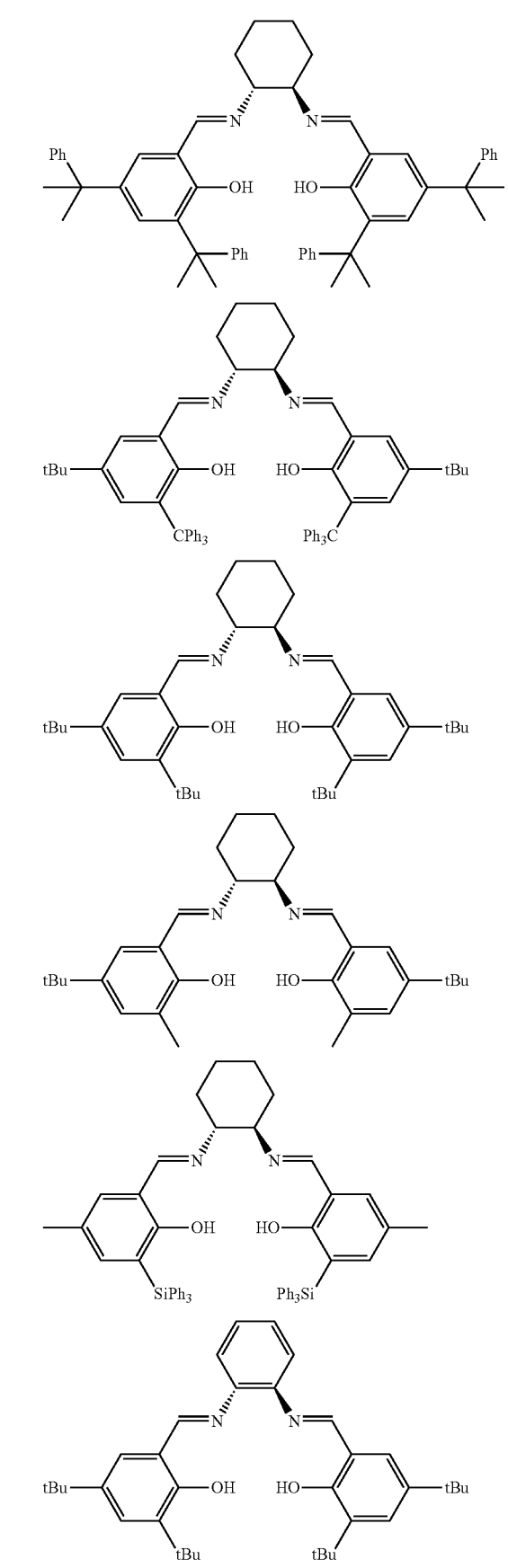

In one embodiment, the mononuclear salen indium catalysts described herein provide isotactic enrichment of polylactic acid copolymer during polymerization with lactide. In accordance with one embodiment, the substituent $R^1$ is chiral, although this is not necessary for isotactic enrichment. In accordance with one embodiment, the stereochemistry of $R^1$ is (R,R).

Specific examples of ligands used in the herein described salen indium complexes are depicted below:

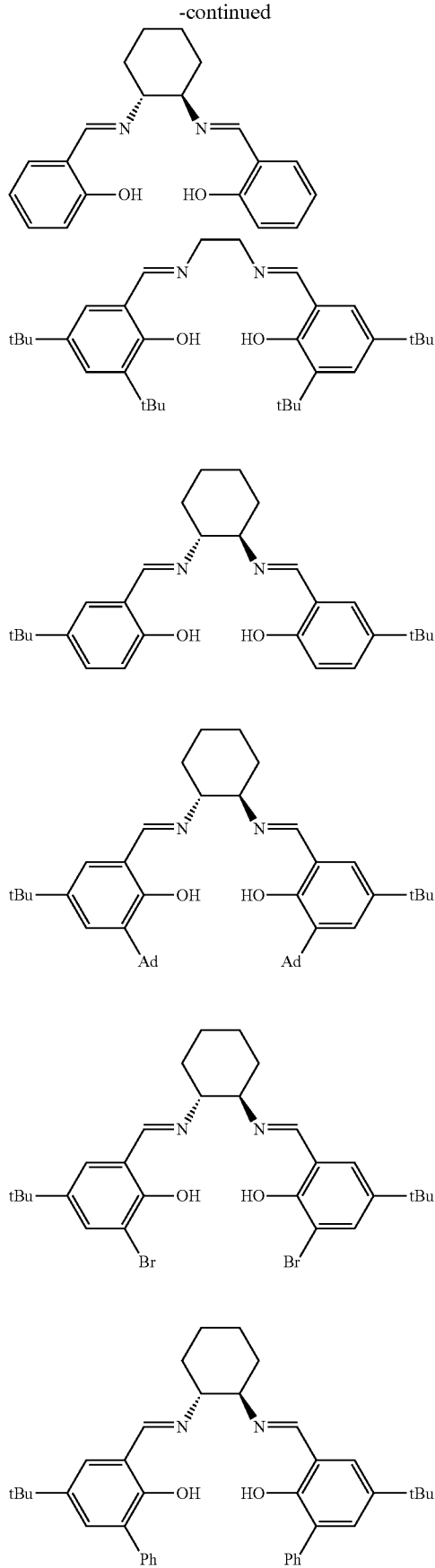
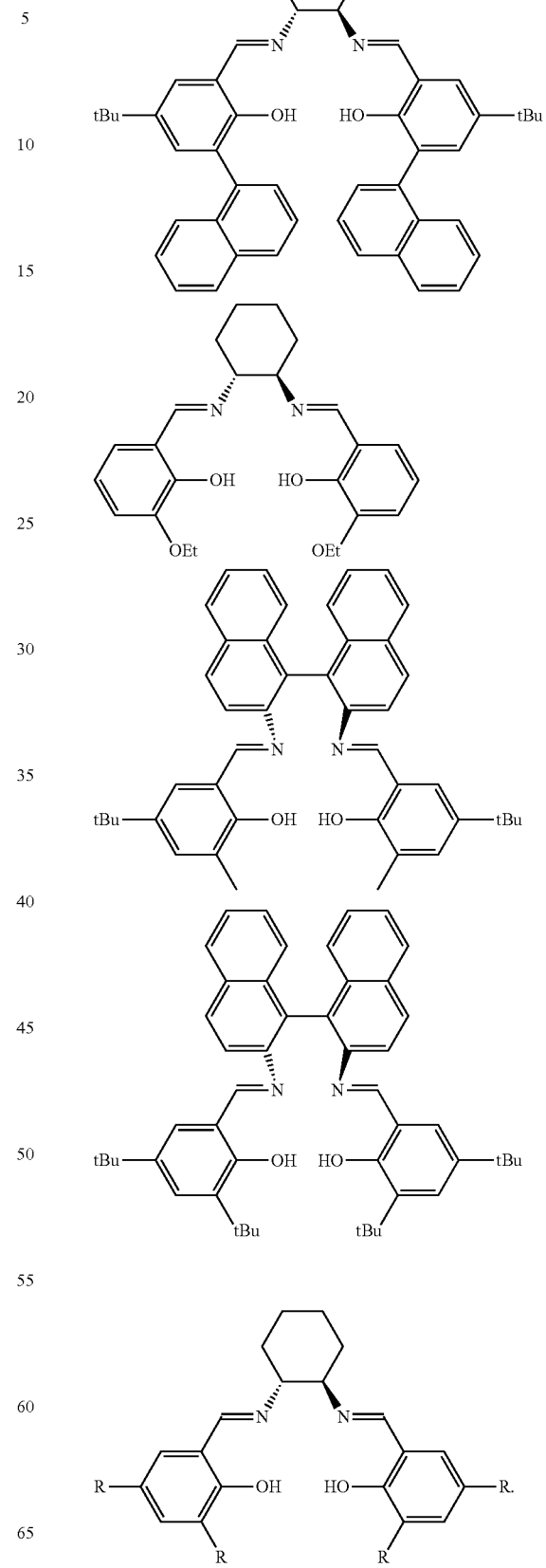

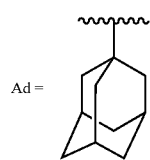

Ad =

R = cumyl = Cm = —C(CH$_3$)$_2$Ph

Polymerization and Copolymerization Methods

The mononuclear salen indium complexes described herein are effective catalysts for ring opening polymerization of cyclic ester monomers. Polymerization methods described below can include copolymerization methods.

The mononuclear salen indium catalysts described herein can be used for polymerization of cyclic esters such as, for example, lactides, beta-butyrolactone and other cyclic esters such as caprolactones. Lactides useful in polymerization methods described herein can be D-lactide, L-lactide, meso-lactide or rac-lactide. rac-lactide is a 50:50 mixture of D-lactide and L-lactide. In use in polymerizations, the lactide is often a mixture of D and L-lactides that is not a 50:50 mixture. For example, a common, commercially available lactide, that can be used in the polymerization methods described herein, is a mixture of 98% L-lactide and 2% D-lactide.

In some embodiments, the cyclic ester monomers used in the polymerization methods described herein include pendant functional groups. For example, a cyclic ester monomer used in a polymerization method can include pendant cross-linkable functional groups. This example has the added advantage of being useful in methods for manufacturing cross-linked PLA.

In accordance with one embodiment, there is provided a method comprising polymerizing a cyclic ester monomer, or combination of cyclic ester monomers, with a mononuclear salen indium catalyst, as described herein, under conditions suitable for ring-opening polymerization. A plurality of different cyclic ester monomers can be polymerized at the same time, or during different times of the entire polymerization process.

In accordance with one embodiment, the polymerization is performed simultaneously using at least two different cyclic ester monomers in order to produce a random copolymer. In an alternative embodiment, as described in more detail below, two or more cyclic ester monomers are polymerized at different times during the polymerization process to produce a block copolymer.

Further, with regard to the copolymerization methods described in below embodiments, the first cyclic ester monomers can be polymerized in a solvent or solvent system and the second cyclic ester monomer is added to the solvent or solvent system (either directly or in a second miscible second solvent).

The ring-opening polymerization methods described herein can be living polymerization methods; that is, polymerizing steps can be living polymerizing steps in the methods disclosed herein.

Typically, in living polymerizations, cyclic ester monomer is polymerized at very low polymer chain termination rates (i.e., the ability of the growing polymer chains to terminate is substantially removed). As a result, polymer chains can grow at a more constant rate (compared to traditional chain polymerization) and the polymer chain lengths remain very similar (i.e., they have a very low polydispersity index).

The ring-opening polymerization methods described herein can further be immortal ring opening polymerization methods; that is, polymerizing steps can be immortal polymerizing steps in the methods disclosed herein.

Typically, in immortal ring opening polymerization (iROP) of a cylic ester monomer, external nucleophiles act as both initiators and chain transfer agents in conjunction with a catalyst. A result can be that catalytic productivity is enhanced and metal contamination of polymers significantly reduced in comparison to classic living systems, while the polymer chain end is functionalized with the chosen chain transfer agent.

In accordance with a specific embodiment, there is provided a method of making polylactic acid comprising polymerizing lactide in the presence of a mononuclear salen indium complex as described herein.

Polymerization reactions carried out using the mononuclear salen indium complexes as described herein are well controlled and polymers with high molecular weights and low molecular weight distributions can be obtained using the present methods.

Without wishing to be bound by theory, it has been postulated that enantiomorphic site control is a contributor to selectivity. During polymerization, using a chiral catalyst, an enantiomorphic site control mechanism utilizes the chirality of the ancillary ligand, and hence, the catalyst itself is a source of stereochemical selectivity (due to steric interactions between the incoming monomer, the growing polymer chain bound to the metal centre, and the ancillary ligand). During polymerization, using an achiral catalyst, reaction of the first monomer molecule with the catalyst complex imparts chirality on the catalyst leading to stereochemical selectivity towards incoming monomers.

Stereoselective ring opening polymerization of lactide can be carried out using the methods of polymerization and mononuclear salen indium complex catalysts, as described herein. In one embodiment, PLA is produced in a polymerization reaction of rac-lactide in the presence of a mononuclear salen indium catalyst as described herein, according to the following scheme:

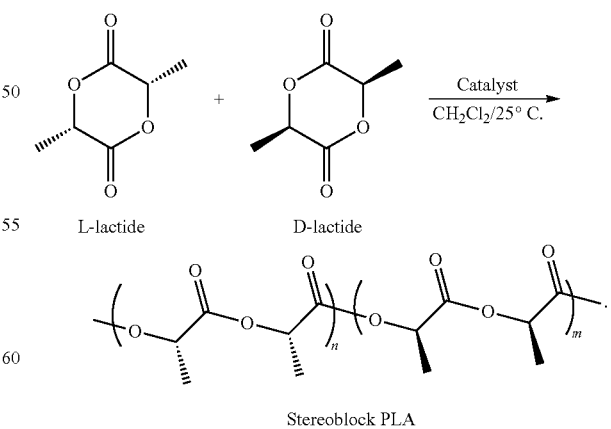

Stereoblock PLA

In accordance with another embodiment, the polylactic acid has a polydispersity index of less than about 2.0. In one embodiment, the polylactic acid has a polydispersity index of less than about 1.7. In another embodiment, the polylactic acid has a polydispersity index less than about 1.5.

In accordance with another embodiment, there is provided an isotactically enriched polylactic acid produced by the disclosed method. In one embodiment, the isotactically enriched polylactic acid has a $P_m$, or isotacticity, of greater than 0.5, or between about 0.6-1.0. In another embodiment, the isotactic enrichment is between about 0.7-1.0.

Polymerization reactions carried out using the herein described methods can be performed under a variety of conditions, and in any appropriate solvent. In one non-limiting embodiment, the appropriate solvent is $CH_2Cl_2$, tetrahydrofuran, toluene or benzene. In another non-limiting embodiment, the method can be carried out in a temperature range of 0-50° C. In one embodiment, the method is carried out at about 25° C. In another embodiment, the reactions are carried out at atmospheric pressure.

In an alternative embodiment, the polymerization reaction is performed using a bulk, or melt, process in which a mononuclear salen indium complex is mixed with a cyclic ester monomer, or combination of monomers, in the absence of a solvent. The mixture is then heated to a temperature of greater than the melting point of the monomer, or combination of monomers, for an appropriate amount of time to allow the polymerization to proceed (e.g. an hour or more). In one embodiment, the melt polymerization process is performed at a temperature of about 100° C. or more, for example, at a temperature of from about 100° C. to about 250° C., or from about 100° C. to about 200° C. In specific examples, the melt polymerization is performed at about 110° C., or about 130° C., or about 160° C., or about 190° C.

In another embodiment, there is provided a copolymerization method for preparing a block copolymer, comprising:

(a) polymerizing a first cyclic ester monomer with a mononuclear salen indium catalyst as described herein under conditions suitable for ring-opening polymerization of the first cyclic ester monomer to form a first polymer block of the block copolymer; and (b) polymerizing a second cyclic ester monomer, different from the first cyclic ester monomer, with the mononuclear salen indium catalyst under conditions suitable for ring-opening polymerization of the second cyclic ester monomer to form a second polymer block of the block copolymer.

The first cyclic ester monomer can be any cyclic ester monomer. Similarly, the second cyclic ester monomer can be any cyclic ester monomer. Suitable cyclic ester monomers that can be used in the present polymerization methods, including the first and/or the second step of the co-polymerization method, include, but are not limited to lactide, D-lactide, L-lactide, meso-lactide, rac-lactide, unequal mixtures of D- and L-lactide, or mixtures of D-, L- and meso-lactide, β-butyrolactone, caprolactone, or 4-(but-3-en-1-yl)oxetan-2-one.

In a specific embodiment, at least one of the first and second cyclic ester monomers used in the copolymerization method is a lactide. In a related embodiment, both the first and second cyclic ester monomers are lactides.

In a further embodiment, the copolymerization method can further comprise:

(c) polymerizing a third cyclic ester monomer, different from the first and second cyclic ester monomer, with a mononuclear salen indium catalyst as described herein under conditions suitable for ring-opening polymerization of the third cyclic ester monomer to form a third polymer block of the block copolymer; and wherein the catalyst for step (c) is the same as the catalyst used in steps (a) and/or (b).

A further embodiment of the present invention is a polymerization method of any one of the preceding embodiments, wherein an equal or greater ratio of chain transfer agent to mononuclear salen indium catalyst is provided. The chain transfer agent is an alcohol, including, for example, an HO-polyester or HO-polyether. Suitable alcohols are $R_nOH$, where $R_n$ is any alkyl chain, including straight and branched alkyl chains. In specific examples, the alcohol is ethanol, phenol, benzyl alcohol or isopropanol. In alternative examples, the alcohol is $HO(CH_2)_nOH$, $[HO(CH_2)_n]_3(CH)$ and $[HO(CH_2)_n]_4(C)$ as well as other star shaped multiols. Polyesters can also be used, such as, for example, (OH-terminated PLA) or $HO(CH_2O)_nOH$. A specific, non-limiting example of a suitable polyether is mPEG.

In accordance with other embodiments, the chain transfer agent can be an amine, a thiol or a phosphine. A "high ratio" as referred to herein, typically, refers to a ratio that supports immortal polymerization. Typically, suitable ratios of chain transfer agent to salen indium catalyst are between about 100 and 1, between about 50 and 1; between about 20 and 1; between about 10 and 1; or between about 4 and 1.

Polylactic acid polymers produced by the methods described herein can have a polydispersity index of less than about 3.0. In a one embodiment, the polylactic acid has a polydispersity index of less than about 1.7. In another embodiment, the polylactic acid produced by the methods described herein has a polydispersity index of less than about 1.5. In one embodiment, the polylactic acid produced by the methods described herein has a molecular weight of greater than about 300, or greater than about 10,000, or from about 300 to about 10,000,000, or from about 10,000 to about 1,000,000, or, more particularly, from about 20,000 to about 150,000, or, even more particularly, from about 28,800 to about 144,000. In another embodiment, the polylactic acid produced by the methods described herein has a melting point of between about 130-178° C. In another embodiment, the polylactic acid polymers produced by the presently described methods are white, or light yellow, in color.

Synthesis of Salen Indium Complexes

Further provided herein are methods of producing the mononuclear salen indium complexes described above.

In one embodiment, there is provided a method of synthesizing a complex having the structure of formula (Ia):

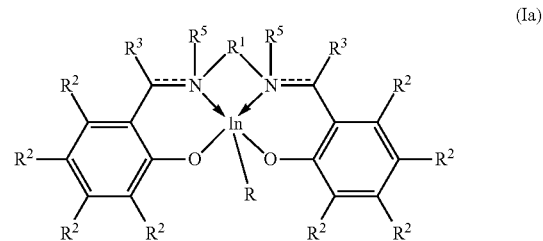

(Ia)

the dashed line represents an optional double bond;
$R^1$ is an optionally substituted $C_{2-5}$ alkylene,

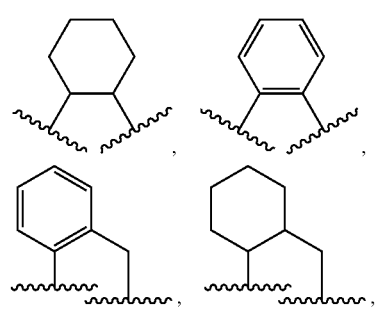

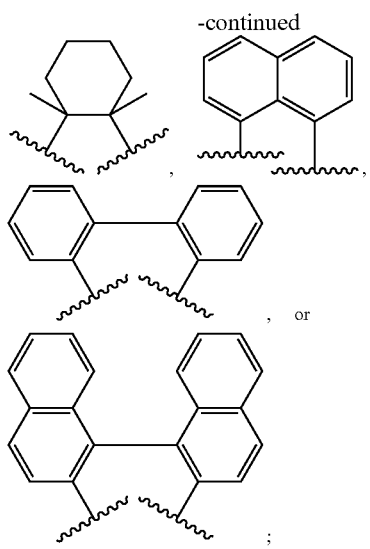

each R² is independently hydrogen, halogen, optionally substituted linear or branched $C_{1-18}$ alkyl (e.g., $C_{1-10}$ alkyl), optionally substituted cyclic $C_{3-18}$ alkyl (e.g., cyclic $C_{3-12}$ alkyl), optionally substituted phenyl or SiR', where R' is alkyl or aryl;

each R³ is hydrogen or optionally substituted linear or branched $C_{1-18}$ alkyl (e.g., $C_{1-10}$ alkyl), optionally substituted cyclic $C_{3-18}$ alkyl (e.g., cyclic $C_{3-12}$ alkyl);

R is a coordinating alkoxide of formula OR⁴, wherein R⁴ comprises at least one coordinating atom that forms a dative bond with In; and each R⁵ is independently hydrogen, optionally substituted linear or branched $C_{1-18}$ alkyl (e.g., $C_{1-10}$ alkyl), optionally substituted cyclic $C_{3-18}$ alkyl (e.g., cyclic $C_{3-12}$ alkyl) or, when there is a C—N double bond, absent, comprising:

a) reacting a compound of formula (IIa) with a strong base to give a diphenoxide

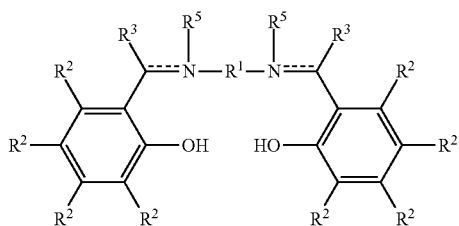

b) complexing the diphenoxide of step a) with an indium salt $InX_3$ to give an indium complex of formula (IIb),

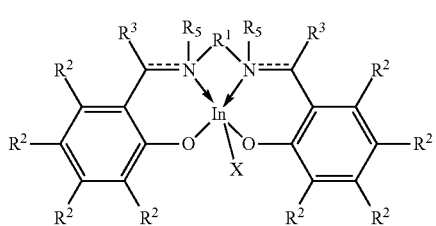

wherein X is an anion, and c) reacting the indium complex of formula (IIb) with a salt of R⁴OM, wherein M is a metal cation, such as Li⁺, Na⁺ or K⁺, or $NR^6_4{}^+$, wherein R⁶ is an alkyl.

In one embodiment, the indium salt is $InX_3$, wherein each X is independently an acceptable anion, such as, but not limited to a halide (e.g., Cl⁻), triflate or an alkoxide (e.g., ethoxide). In accordance with one embodiment, the indium salt is an indium halide. In one embodiment, the indium salt is indium triflate. In another embodiment, the indium salt is indium chloride. Some examples of acceptable anions are fluorine, chlorine, bromine, iodine, and triflate.

Generally, a mononuclear salen indium complex, as described herein, can be synthesized by reacting the corresponding salen ligand with two equivalents of ArCH₂K and subsequently reacting it with one equivalent of an indium salt. In one example, the salen ligand is converted to the corresponding phenoxide under basic conditions, and further reacted with indium chloride to give the corresponding salen indium chloride complex. This is then reacted with a coordinating alkoxide base to install the alkoxy functionality. Synthesis of one example catalyst, (R,R)—N,N'-Bis(3,5-di-tert-butylsalicylidene)-1,2-cyclohexanediamine indium pyridin-2-ylmethoxide complex (2), is shown below.

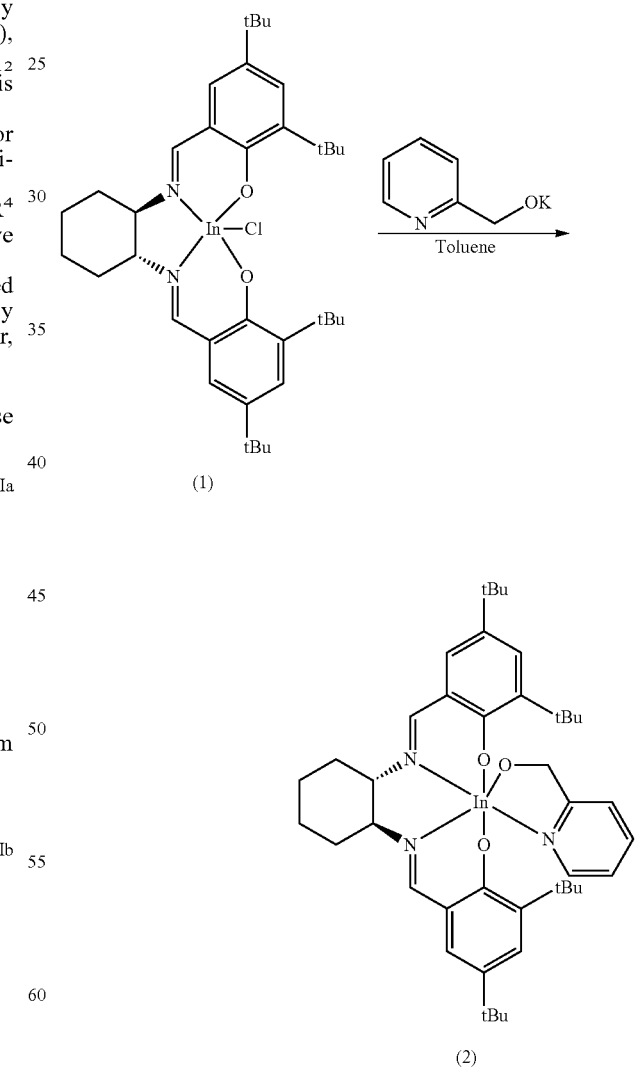

In an alternative embodiment, the mononuclear salen indium catalysts herein described can be synthesized using a one-pot synthesis. In particular, the above described three step synthesis of deprotonation of the salen ligand, reaction with $InX_3$ to form the indium halide complex, and salt metathesis to form the indium alkoxide complex can be modified into a one-pot synthesis.

In one embodiment, a non-limiting example of a one-pot synthesis of the herein described salen indium catalysts comprises reacting a salen ligand as described herein with $InCl_3$ and an access of a coordinating alkoxide, such as $KOCH_2Py$:

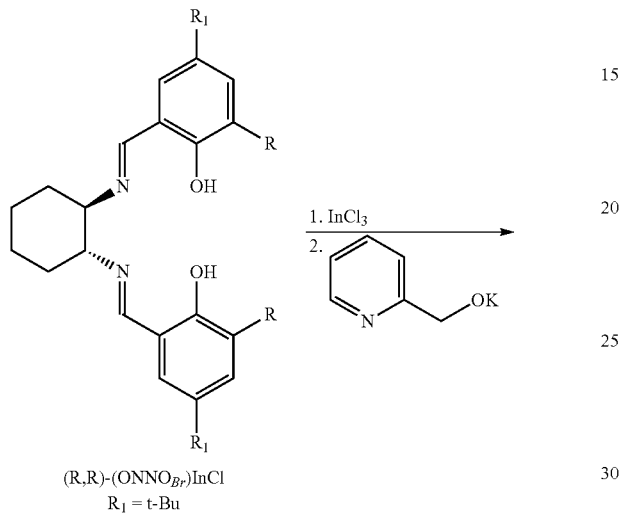

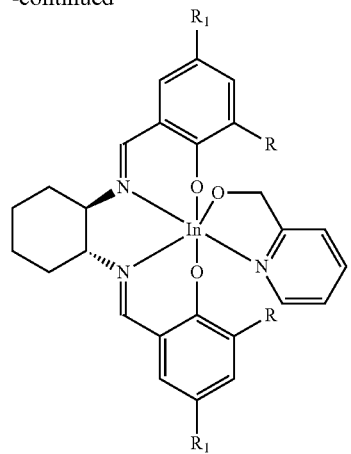

(R,R)-(ONNO$_{tBu}$)InOCH$_2$Pyr
(R,R)-(ONNO$_{SiPh3}$)InOCH$_2$Pyr
(R,R)-(ONNO$_{Br}$)InOCH$_2$Pyr

In another embodiment, a non-limiting example of a one-pot synthesis comprises reacting a salen indium chloride complex with a coordinating alkoxide, such as $KOCH_2Py$:

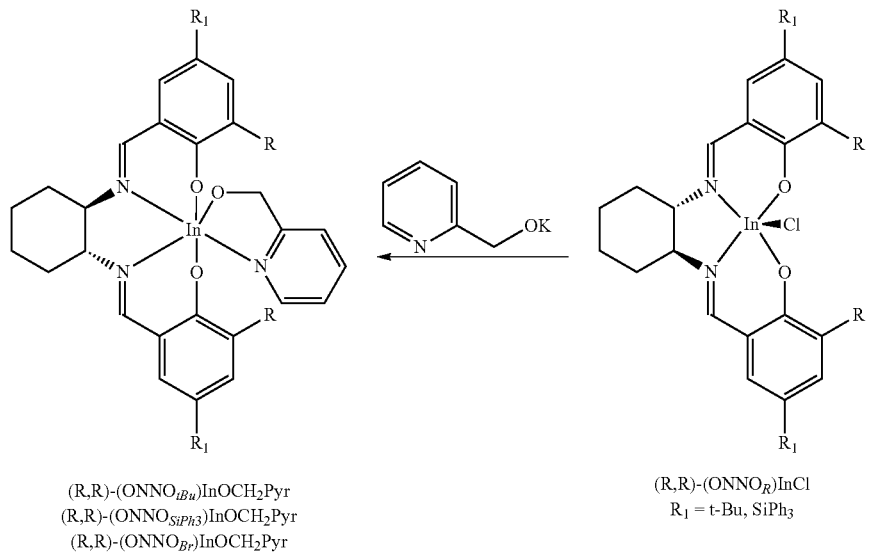

Additional, non-limiting synthetic routes for the manufacture of the mononuclear salen indium complexes are summarized in the scheme below:

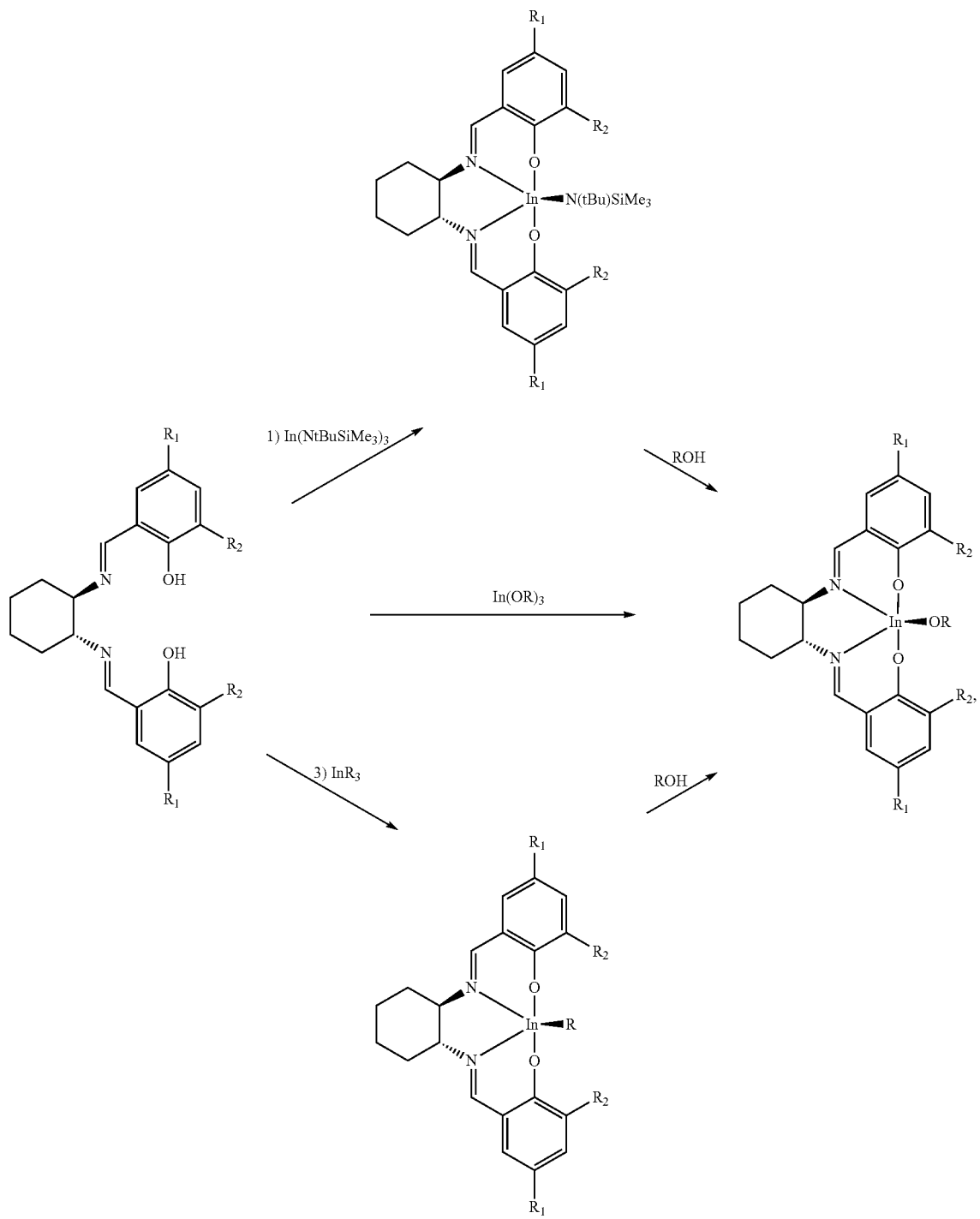

wherein R comprises a coordinating alkoxide that forms a dative bond with In.

To gain a better understanding of the invention described herein, the following examples are set forth. It should be understood that these examples are for illustrative purposes only. Therefore, they should not limit the scope of this invention in any way.

EXAMPLES

Example 1

Initial Investigations of Mononuclear Salen-In Catalysts for Ring Opening Polymerization (ROP) of Lactides General Considerations for Synthesis of Catalysts:

Unless otherwise indicated, all air- and/or water-sensitive reactions were carried out under dry nitrogen using either an MBraun glove box or standard Schlenk line techniques. NMR spectra were recorded on a Bruker Avance 400 MHz and 600 MHz spectrometer. $^1$H NMR chemical shifts are reported in ppm versus residual protons in deuterated chloroform; δ 7.27 CDCl$_3$. $^{13}$C{$^1$H} NMR chemical shifts are reported in ppm versus residual $^{13}$C in the solvent; δ 77.2 CDCl$_3$. Diffraction measurements for X-ray crystallography were made on a Bruker APEX DUO diffractometer with graphite monochromated Mo-Kα radiation. The structures were solved by direct methods and refined by full-matrix least-squares using the SHELXTL crystallographic software of Bruker-AXS. Unless specified, all non-hydrogens were refined with anisotropic displacement parameters, and all hydrogen atoms were constrained to geometrically calculated positions but were not refined. Elemental C, H, N analysis was performed using a Carlo Erba EA1108 elemental analyzer. The elemental composition of unknown samples was determined by using a calibration factor. The calibration factor was determined by analyzing a suitable certified organic standard (OAS) of a known elemental composition. Molecular weights were determined by triple detection gel permeation chromatography (GPC-LLS) using a Waters liquid chromatograph equipped with a Water 515 HPLC pump, Waters 717 plus autosampler, Waters Styragel columns (4.6×300 mm) HR5E, HR4 and HR2, Water 2410 differential refractometer, Wyatt tristar miniDAWN (laser light scattering detector) and a Wyatt ViscoStar viscometer. A flow rate of 0.5 mL min$^{-1}$ was used and samples were dissolved in THF (2 mg mL$^{-1}$). Narrow molecular weight polystyrene standards were used for calibration purposes. The molar mass was calculated with ASTRA© 5 software using the Mark-Houwink parameters (K=1.832×10$^4$ dL/g, a=0.69), laser light scattering detector data, and concentration detector. Distribution and moment procedures of ASTRA© 5 was used to calculate molar mass moments $M_n$, $M_w$ and $M_z$.

Solvents (Toluene, hexanes and diethyl ether) were collected from an MBraun Solvent Purification System whose columns are packed with activated alumina. CH$_2$Cl$_2$ was purified followed by the literature procedures to remove any impurities, dried over CaH$_2$ and degassed through a series of freeze-pump-thaw cycles. CD$_2$Cl$_2$, CDCl$_3$ and were dried over CaH$_2$, and degassed through a series of freeze-pump-thaw cycles. rac-LA was a gift from PURAC America Inc. and recrystallized twice from hot dried toluene. The salen indium chloride complex (1) was synthesized according to a previously published literature procedure (Aluthge, D. C.; Patrick, B. O.; Mehrkhodavandi, P. "A highly active site selective catalyst for lactide polymerization" Chem. Commun. 2013, 49, 4295-4297).

Preparation and Characterization of (ONNO)InCl Catalysts and Complexes

Tetradentate ligand (rac)-N,N'-Bis(3,5-di-tert-butylsalicylidene)-1,2-cyclohexanediamine and its enantiopure version (R,R), were prepared using methods previously reported (Jacobsen et al., J. Am. Chem. Soc., 1991, 113, 6703-6704; Jacobsen, E. N.; Organic Syntheses, 1998. Vol. 75, p. 1).

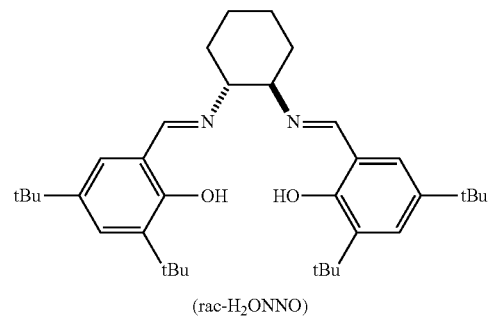

(rac-H$_2$ONNO)

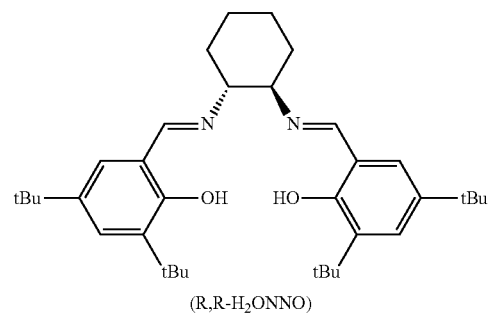

(R,R-H$_2$ONNO)

Synthesis of indium chloride complex
(R,R)—(ONNO)InCl (R,R-1')

The salen indium chloride complex (R,R-1') was synthesized by reacting the corresponding salen ligand with 2 equivalents of KCH$_2$Ph and subsequently reacting it with 1 equivalent of InCl$_3$ according to the following scheme:

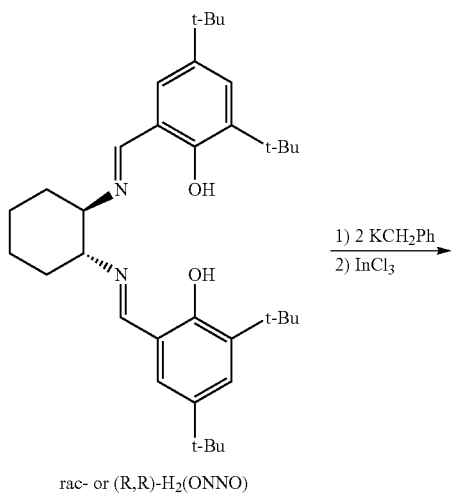

rac- or (R,R)-H$_2$(ONNO)

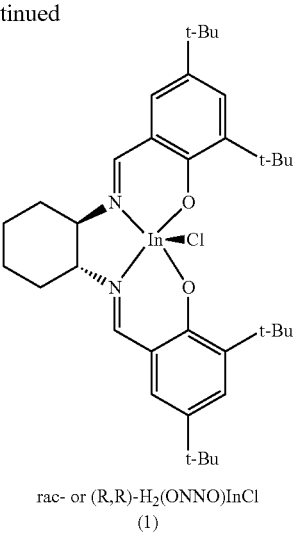

rac- or (R,R)-H₂(ONNO)InCl
(1)

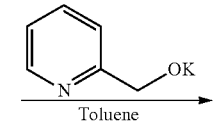

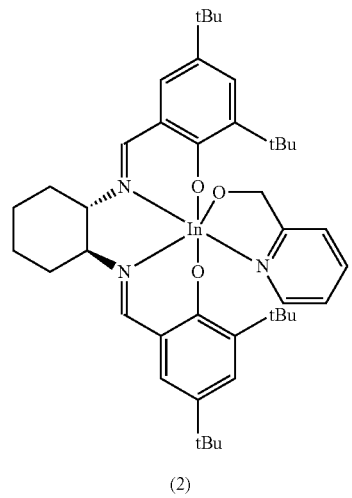

(2)

A solution of ligand (R,R)—N,N'-Bis(3,5-di-tert-butyl-salicylidene)-1,2-cyclohexanediamine (0.7252 g, 1.326 mmol), in toluene was added to a stirring slurry of KCH₂Ph (0.3451 g, 2.649 mmol) in toluene (total volume 25 mL) at room temperature. The resulting mixture was stirred at room temperature for 24 h. The solvent was subsequently evaporated under vacuum and the resulting solid was washed with cold hexanes and dried under vacuum to afford yellow solid (0.7812 g).

The resulting solid was added as a solution in THF to a stirring slurry of InCl₃ (0.2777 g, 1.255 mmol) in THF (total volume 25 mL) at room temperature. The resulting mixture was stirred at room temperature for 16 hours. The mixture was then filtered and the solution was dried under vacuum to afford a solid which was washed with cold hexanes and dried to obtain complex (R,R-1') as a yellow solid (0.7627 g, yield 83% with respect to rac-H₂(ONNO)).

Figure 1:
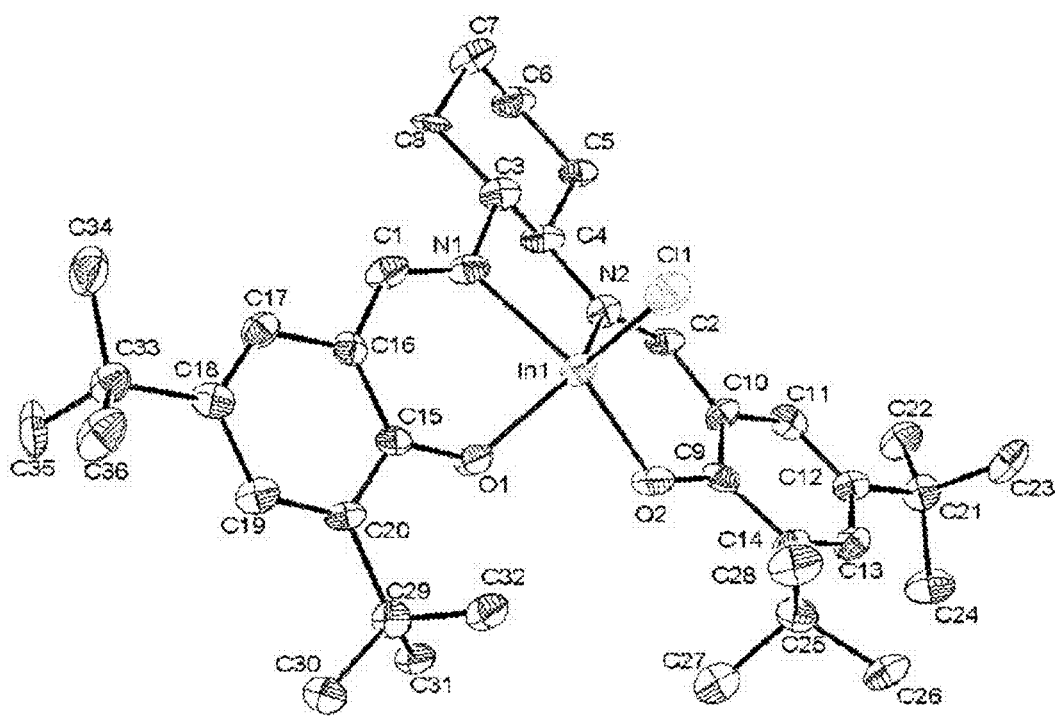
FIG. 1 depicts an ORTEP molecular structure of complex (R,R)—(ONNO)InCl.

$^1$H NMR (300.13 MHz, CDCl₃): δ 8.42 (1H, s, N═CH), 8.21 (1H, s, N═CH), 7.51-7.50 (2H, d, ArH), 6.99 (1H, s, ArH) 6.95 (1H, s, ArH) 3.71-3.64 (1H, m, —CH— of DACH) 3.25-3.17 (1H, m, —CH— of DACH), 2.68-2.64 (1H, m, —CH₂— of DACH), 2.48-24.5 (1H, m, —CH₂— of DACH), 2.11-2.08 (2H, m, —CH₂— of DACH), 1.53-1.43 (4H, m, —CH₂— of DACH) 1.50 (9H, s, Ar—C(CH₃)₃), 1.49 (9H, s, Ar—C(CH₃)₃), 1.31 (9H, s, Ar—C(CH₃)₃), 1.30 (9H, s, Ar—C(CH₃)₃) ppm. $^{13}$C NMR (75.47 MHz, CDCl₃): δ 170.99, 167.75, 167.03, 142.64, 142.57, 137.73, 137.62, 130.62, 129.49, 117.50, 117.30, 65.05, 63.55, 35.68, 33.97, 31.35, 29.51, 28.63, 26.86, 24.21, 23.70. ppm Anal. calcd (found) for C₃₆H₅₂N₂O₂InCl: C, 62.21 (62.36), H, 7.54 (7.45), N, 4.03 (4.04). Yellow coloured X-ray quality crystals were obtained by crystallizing complex (R,R)—(ONNO)InCl in diethyl ether for four days at −30° C. A single crystal of (R,R)—(ONNO)InCl was studied by X-ray crystallography. The ORTEP of the crystal structure of complex (R,R)—(ONNO)InCl is shown in FIG. 1.

Synthesis of indium pyridin-2-ylmethoxide complex (R,R)—(ONNO)InOCH₂Py (R,R-2')

Figure 2:
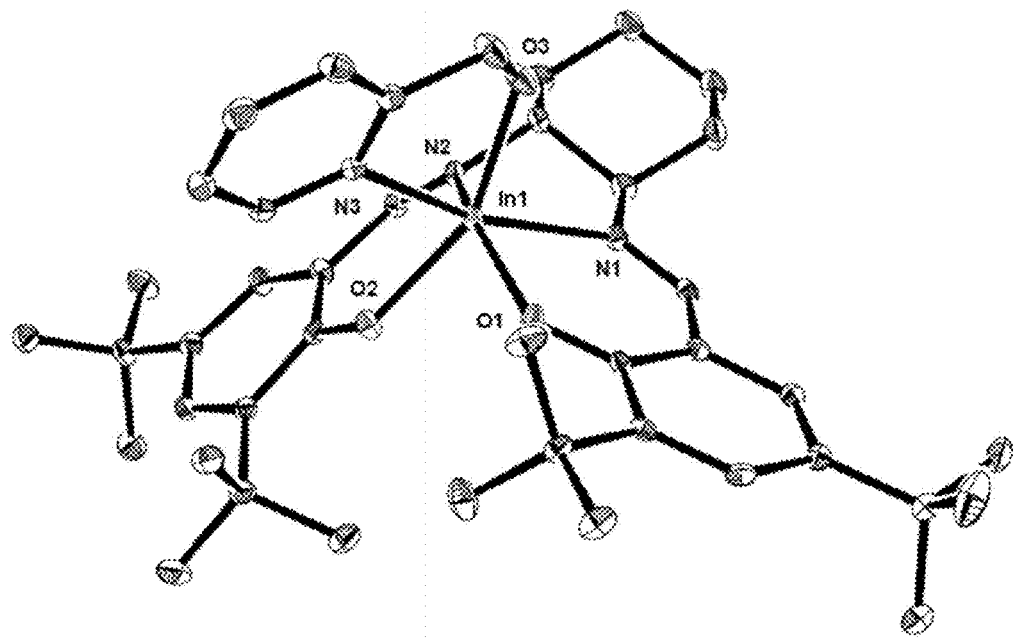
FIG. 2 depicts an ORTEP molecular structure of complex (R,R)-2, with ellipsoids at 50% probability (H atoms have been omitted for clarity)

Complex (R,R)—(ONNO)InCl (R,R-1') was reacted with pyridin-2-ylmethoxide in toluene according to the following scheme:

Complex (R,R-1') (0.124 g, 0.178 mmol) was dissolved in toluene and added to a slurry of potassium pyridin-2-ylmethoxide (0.027 g, 0.183 mmol) in toluene. The mixture was stirred at room temperature for 16 h. The resulting mixture was filtered and the solution evaporated under vacuum to afford a yellow solid (R,R-2'), 0.105 g, 77% yield). Yellow coloured X-ray quality crystals were obtained by crystallizing from hexanes at ambient temperature. $^1$H NMR (600.15 MHz, CDCl₃): δ 8.66-8.65 (1H, d, ArH (pyr)), 8.31 (1H, s, N═CH), 8.14 (1H, s, N═CH), 7.70-7.67 (1H, m, ArH (pyr)), 7.46 (1H, s, ArH), 7.30 (1H, s, ArH), 7.21-7.18 (1H, m, ArH (pyr)), 7.15-7.11 (1H, m, ArH (pyr)), 5.02 (2H, s, —CH₂— of —OCH₂Pyr), 4.29-4.24 (1H, m, —CH— of DACH), 3.03-2.98 (1H, m, —CH— of DACH), 2.54-2.49 (1H, m, —CH₂— of DACH), 2.24-2.21 (1H, m, —CH₂— of DACH), 2.05-1.98 (2H, m, —CH₂— of DACH), 1.74-1.69 (1H, m, —CH₂— of DACH), 1.60-1.56 (2H, m, —CH₂— of DACH), 1.49 (9H, s, Ar—C(CH₃)₃), 1.42-1.35 (1H, nm, —CH₂— of DACH), 1.30 (9H, s, Ar—C(CH₃)₃), 1.27 (9H, s, Ar—C(CH₃)₃), 1.19 (9H, s, Ar—C(CH₃)₃). $^{13}$C NMR (150.91 MHz, CDCl₃): δ 169.10, 168.71, 168.08, 165.47, 164.62, 147.57, 141.18, 141.06, 138.11, 135.43, 135.03, 129.91, 129.26, 128.81, 128.53, 121.82, 121.41, 118.18, 117.76, 67.41, 64.92, 63.95, 35.82, 35.23, 33.05, 31.42, 30.04, 29. 64, 29.28, 27.16, 24.76, 23.84. Anal. calcd (found) for C₄₂H₅₈N₃O₃In: C, 65.71 (66.02), H, 7.61 (7.78), N, 5.47 (5.83). Pulsed-Field Gradient Spin Echo NMR spectroscopy gave a diffusion coefficient of $8.5 \times 10^{-10}$ (3) $m^2 s^{-1}$, which indicates that the complex remains mononuclear in solution. The diffusion coefficient is determined a plot of $\ln(I/I_0)$ vs. $\gamma^2 \delta^2 G^2 [\Delta-(\delta/3)] \times 10^{-10}$ ($m^2$ s) where I=observed spin echo intensity, $I_0$=intensity in the absence of a gradient, G=gradient strength, $\gamma$=gyromagnetic ratio, $\delta$=length of gradient pulse, $\Delta$=delay between gradient midpoints. Methodology based on Macchioni, A.; Ciancaleoni, G.; Zuccaccia, C.; Zuccaccia, D., Chem. Soc. Rev. 2008, 37 (3), 479-489. A more detailed description can be found under supporting information of Yu, I.; Acosta-Ramirez, A.; Mehrkhodavandi, P. J. Am. Chem. Soc. 2012, 134 (30), 12758-12773. ORTEP diagram of complex (R,R)—(ONNO)InOCH$_2$Py (R,R-2') is depicted in FIG. 2. The diagram shows a monomeric indium alkoxide species with the pyridyl nitrogen coordinating to the metal centre. Bond distance for In—$N_{Pyr}$ was 2.296 (2) Å, which is longer than In—$N_{imine}$ bond distances (2.228 (1)-2.258(2) Å).

Synthesis of indium pyridin-2-ylmethoxide complex (R,R)—(ONNO) InOCH$_2$Py (R,R-4')

Complex (R,R)—(ONNO)InCl (R,R-3') was reacted with pyridin-2-ylmethoxide in toluene according to the following scheme:

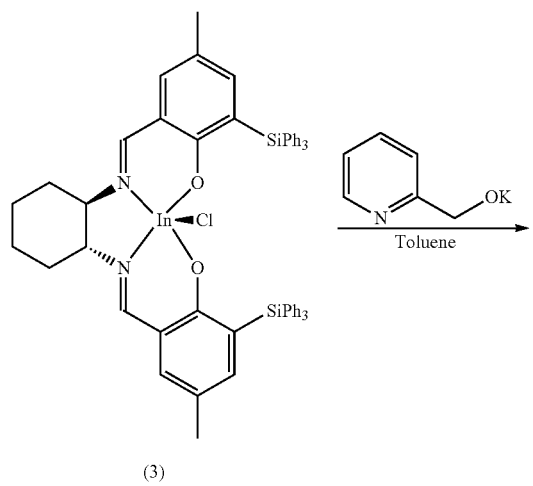

(3)

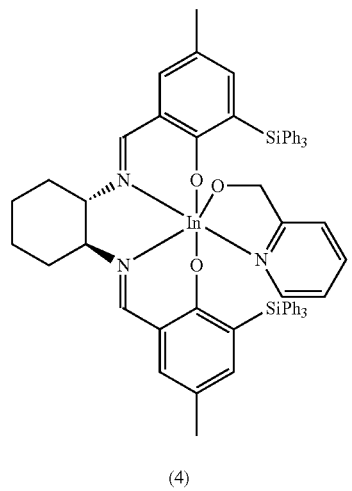

(4)

Ligand (R,R)—(ONNO$_{SiPh3}$)H$_2$ was prepared according to literature procedure (Thadani, A. N.; Huang, Y.; Rawal, V. H. Org. Lett. 2007, 9, 3873). (R,R-3') (0.198 g, 68% yield) was prepared from (R,R)—(ONNO$_{SiPh3}$)H$_2$ (0.250 g, 288 mmol) in an analogous manner to (R,R-1'). $^1$H NMR (400.19 MHz, CDCl$_3$): δ 8.30 (1H, s, N=CH), 8.05 (1H, s, N=CH), 7.80-6.75 (34H, m (multiple, overlapping), 3.69-3.68 (1H, m, —CH— of DACH), 3.10-3.09 (1H, m, —CH— of DACH), 2.47-2.45 (1H, m, —CH$_2$— of DACH), 2.20-2.19 (1H, m, —CH$_2$— of DACH), 2.06-2.03 (2H, n, —CH$_2$— of DACH), 2.12 (3H, s, Ar—CH$_3$), 2.09 (3H, s, Ar—CH$_3$), 1.51-1.45 (4H, m (multiple, overlapping) —CH$_2$— of DACH).

Figure 3:
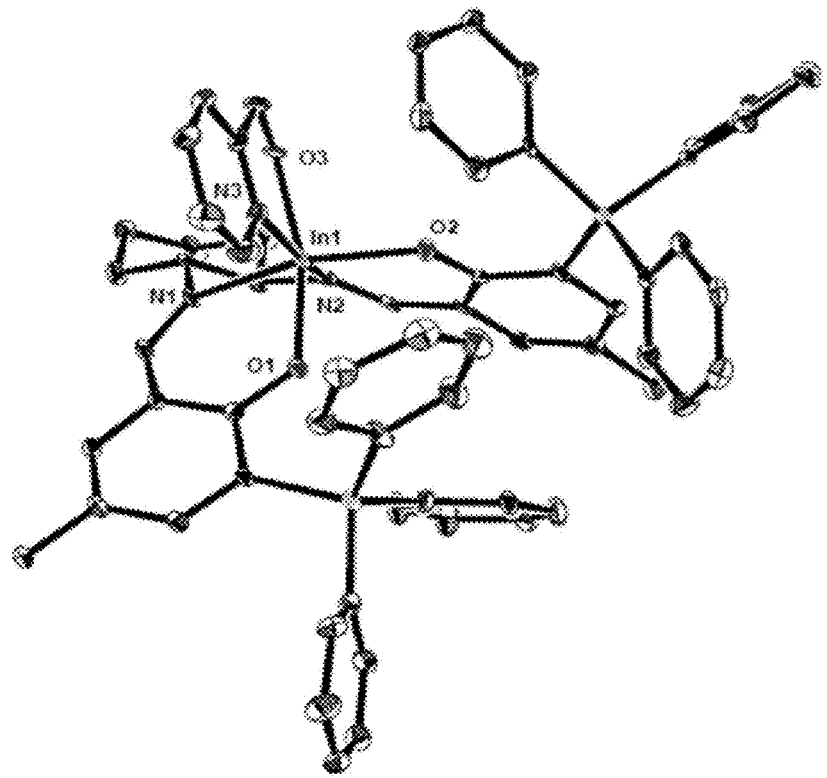
FIG. 3 depicts an ORTEP molecular structure of complex (R,R)—(ONNO)InOCH$_2$Pyr ((R,R)-4), with ellipsoids at 50% probability (H atoms have been omitted for clarity)

Complex (R,R-4') (0.080 g, 73% yield) was prepared in an analogous manner to (R,R-2') from (R,R-3') (0.102 g, 0.100 mmol). Dark orange coloured X-ray quality crystals were obtained by crystallizing from hexanes at ambient temperature. $^1$H NMR (400.19 MHz, CDCl$_3$): δ 8.26 (1H, s, N=CH), 7.94 (1H, s, N=CH), 7.72-6.74 (37H, m (multiple, overlapping), ArH (Ar, SiPh$_3$, and Pyr)), 6.24-6.18 (1H, nm, Ar (Pyr) H) 4.60-4.53 (1H, d, —CH$_2$— of —OCH$_2$Pyr) 4.36-4.34 (1H, m, —CH— of DACH), 4.07-3.99 (1H, d, —CH$_2$— of —OCH$_2$Pyr) 2.90-2.88 (1H, nm, —CH$_2$— of DACH), 2.25-1.45 (8H, m (multiple, overlapping), 2.17 (3H, s, Ar—CH$_3$), 2.05 (3H, s, Ar—CH$_3$). ORETP diagram of complex (R,R)—(ONNO)InOCH$_2$Py (R,R-4') is depicted in FIG. 3.

Ring Opening Polymerization (ROP) of Lactide for GPC and $^1$H{$^1$H} NMR Studies:

All homonuclear decoupled $^1$H NMR spectra were performed on a Bruker Avance 600 MHz spectrometer with a cryoprobe. The $P_m$ and $P_r$ values were calculated from the following formulas which are based on tetrad probabilities in the polymerization of rac-lactide as calculated from Bernoullian statistics. (Chamberlain, B. M.; Cheng, M.; Moore, D. R.; Ovitt, T. M.; Lobkovsky, E. B.; Coates, G. W. J Am. Chem. Soc. 2001, 123, 3229-3238; Bovey, F. A.; Mirau, P. A. NMR of Polymers; Academic Press, San Diego, 1996.)

$$[mmr] = \frac{P_r P_m}{2}$$

$$[rmr] = \frac{P_r^2}{2}$$

where $P_m$ is probability of generating a meso (same) or "m" sequence when a new monomer is added to a polymer, or of finding a meso dyad in an existing polymer, such as observed in isotactic structures;

$P_r$ is the probability of generating a racemic (opposite) or "r" sequence when a new monomer is added to a polymer, or of finding a racemic dyad in an existing polymer, such as observed in syndiotactic structures; and the m and r notations refer to the configuration of one pseudochiral centre relative to its neighbour, where m designates a meso dyad; and r designates a racemic dyad.

The assignment for each tetrad's chemical shift is based on the generally accepted values. (Thakur, K. A. M.; Kean, R. T.; Zell, M. T.; Padden, B. E.; Munson, E. J. Chem. Commun. 1998, 1913-1914.)

In a 20 mL scintillation vial, complex (R,R-2') (5.5 mg, 0.0072 mmol) was dissolved in 1 mL of CH$_2$Cl$_2$; rac-lactide (0.204 g, 1.42 mmol), dissolved in 1.5 mL of CH$_2$Cl$_2$, was added; and, total volume was made to 3 mL. Reaction was allowed to proceed for 4 h, after which time the reaction was quenched with a few drops of HCl in ether. A 0.5 mL sample of the reaction mixture was evaporated under vacuum for 3 hours and was dissolved in CDCl$_3$. $^1$H{$^1$H} NMR spectrum of the mixture's methine region was obtained on a Bruker 600 MHz spectrometer. Thereafter the mixture was evaporated under vacuum and polymer was isolated by washing 3 times with cold methanol. The isolated polymer was subsequently dried under vacuum for 16 h prior to gel permeation chromatography (GPC) analysis. See Table 1.

PLA polymerization rates with indium pyridin-2-yl-methoxide complex (R,R)—(ONNO)InOCH$_2$Py ((R,R-2'):

Polymerizations with (R,R-2') (~2 mM) with 200 eq. of rac-LA were complete in <60 minutes. Kinetic analysis gave a $k_L/k_D$ ratio of ~6. Rate constants ($k_L$ and $k_D$) for the polymerization of L-LA and D-LA with (R,R-2') were determined using in-situ H NMR spectroscopy. A representative experimental procedure is as follows:

All samples for NMR scale polymerization were prepared in Teflon sealed NMR tubes under an N$_2$ atmosphere. The NMR tube was charged with a stock solution of catalyst (R,R-2') in CD$_2$Cl$_2$ (0.25 mL, 0.0011 mmol) and frozen. Then 0.25 mL of CD$_2$Cl$_2$ was added and frozen to create a buffer between the catalyst and lactide monomer. Finally a stock solution with L-lactide (0.50 mL, 0.45 mmol) and internal standard 1,3,5-trimethoxybenzene (5 mg, 0.03 mmol per 0.50 mL) was added and frozen. The sealed and evacuated NMR tube was immediately taken to the NMR spectrometer (400 MHz Avance Bruker Spectrometer) to monitor the polymerization at 25° C.

Resulting polymers had a $P_m$ value of ~0.75. Oligomers show transesterification when probed with MALDI-TOF mass spectrometry, which is desirable for immortal polymerizations. It was noted that this behavior was similar to that of the dimer salen complexes disclosed in PCT application PCT/CA2013/050191; suggesting that both the dimers and the complexes described herein systems have similar propagating species.

PLA polymerization rates with indium pyridin-2-yl-methoxide complex (R,R)—(ONNO)InOCH$_2$Py ((R,R-4'):

Polymerizations with (R,R-4') occurred at a lower rate than (R,R-2') with 200 eq. of rac-LA, requiring 24 h to achieve >90% conversion. Selectivity remained high at $P_m$~0.76.

Example 2

Further Studies into Mononuclear Salen-In Catalysts, and Overcoming aggregation in Salen-In Catalysts for Isoselective Lactide Polymerization A majority of ROP catalysts are comprised of a chelate-supported Lewis acidic metal centre with an alkoxide initiator built in or generated in situ via alcoholysis [O. Dechy-Cabaret, et al., Chem. Rev., 2004, 104, 6147-6176]. Due to the metal center's electrophilicity, and the alkoxide ligands' bridging ability, aggregation is observed in many of these systems [M. P. Blake, et al., Organometallics, 2011, 30, 1202-1214; A. Pietrangelo, et al., J. Am. Chem. Soc., 2010, 132, 11649-11657; S. Dagorne, et al., Coord. Chem. Rev., 2013, 257, 1869-1886]. While aggregation can be beneficial in some cases [A. F. Douglas, et al., Angew. Chem. Int. Ed., 2008, 47, 2290-2293; C. Xu, et al., Chem. Commun., 2012, 48, 6806-6808; I. Yu, et al., J. Am. Chem. Soc, 2012, 134, 12758-12773; D. C. Aluthge, et al., Macromolecules, 2013, 46, 3965-3974; J. Fang, et al., Organometallics, 2013, 32, 6950-6956], in others it can lead to poor control over catalyst speciation and reactivity, as well as polymer macro- and microstructure.

Aggregation can impact polymerization processes by generating competing active species. For asymmetrically-bridged indium systems, previously disclosed in PCT application PCT/CA2012/050331, entitled Catalysts and Methods for Cyclic Ester (Co)Polymerization, and Polymer and Copolymer Products any disturbance of catalyst nuclearity could lead to loss of stereoselectivity and complicates isolation of discrete complexes [K. M. Osten, et al., Dalton Trans., 2012, 41, 8123-8134; K. M. Osten, et al., Inorg. Chem., 2014, 53, 9897-9906; K. M. Osten, et al., Dalton Trans., 2015, 44, 6126-6139]. Similar studies on the role of steric effects on catalyst selectivity of aluminum salen complexes show that these trends may not be entirely predictable [P. Hormnirun, et al., Proc. Natl. Acad. Sci. U.S.A., 2006, 103, 15343-15348]. Further, aggregation phenomena can impact complexes bearing trivalent indium complexes due to their Lewis acidity and large ionic radii [D. C. Aluthge, et al., Inorg. Chem., 2014, 53, 6828-6836].

General Considerations:

Unless otherwise indicated, all air- and/or water-sensitive reactions (synthesis and reactions involving metal complexes) were carried out under dry nitrogen using either an MBraun glove box or standard Schlenk line techniques. Proligands, unless stated otherwise were synthesized without employing air-sensitive techniques.

NMR spectra were recorded on a Bruker Avance 400 MHz or 600 MHz spectrometer. $^1$H NMR chemical shifts are reported in ppm versus residual protons in deuterated chloroform; δ 7.27 CDCl$_3$. $^{13}$C {H} NMR chemical shifts are reported in ppm versus residual $^{13}$C in the solvent; δ 77.2 CDCl$_3$.

Diffraction measurements for X-ray crystallography were made on a Bruker APEX DUO diffractometer with graphite monochromated Mo-Kα radiation. The structures (Table 2) were solved by direct methods and refined by full-matrix least-squares using the SHELXTL crystallographic software of Bruker-AXS. Unless specified, all non-hydrogen atoms were refined with anisotropic displacement parameters, and all hydrogen atoms were constrained to geometrically calculated positions but were not refined.

Elemental analysis (C, H, and N) was performed using a Carlo Erba EA1108 elemental analyzer. The elemental composition of unknown samples was determined by using a calibration factor. The calibration factor was determined by analyzing a suitable certified organic standard (OAS) of a known elemental composition.

Molecular weights were determined by triple detection gel permeation chromatography (GPC-LLS) using a Waters liquid chromatograph equipped with a Water 515 HPLC pump, Waters 717 plus autosampler, Waters Styragel columns (4.6×300 mm) HR5E, HR4 and HR2, Water 2410 differential refractometer, Wyatt tristar miniDAWN (laser light scattering detector) and a Wyatt ViscoStar viscometer. A flow rate of 0.5 mL min$^1$ was used and samples were dissolved in THF (2 mg mL$^{-1}$). Narrow molecular weight polystyrene standards were used for calibration purposes. The molar mass was calculated with ASTRA© 5 software using the Mark-Houwink parameters, laser light scattering detector data, and concentration detector. Distribution and moment procedures of ASTRA© 5 was used to calculate molar mass moments $M_n$, $M_w$ and $M_z$.

Differential scanning calorimetry (DSC) was carried out using a Shimadzu DSC 60 calorimeter.

Materials:

Solvents (tetrahydrofuran, toluene, hexanes and diethyl ether) were collected from an MBraun solvent purification system whose columns are packed with activated alumina. $CD_2Cl_2$, $CDCl_3$, ethyl acetate, and pyridine were dried over $CaH_2$, and degassed through a series of three freeze-pump-thaw cycles.

Where dry solvents were not required (i.e. ligand synthesis) solvents were used as received from the manufacturer. 1,3,5-Trimethoxybenzene, tetrakis(trimethylsilyl) silane, KOtBu, and NaOEt were purchased from Aldrich and used as received after drying overnight under vacuum. $InCl_3$ was purchased from Strem chemicals and used as received. (±)/(R,R)-1 and (±)/(R,R)-6 [M. Osten, et aL, Dalton Trans., 2012, 41, 8123-8134; K. M. Osten, et al., Inorg. Chem., 2014, 53, 9897-9906; K. M. Osten, el al., Dalton Trans., 2015, 44, 6126-6139] as well as (R,R)—$H_2(ONNO_{Br})$ [X. Q. Yao, et aL, Tetrahedron: Asymmetry, 2001, 12, 197-204], (R,R)—$H_2(ONNO_{Me})$ [V. Rudzevich, et al.,J. Org. Chem., 2005, 70, 6027-6033], (R,R)—$H_2(ONNO_{Cm})$ [C. T. Cohen, et al., Dalton Trans., 2006, 237-249], and $KCH_2Ph$ [M. Schlosser, in Organometallics in Synthesis: A Manual, 2nd ed. (Ed.: M. Schlosser), Wiley, Chichester, 2002, p. 262] were synthesized according to previously reported procedures. Racemic, D, L-lactide were a gift from PURAC America Inc. and recrystallized twice from hot dried toluene.

Synthesis of Proligands and Indium Chloride Complexes

Proligands

Figure 4:
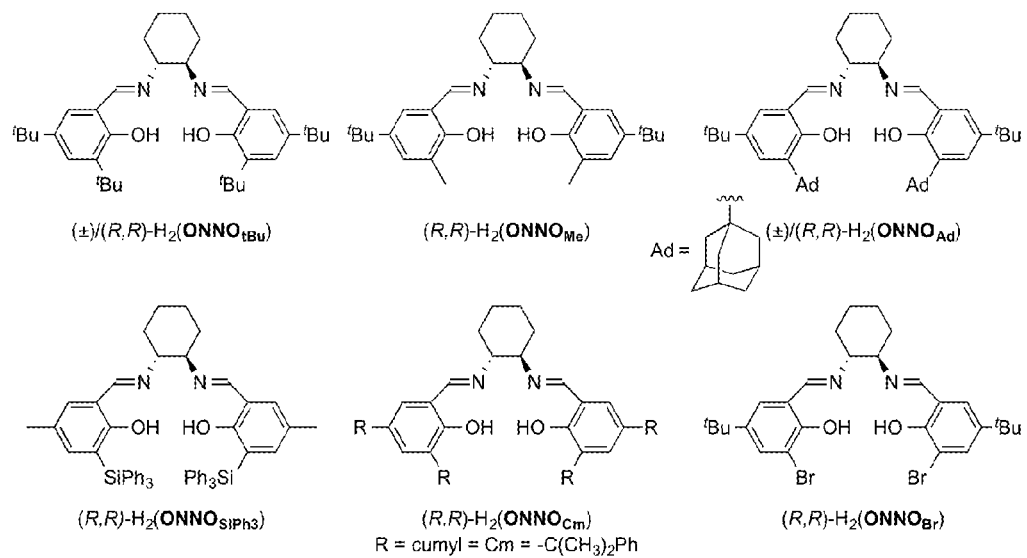
FIG. 4 depicts enantiopure and racemic H$_2$(ONNOR) proligands: R=t-Bu, Br, Me, Cm, Ad and SiPh$_3$.

A series of tetradentate Schiff base salen ligands, (±)- or (R,R)—$H_2(ONNO_R)$, with various ortho-phenolate groups (R) were synthesized by treating mono-(+)-tartrate salts of (±)-1,2-diaminocyclohexane or (R,R)— 1,2-diammonium-cyclohexane with two equivalents of a corresponding salicylaldehydes under basic conditions (FIG. 4) [E. N. Jacobsen, et al., J. Am. Chem. Soc., 1991, 113, 6703-6704; X. Q. Yao, et al., Tetrahedron: Asymmetry, 2001, 12, 197-204; V. Rudzevich, et al., J. Org. Chem., 2005, 70, 6027-6033; C. T. Cohen, et al., Dalton Trans., 2006, 237-249]. $^1$H NMR spectra ($CDCl_3$, 25° C.) of all proligands showed one characteristic singlet between 8-9 ppm, which corresponded to two equivalent N=CH resonances. In corresponding $^{13}C\{^1H\}$ spectra, N=CH resonances appear at >160 ppm.

Synthesis of (R,R)—$H_2(ONNO_{Ad})$

A 250 mL round-bottom flask was charged with a teflon stir bar, (R,R)-1,2-diammoniumcyclohexane mono-(+)-tartrate (0.390 g, 1.48 mmol) and anhydrous $K_2CO_3$ (0.102 g, 0.739 mmol). To this mixture 15 mL of water was added and stirred until complete dissolution was achieved. 3-Adamantan-1-yl-5-tert-butyl-2-hydroxybenzaldehyde (0.920 g, 294 mmol) was suspended in 50 mL of ethanol in a 250 mL Erlenmeyer flask. This was stirred and $CH_2Cl_2$ was added drop-wise until complete dissolution of the salicylaldehyde was achieved. This solution was then added at once to the stirring aqueous solution in the 250 mL round-bottom flask. Upon mixing a bright yellow solution was observed immediately. A reflux condenser was attached to the round bottom flask and the reaction was heated to reflux (~90° C.) and allowed to stir for 4 h. The reaction was then allowed to cool down to room temperature and reaction was concentrated using rotary evaporation until volume decreased by ~25%. This mixture was then cooled down to ~5° C. in a refrigerator for 30 minutes and filtered using suction filtration. A bright yellow solid isolated was repeatedly washed with water. The solid was then dissolved in 25 mL of $CH_2Cl_2$ and washed successively with two 25 mL portions of water and 25 mL of a saturated NaCl solution. The organic phase was subsequently dried over anhydrous $MgSO_4$, filtered and solvent was removed using rotary evaporation to yield a yellow powder. This was left under dynamic vacuum overnight prior to use (yield: 0.960 g, 93%). $^1$H NMR (400 MHz, $CDCl_3$, 25° C.): δ 8.30 (2H, s, N=CH), 7.25 (2H, s, ArH), 6.98 (2H, s, ArH), 3.35-3.30 (2H, s, —CH— of DACH), 2.16 (12H, br s, —$CH_2$— of Ad), 2.08 (6H, br s, —CH— of Ad), 1.80 (12H, br s, —$CH_2$— of Ad), 1.92-1.30 (8H, overlapping m, —$CH_2$— of DACH), 1.24 (18 H, br s, Ar—$C(CH_3)_3$). $^{13}$C NMR (100.63 MHz, $CDCl_3$, 25° C.): δ 166.0, 158.2, 139.9, 136.6, 126.7, 126.0, 117.8, 72.4, 40.3, 37.2, 34.1, 33.3, 31.4, 29.1, 24.4. Anal. calcd (found) for $C_{48}H_{66}N_2O_2$: 82.00 (81.42), H, 9.68 (9.46), N, 3.98 (3.60).

Synthesis of (±)-$H_2(ONNO_{Ad})$

Racemic ligand was prepared and purified in an analogous manner to (±)-$H_2(ONNO_{tBu})$ [E. N. Jacobsen, et al., J. Am. Chem. Soc., 1991, 113, 6703-6704] from (±)-1,2-diaminocyclohexane (0.055 g, 0.48 mmol) and 3-adamantan-1-yl-5-tert-butyl-2-hydroxybenzaldehyde (0.300 g, 9.6 mmol) (yield: 0.210 g, 62%). The ligand had an NMR signature similar to that of (R,R)— $H_2(ONNO_{Ad})$. Anal. calcd (found) for $C_{48}H_{66}N_2O_2$: C, 82.00 (82.20), H, 9.68 (9.53), N, 3.98 (3.00).

Synthesis of (R,R)—$H_2(ONNO_{SiPh3})$

This was synthesized in a manner analogous to (R,R)—$H_2(ONNO_{Ad})$ from (R,R)-1,2-diammoniumcyclohexane mono-(+)-tartrate (0.044 g, 0.16 mmol) and 3-triphenylsilyl-5-methyl-2-hydroxybenzaldehyde (0.130 g, 0.33 mmol), and isolated as a yellow solid (yield: 0.126 g, 88%). $^1$H NMR (400 MHz, $CDCl_3$, 25° C.): δ 8.13 (2H, s, N=CH), 7.25 (2H, s, ArH), 7.62-6.92 (34H, overlapping m, —$SiPh_3$, ArH), 3.24-3.18 (2H, s, —CH— of DACH), 2.18 (6H, s, $ArCH_3$), 1.93-1.75 (4H, overlapping m, —$CH_2$— of DACH), 1.73-1.51 (2H, m, —$CH_2$—), 1.49-1.25 (2H, m, —$CH_2$—). $^{13}C\{^1H\}$ NMR (100.63 MHz, $CDCl_3$, 25° C.): δ 164.6, 164.0, 141.8, 136.3, 134.8, 134.2, 129.2, 127.6, 127.2, 121.0, 117.7, 72.8, 33.0, 24.2, 20.4. Anal. calcd (found) for $C_{58}H_{54}N_2O_2Si_2$: C, 80.33 (79.74), H, 6.28 (6.03), N, 3.28 (3.16).

Figure 5:
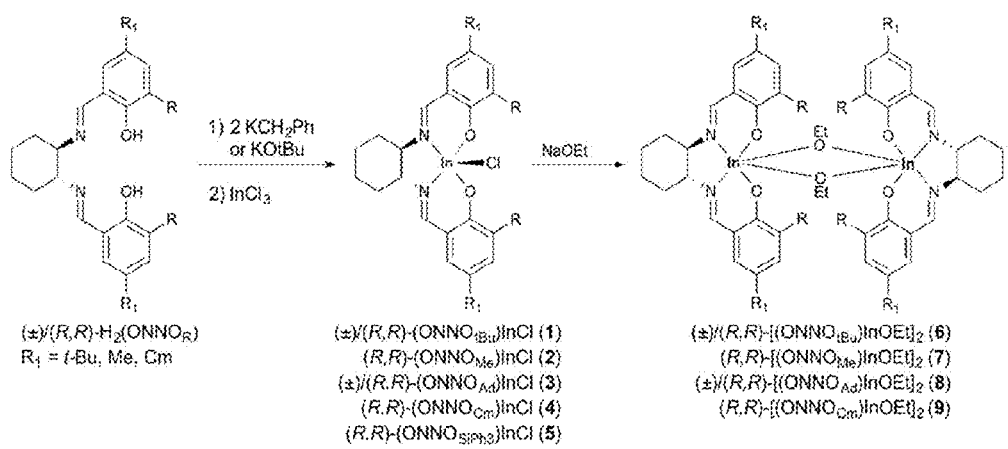
FIG. 5 depicts general synthesis of Salen-In complexes 1-9.

In Chloride Complexes:

Metallation reactions were ligand dependent, and could be carried out via two routes. The first route involved deprotonation of the proligands followed by salt metathesis with an appropriate indium trihalide compound, as reported for (±)/(R,R)-1 previously [D. C. Aluthge, et al., Chem. Commun., 2013, 49, 4295-4297]. Deprotonation of (±)/(R,R)—$H_2(ONNO_R)$ with two equiv of $KCH_2Ph$ or KOt-Bu, followed by addition of one equiv of $InCl_3$, yielded the respective racemic or enantiopure indium chloride derivatives (±)/(R,R)—$(ONNO_R)$InCl (R=t-Bu 1, Me 2, Ad 3, Cm 4, $SiPh_3$ 5) (FIG. 5). However, similar reactions with (R,R)—$H_2(ONNO_{Br})$ formed intractable mixtures, necessitating a different synthetic route towards alkoxide complexes (see below). $^1$H NMR spectra of complexes (±)/(R, R)-1-5 showed two singlet resonances corresponding to the N=CH group between 8-9 ppm, indicative of loss of $C_2$ rotational axis of the ligand after metallation. $^1$H NMR spectra of the racemic complexes were identical to their enantiopure analogues.

The solid state structures of (±)-1 [D. C. Aluthge, et al., *Chem. Commun.*, 2013, 49, 4295-4297] and (±)-3 (FIG. 6), determined by single crystal X-ray crystallography, contained five-coordinate indium centers with distorted square pyramidal geometries. In contrast, structure of (R,R)-2.CH$_3$CN, obtained in acetonitrile, had a distorted octahedral geometry with an acetonitrile molecule coordinating to the indium trans to the chloride (FIG. 7). The In—Cl distance in (R,R)-2.CH$_3$CN (Å) is longer than the In—Cl bond distances in either (±)-1 or (±)-3 (2.470(1), 2.371(2) and 2.3704(7) Å for 2.CH$_3$CN, 1, and 3 respectively), and could be attributed to a trans influence from the coordinating acetonitrile.

Synthesis of (R,R)—(ONNO$_{Me}$)InCl (R,R)-2

Complex (R,R)-2 was prepared and purified in an analogous manner to (R,R)-1 from (R,R)—H$_2$(ONNO$_{Me}$) (0.400 g, 0.86 mmol) as a yellow solid (yield: 0.432 g, 82%). X-ray quality crystals were grown by slow evaporation in acetonitrile. $^1$H NMR (600 MHz, CDCl3, 25° C.): δ 8.36 (1H, s, N=CH), 8.18 (1H, s, N=CH), 7.34 (2H, s, ArH), 6.95 (1H, s, ArH), 6.90 (1H, s, ArH), 3.70-3.66 (1H, m, —CH—), 3.11-3.08 (1H, m, —CH—), 2.61-2.57 (1H, m, —CH$_2$—), 2.48-3.44 (1H, m, —CH$_2$—), 2.30 (6H, s, Ar—CH$_3$), 2.09-2.06 (2H, m, —CH$_2$—), 1.57-1.41 (m, 4H, —CH$_2$—), 1.28 (18H, br s, Ar—C(CH$_3$)$_3$). $^{13}$C{$^1$H} NMR (151 MHz, CDCl$_3$, 25° C.): δ 170.6, 167.0, 166.7, 138.5, 138.3, 134.3, 133.9, 132.1, 129.1, 125.7, 116.5, 116.3, 65.2, 63.4, 33.8, 31.5, 31.5, 31.5, 27.2, 24.3, 23.9, 17.2, 17.2, 2.1. Anal. Calcd (found) for C$_{30}$H$_{40}$ClInN$_2$O$_2$: C, 59.98 (59.71); H, 6.60 (6.74); N, 4.59 (4.84).

Synthesis of (R,R)—(ONNO$_{Ad}$)InCl (R,R)-3

Complex (R,R)-3 was prepared and purified in an analogous manner (R,R)-1 from (R,R)—H$_2$(ONNO$_{Ad}$) (0.103 g, 0.146 mmol) as a yellow solid (yield: 0.099 g, 79%). $^1$H NMR (600 MHz, CDCl$_3$, 25° C.): δ 8.43 (1H, s, N=CH), 8.18 (1H, s, N=CH), 7.45 (2H, s, ArH), 6.98 (1H, s, ArH), 6.92 (1H, s, ArH), 3.64-3.60 (1H, m, —CH— of DACH), 3.24-3.20 (1H, m, —CH— of DACH), 2.64-2.61 (1H, m, —CH$_2$— of DACH), 2.48-2.44 (1H, m, —CH$_2$— of DACH), 2.26-2.24 (12H, d (J$^3$=6.0 Hz), —CH$_2$— of Ad), 2.16-1.69 (20H, overlapping —CH— and —CH$_2$— resonances of Ad and DACH), 1.52-1.42 (m, 4H, —CH$_2$— of DACH), 1.31 (18H, br s, Ar—C(CH$_3$)$_3$). $^{13}$C{$^1$H} NMR (151 MHz, CDCl$_3$, 25° C.): δ 171.9, 168.6, 167.8, 166.7, 142.6, 137.9, 137.9, 131.0, 130.5, 129.8, 129.6, 117.5, 68.0, 64.9, 63.2, 40.6, 40.5, 37.3, 37.2, 34.0, 31.3, 29.1, 27.0, 25.3, 24.2, 23.6. Anal. Calcd (found) for C$_{48}$H$_{64}$ClInN$_2$O$_2$: C, 67.72 (67.79); H, 7.58 (7.75); N, 3.29 (3.17).

Synthesis of (±)-(ONNO$_{Ad}$)InCl (±)-3

Racemic complex (±)-3 was prepared and purified in an analogous manner to (R,R)-1 from (±)-H$_2$(ONNO$_{Ad}$) (0.060 g, 0.085 mmol) as a yellow solid (yield: 0.054 g, 74%). X-ray quality single crystals were obtained by crystallizing in diethyl ether for four days at −30° C. The complex had an identical NMR signature to that of (R,R)-3. Anal. calcd (found) for C$_{48}$H$_{64}$ClInN$_2$O$_2$: C, 67.72 (67.62); H, 7.58 (7.44); N, 3.29 (3.51).

Synthesis of (R,R)—(ONNO$_{Cm}$)InCl (R,R)-4

Complex (R,R)-4 was prepared and purified in an analogous manner to (R,R)-1 from (R,R)—H$_2$(ONNO$_{Cm}$) (0.482 g, 0.606 mmol) as a yellow solid (yield: 0.423 g, 74%). $^1$H NMR (600 MHz, CDCl$_3$, 25° C.): δ 8.23 (1H, s, N=CH), 8.02 (1H, s, N=CH), 7.32-7.15 (20H, overlapping peaks, ArH), 7.10 (2H, s, ArH), 6.88 (1H, s, ArH), 6.85 (1H, s, ArH), 3.49-3.46 (1H, m, —CH—), 3.09-3.06 (1H, m, —CH—), 2.53-2.49 (1H, m, —CH$_2$—), 2.34-2.31 (1H, m, —CH$_2$—), 2.04-2.00 (2H, m, —CH$_2$—), 1.76 (3H, s, —CH$_3$), 1.76 (3H, br s, —CH$_3$), 1.75 (3H, br s, —CH$_3$), 1.72 (3H, br s, —CH$_3$), 1.70 (3H, br s, —CH$_3$), 1.64 (12H, br s, —CH$_3$), 1.41-1.37 (4H, n, —CH$_2$—). $^{13}$C{$^1$H} NMR (151 MHz, CDCl$_3$, 25° C.): δ 170.5, 166.7, 150.7, 150.6, 133.1, 132.8, 131.5, 128.0, 126.7, 126.7, 126.0, 125.6, 124.9, 124.8, 65.9, 63.1, 42.9, 42.2, 31.0, 30.8, 30.7, 29.4, 28.2, 26.9, 24.1, 23.6, 15.3. Anal. calcd (found) for C$_{56}$H$_{60}$ClInN$_2$O$_2$: C, 71.30 (70.94); H, 6.41 (6.78); N, 2.97 (3.18).

Synthesis of (R,R)—(ONNO$_{SiPh3}$)InCl (R,R)-5

Complex (R,R)-5 was prepared and purified in an analogous manner to (R,R)-1 from (R,R)—H$_2$(ONNO$_{SiPh3}$) (0.148 g, 0.171 mmol) as a yellow solid (yield: 0.139 g, 80%). $^1$H NMR (600 MHz, CDCl$_3$, 25° C.): δ 8.30 (1H, s, N=CH), 8.06 (1H, s, N=CH), 7.40-6.98 (H, overlapping peaks, ArH), 3.70-3.64 (1H, m, —CH—), 3.13-3.11 (1H, m, —CH—), 2.45-2.41 (1H, m, —CH$_2$—), 2.40-2.35 (1H, m, —CH$_2$—), 2.11 (3H, s, ArCH$_3$), 2.09 (3H, s, ArCH$_3$), 2.06-2.02 (2H, m, —CH$_2$—), 2.01 (2H, m, —CH$_2$—), 1.53-1.40 (m, 4H, —CH$_2$—). $^{13}$C{$^1$H} NMR (151 MHz, CDCl$_3$, 25° C.): δ 165.7, 147.4, 136.2, 136.1, 135.9, 134.6, 129.5, 128.2, 127.7, 121.5, 126.9, 126.9, 67.8, 62.4, 51.4, 30.7, 25.0, 23.2, 21.1, 20.2, 19.5. Anal. calcd (found) for C$_{58}$H$_{62}$ClInN$_2$O$_2$Si$_2$: C, 68.60 (68.25); H, 5.16 (5.42); N, 2.76 (2.10).

Synthesis of Dimeric Ethoxide-bridged Salen-In Complexes Using Salt Metathesis

Salt metathesis reaction of complex 1 with limited amounts of NaOEt to yield (±)/(R,R)—[(ONNO$_{tBu}$)InOEt]$_2$ (6) was previously reported [D. C. Aluthge, et al., *Chem. Commun.*, 2013, 49, 4295-4297]. This methodology was extended to complexes (R,R)-2-4, to generate (R,R)-7-9, respectively (FIG. 5). However, a similar reaction with SiPh$_3$-substituted (R,R)-5 generated an intractable mixture of products. $^1$H NMR spectra of complexes (R,R)-7-9 showed two characteristic C=NH resonances, similar to those observed for the (ONNO$_R$)InCl complexes. Compounds (R,R)-6-8 contained two diastereotopic multiplet resonances for the —OCH$_2$CH$_3$ protons between 3-4 ppm, while in the spectrum of (R,R)-9, perhaps as a result of increased steric hinderance, these methylene protons appeared as a quartet at 3.51 ppm.

Solid state molecular structure of (R,R)-7, determined by single crystals X-ray crystallography, was analogous to that of complex (±)-6 (FIG. 8) [D. C. Aluthge, et al., *Chem. Commun.*, 2013, 49, 4295-4297]. Both complexes were dimeric, with distorted octahedral geometries around the indium centres and comparable bond lengths and angles. A difference between structures of complexes 6 and 7 was a distortion in the salen ligand despite its rigid cyclohexyl backbone. While 6-coordinate dimeric [(salen)Al(OR)]$_2$ complexes are known [D. A. Atwood, et al., *Inorg. Chem.*, 1996, 35, 63-70; T. M. Ovitt and G. W. Coates, *J. Am. Chem. Soc.*, 2002, 124, 1316-1326], a most common coordination number for salen aluminum alkoxide complexes is five [M. H. Chisholm, et al., *Chem. Commun.*, 2005, 127-129; D. A. Atwood and M. J. Harvey, *Chem. Rev.*, 2001, 101, 37-52]. In contrast, the larger ionic radius of In(III) could render indium alkoxide complexes prone to aggregation and formation of dimeric [(κ⁴-ligand)In(OR)]2 complexes, such as those previously reported [D. C. Aluthge, et al., *Inorg. Chem.*, 2014, 53, 6828-6836; I. Peckermann, et al., *Inorg. Chem.*, 2009, 48, 5526-5534; D. A. Atwood and M. J. Harvey, *Chem. Rev.*, 2001, 101, 37-52; D. A. Atwood, et al., *Bull. Chem. Soc. Jpn.*, 1997, 70, 2093-2100; M. S. Hill and D. A. Atwood, *Main Group Chem.*, 1998, 2, 191-202].

Synthesis of Dimeric Ethoxide-bridged Indium Complexes Using a One-pot Procedure While the salt metathesis methodology described above works well with many ligands, it was not applicable to systems such as (R,R)—H$_2$(ONNO$_{Br}$) where isolation of the indium chloride complex was challenging. In order to access these indium alkoxide complexes, a one-pot strategy wase used (FIG. 9) [A. F. Douglas, et al., *Angew. Chem. Int. Ed.*, 2008, 47, 2290-2293]. Stirring the H$_2$(ONNO$_R$) proligands with InCl$_3$ formed preliminary adducts, which reacted with excess NaOEt to form the desired products (FIG. 9) [$^1$H NMR spectra of incomplete reactions, after addition of NaOEt, showed resonances corresponding to respective characterized (ONNO$_R$)InCl complexes, indicating their synthesis as an intermediate species]. This milder procedure generated complexes (R,R)-6-10 from their respective proligands in 50-70% yields.

One-pot Synthesis of (R,R)—[(ONNO$_{Me}$)InOEt]$_2$ (R,R)-7 (Representative procedure)

A 20 mL scintillation vial was charged with proligand (R,R)—H$_2$(ONNO$_{Me}$) (0.100 g, 0.216 mmol), InCl$_3$ (0.048 g, 0.216 mmol), 3 mL toluene, and a magnetic stir bar. The mixture was stirred for 30 minutes and a suspension of 6 equiv. NaOEt (0.088 mg, 1.3 mmol) in 4 mL of toluene was added to the reaction. The mixture was allowed to stir at room temperature overnight, and filtered using glass filter paper. Solvent was removed under vacuum to yield a yellow solid (0.087 g, 65%). Salt metathesis of (R,R)-2 (0.110 g, 0.180 mmol), analogous to synthesis of (R,R)-6, was also used in the synthesis of this complex (yield: 0.088 g, 78%). $^1$H NMR (600 MHz, CDCl$_3$, 25° C.): δ 8.22 (1H, s, N═CH), 7.97 (1H, m, N═CH), 7.27 (1H, s, ArH), 7.21 (1H, s, ArH), 6.85 (1H, s, ArH), 6.78 (1H, s, ArH), 3.62 (1H, m, —CH$_2$), 3.37-3.28 (2H, m, —CH$_2$— of —OCH$_2$CH$_3$), 2.82-2.79 (1H, m, —CH—), 2.26 (3H, s, ArCH$_3$), 2.14 (3H, m, ArCH$_3$), 1.93-1.91 (1H, —CH$_2$—), 1.85-1.83 (1H, m, —CH$_2$—), 1.77 (1H, —CH$_2$—), 1.44-1.42 (1H, m, —CH$_2$—), 1.33-1.20 (3H, m, —CH$_2$—) 1.32 (3H, t (J=6.7 Hz), —OCH$_2$CH$_3$), 1.27 (9H, s, ArC(CH$_3$)$_3$), 1.27 (9H, s, ArC(CH$_3$)$_3$), 1.07-1.03 (1H, m, —CH$_2$—). $^{13}$C{$^1$H} NMR (151 MHz, CDCl$_3$, 25° C.): δ 170.5, 168.2, 167.3, 163.0, 135.9, 135.7, 132.7, 132.2, 131.7, 131.6, 129.2, 128.6, 128.4, 126.9, 125.4, 117.6, 116.4, 68.5, 62.8, 59.9, 33.7, 31.6, 31.6, 27.2, 24.8, 24.7, 20.6, 17.8, 17.2. Anal. Calcd (found) for C$_{32}$H$_{45}$InN$_2$O$_3$: C, 61.94 (61.33); H, 7.31 (7.36); N, 4.51 (4.54).

Synthesis of (R,R)—[(ONNO$_{Ad}$)InOEt]$_2$ (R,R)-8

(R,R)-8 was synthesized via the salt metathesis of (R,R)-3 (0.182 g, 0.214 mmol) (analogous to the synthesis of (R,R)-6) as a yellow solid (yield: 0.142 g, 77%) and the one pot synthesis (analogous to the one-pot synthesis of (R,R)-7) with (R,R)—H$_2$(ONNO$_{Ad}$) (0.141 g, 0.200 mmol) (yield: 0.097 g, 56%). $^1$H NMR (600 MHz, CDCl$_3$, 25° C.): δ 8.13 (1H, s, N═CH), 8.03 (1H, m, N═CH), 7.43 (1H, s, ArH), 7.31 (1H, s, ArH), 6.90 (1H, s, ArH), 6.78 (1H, s, ArH), 3.88-3.77 (1H, m, —CH—), 3.76-3.61 (2H, m, —CH$_2$— of —OCH$_2$CH$_3$), 2.74-2.68 (1H, m, —CH—), 2.36-1.15 (38H overlapping signals Ad and —CH$_2$— of DACH), 1.31 (9H, s, Ar (CH$_3$)$_3$), 1.27 (9H, s, ArC(CH$_3$)$_3$), 1.07 (3H, t (J$^3$=6.3 Hz), —OCH$_2$CH$_3$). $^{13}$C {H}NMR (151 MHz, CDCl$_3$, 25° C.): δ 171.6, 169.3, 168.7, 162.5, 142.3, 141.8, 135.7, 134.5, 130.0, 129.5, 129.0, 128.2, 127.8, 125.3, 118.1, 118.0, 69.8, 62.6, 60.3, 40.6, 40.4, 37.2, 37.1, 33.9, 31.3, 29.1, 27.5, 24.7, 20.7. Anal. calcd (found) for C$_{50}$H$_{69}$InN$_2$O$_3$: C, 69.76 (70.07); H, 8.08 (7.95); N, 3.39 (3.42).

Synthesis of (R,R)—[(ONNO$_{Cm}$)InOEt]$_2$ (R,R)-9

(R,R)-9 was synthesized via the salt metathesis (analogous to the synthesis of (R,R)-6) of (R,R)-4 (0.338 g, 0.358 mmol) as a yellow solid (yield: 0.256 g, 75%) and the one pot synthesis with (R,R)—H$_2$(ONNO$_{cumyl}$) (0.266 g, 0.335 mmol)(yield: 0.189 g, 59%). $^1$H NMR (400 MHz, CDCl$_3$, 25° C.): δ 7.86 (1H, s, N═CH), 7.82 (1H, m, N═CH), 7.38-7.34 (2H, m, ArH), 7.28-7.05 (14H, overlapping signals, ArH), 6.98-6.94 (2H, m, ArH), 6.71 (1H, s, ArH), 6.70-6.64 (2H, m, ArH), 6.62 (1H, s, ArH), 6.54-6.50 (2H, m, ArH), 3.81-3.73 (1H, m, —CH—), 3.51 (2H, q, —CH$_2$— of —OCH$_2$CH$_3$), 2.46-2.42 (1H, m, —CH—), 2.13 (3H, s, —CH$_3$), 2.05-2.01 (1H, m, —CH$_2$—), 1.93 (3H, s, —CH$_3$), 1.88-1.83 (1H, m, —CH$_2$—), 1.70 (3H, s, —CH$_3$), 1.64 (3H, s, —CH$_3$), 1.64 (3H, s, —CH$_3$), 1.51 (3H, s, —CH$_3$), 1.50 (3H, s, —CH$_3$), 1.45 (3H, s, —CH$_3$) 1.75-1.19 (6H, overlapping signals —CH$_2$— of DACH), 1.09 (3H, t (J$^3$=3.2 Hz), —OCH$_2$CH$_3$). $^{13}$C{$^1$H} NMR (151 MHz, CDCl$_3$, 25° C.): δ 171.4, 168.5, 167.7, 161.8, 151.6, 151.2, 150.7, 150.2, 141.8, 141.6, 134.7, 133.7, 131.6, 131.5, 129.4, 127.8, 127.8, 126.6, 126.5, 125.2, 123.6, 118.2, 118.0, 68.9, 62.6, 59.3, 44.2, 42.2, 42.0, 41.7, 31.6, 30.9, 30.7, 30.4, 27.7, 26.4, 24.5, 24.4, 21.1. Anal. calcd (found) for C$_{58}$H$_{65}$InN$_2$O$_3$: C, 73.10 (72.92); H, 6.88 (6.49); N, 2.94 (2.83).

Synthesis of (R,R)—[(ONN$_{Br}$O$_{tBu}$)InOEt]$_2$ (R,R)-10

(R,R)-10 was synthesized using the one pot synthesis with (R,R)—H$_2$(ONNO$_{Br}$) (0.204 g, 0.344 mmol) as a yellow solid (0.178 g, 69%). $^1$H NMR (400 MHz, CDCl$_3$, 25° C.): δ 8.23 (1H, s, N═CH), 7.94 (1H, m, N═CH), 7.72 (1H, s, ArH), 7.68 (1H, s, ArH), 7.01 (1H, s, ArH), 6.91 (1H, s, ArH), 3.67-3.65 (1H, m, —CH$_2$—), 3.66-3.41 (2H, m, —CH$_2$— of —OCH$_2$CH$_3$), 2.89-2.85 (1H, m, —CH—), 2.33-2.29 (1H, —CH$_2$—), 1.89-1.83 (3H, m, —CH$_2$—), 1.50-1.19 (4H, overlapping peaks, —CH$_2$—), 1.48 (3H, t (J$^3$=3.6 Hz), —OCH$_2$CH$_3$), 1.29 (9H, s, ArC(CH$_3$)$_3$), 1.26 (9H, s, ArC(CH$_3$)$_3$). $^{13}$C{$^1$H} NMR (151 MHz, CDCl$_3$, 25° C.): δ 170.4, 164.2, 163.6, 162.8, 137.7, 137.4, 135.3, 130.7, 128.9, 128.2, 119.3, 118.8, 118.4, 117.7, 68.5, 62.8, 60.7, 33.7, 31.3, 31.0, 28.1, 24.5, 24.4, 20.8. Anal. calcd (found) for C$_{30}$H$_{39}$Br$_2$InN$_2$O$_3$: C, 48.03 (48.39); H, 5.24 (5.16); N, 3.73 (3.73).

Synthesis of Mononuclear Indium Salen Alkoxide Complexes

Indium salen alkoxide complexes bearing bulkier —SiPh$_3$ group cannot be synthesized using either of the above described strategies. It was hypothesized that dimerization of indium alkoxide complexes was a necessary thermodynamic minimum, which prevented further aggregation and facilitated formation of discrete compounds [D. C. Aluthge, et al., *Inorg. Chem.*, 2014, 53, 6828-6836; K. M. Osten, et al., *Dalton Trans.*, 2012, 41, 8123-8134; K. M. Osten, et al., *Inorg. Chem.*, 2014, 53, 9897-9906; K. M. Osten, et al., *Dalton Trans.*, 2015, 44, 6126-6139].

It was considered that replacement of an ethoxide group with a coordinating alkoxide (e.g., pyridin-2-ylmethoxide), may solve this problem. This approach afforded an indium-alkoxide bond where, for example, a pyridine moiety occupied a In coordination site to form a stable six-coordinate metal center. Complexes (R,R)-11 and (R,R)-12 were prepared using the salt metathesis route, by treating (R,R)-1 and (R,R)-5, respectively, with potassium pyridin-2-ylmethoxide, KOCH$_2$Pyr (FIG. 10). The ortho-bromo complex was accessed in a one-pot synthesis by treating H$_2$(ONNO$_{Br}$) with InCl$_3$ and excess KOCH$_2$Pyr (FIG. 10). In contrast to (R,R)-11 and (R,R)-13, bulkier complex (R,R)-12 was more challenging to obtain in pure form, with minor impurities (~5-10%) observed by $^1$H NMR spectroscopy after repeated purification attempts.

Single crystals of (R,R)-11 and (R,R)-12 were obtained by slow evaporation from hexanes. Solid state structures of these mononuclear complexes showed distorted octahedral indium centers supported by a chelating pyridyl moiety (FIG. 11). Comparison of the In—N bond distances of (R,R)-11 showed that the In-NPyr bond distance of 2.296 (2) Å was longer than the two In-NImine bond distances (2.228 (2) and 2.258 (2) Å. In contrast, for (R,R)-12, the In—N bond distances had similar values, with In-NPyr and the two In-NImine being 2.242(7), 2.233 (7), and 2.234 (6) Å, respectively. The shorter In-NPyr bond for (R,R)-12 indicated stronger coordination of the pyridyl moiety. C—Si bond distances (1.862 (8)-1.874(8) Å) between the salicyl-aldehyde moiety and the —SiPh$_3$ groups were longer than the analogous C—C bond distances in (R,R)-11 (1.548(3)-1.539(3) Å), indicating that the steric bulk lied further away from the indium centre in (R,R)-12 compared to (R,R)-11.

Solution structures of these compounds corresponded to those in the solid state. $^1$H NMR spectra of (R,R)-11 and (R,R)-13 showed singlets corresponding to methylene resonances of pyridin-2-ylmethoxide at 5.03 and 4.77 ppm, respectively. However in (R,R)-12, with the bulkier —SiPh$_3$ groups, the methylene protons appeared as two diastereotopic resonances at 4.59-4.54 and 4.05-4.01 ppm. This suggested fluxional behaviour of the pyridine moiety in (R,R)-11 and (R,R)-13, which was hindered in 12. Variable temperature $^1$H NMR spectra (CDCl$_3$) of (R,R)-11 showed the room temperature singlet at 5.03 ppm resolving into two diastereotopic resonances at −20° C.

Synthesis of potassium pyridin-2-ylmethoxide (KOCH$_2$Pyr): A 20 mL scintillation vial was charged with 2-pyridine methanol (0.629 g, 5.76 mmol), 7 mL of THF and a Teflon stir bar. In a separate 20 mL vial KOtBu (0.647 g, 5.76 mmol) was dissolved in 7 mL of THF. The KOtBu solution was added slowly to the stirring 2-pyridine methanol solution. After ~10 min of stirring, a light grey precipitate can be observed. The reaction was allowed to stir for 16 h. The reaction was allowed to settle, and the dark green solution was decanted to isolate a grey colored solid. This solid was repeatedly washed with hexanes, until the washings were colorless. Then the solid was dried in vacuo to give KOCH$_2$Pyr a white powder (yield: 0.780 g, 92%). $^1$H NMR (600 MHz, THF-d$_8$, 25° C.): δ 8.35 (1H, br s, ArH (Pyr)), 7.52 (1H, t (J$^3$=5.6 Hz), ArH (Pyr)), 7.38-7.35 (1H, m, ArH (Pyr)), 6.99-6.97 (1H, m, ArH (Pyr)), 6.98 (1H, br s, —CH$_2$—). While the compound was sufficiently soluble to obtain a $^1$H NMR spectrum, we were unable to get $^{13}$C{H} data for the compound due to poor solubility in common solvents. Anal. calcd (found) for C$_6$H$_6$NOK: C, 48.95 (48.61); H, 4.11 (4.86); N, 9.51 (8.78).

Synthesis of (R,R)—[(ONNO$_{tBu}$)InOCH$_2$Pyr (R,R)-11

Complex (R,R)-1 (0.124 g, 0.178 mmol) was dissolved in toluene (2 mL) and added to a slurry of potassium pyridin-2-ylmethoxide (0.027 g, 0.183 mmol) in toluene (2 mL). The mixture was stirred at room temperature for 16 h. The resulting mixture was filtered and the solution evaporated under vacuum to afford a yellow solid (yield: 0.105 g, 77%). Yellow coloured X-ray quality crystals were obtained by crystallizing from hexanes at ambient temperature. $^1$H NMR (400 MHz, CDCl$_3$, 25° C.): δ 8.66-8.65 (1H, d, ArH (pyr)), 8.31 (1H, s, N═CH), 8.14 (1H, s, N═CH), 7.70-7.67 (1H, m, ArH (pyr)), 7.46 (1H, s, ArH), 7.30 (1H, s, ArH), 7.21-7.18 (1H, m, ArH (pyr)), 7.15-7.11 (1H, m, ArH (pyr)), 5.02 (2H, s, —CH$_2$— of —OCH$_2$Pyr), 4.29-4.24 (1H, m, —CH—), 3.03-2.98 (1H, m, —CH—), 2.54-2.49 (1H, m, —CH$_2$— of DACH), 2.24-2.21 (1H, m, —CH$_2$— of DACH), 2.05-1.98 (2H, m, —CH$_2$— of DACH), 1.74-1.69 (1H, m, —CH$_2$— of DACH), 1.60-1.56 (2H, m, —CH$_2$— of DACH), 1.49 (9H, s, Ar—C(CH$_3$)$_3$), 1.42-1.35 (1H, m, —CH$_2$— of DACH), 1.30 (9H, s, Ar—C(CH$_3$)$_3$), 1.27 (9H, s, Ar—C(CH$_3$)$_3$), 1.19 (9H, s, Ar—C(CH$_3$)$_3$). $^{13}$C{$^1$H} NMR (151 MHz, CDCl$_3$): δ 169.1, 168.7, 168.1, 165.5, 164.6, 147.6, 141.2, 141.1, 138.1, 135.4, 135.0, 129.9, 129.3, 128.8, 128.5, 121.8, 121.4, 118.2, 117.8, 67.4, 64.9, 63.9, 35.8, 35.2, 33.0, 31.4, 30.0, 29.6, 29.3, 27.2, 24.8, 23.8. Anal. calcd (found) for C$_{42}$H$_{58}$N$_3$O$_3$In: C, 65.71 (66.02), H, 7.61 (7.78), N, 5.47 (5.83).

Synthesis of (R,R)—[(ONNO$_{SiPh3}$)InOCH$_2$Pyr (R,R)-12

Complex (R,R)-12 was synthesized via the salt metathesis of (R,R)-5 (0.126 g, 0.124 mmol) (yield: 0.069 g, 51%, 25° C.). A red solid obtained was further purified by washing with acetonitrile and dried under vacuum. However, minor impurities were still observed in the $^1$H NMR spectrum. $^1$H NMR (600 MHz, CDCl$_3$): δ 8.26 (1H, s, N═CH), 7.94 (1H, s, N═CH), 7.80-6.74 (37H, overlapping peaks, ArH (pyr) and ArH (—SiPh$_3$)), 6.22-6.19 (1H, m, ArH (pyr)), 4.56 (1H, d (J$^2$=20 Hz), —CH$_2$— of —OCH$_2$Pyr), 4.38-4.34 (1H, m, —CH—), 4.03 (1H, d (J$^2$=20 Hz), —CH$_2$— of —OCH$_2$Pyr), 2.92-2.85 (1H, m, —CH—), 2.30-1.28.49 (8H, overlapping multiplets, —CH$_2$— of DACH), 2.17 (3H, s, ArCH$_3$), 2.05 (3H, s, ArCH$_3$), $^{13}$C NMR (151 MHz, CDCl$_3$, 25° C.): 165.2, 164.0, 159.0, 148.1, 145.8, 141.1, 139.3, 138.0, 137.4, 135.1, 135.9, 135.7, 134.6, 134.4, 128.6, 127.8, 127.2, 126.7, 124.8, 122.0, 121.6, 120.8, 120.4, 120.0, 65.4, 63.6, 32.6, 30.8, 24.4, 23.4, 21.0, 20.1, 20.0, 19.7, 13.7. $^{13}$C{$^1$H} resonances could not be identified with confidence due to presence of impurities and overlapping signals. X-ray quality crystal were not obtained in sufficient yield for further reactivity.

Synthesis of (R,R)—[(ONNO$_{Br}$)InOCH$_2$Pyr (R,R)-13

A 20 mL scintillation vial was charged with proligand H$_2$(ONNO$_{Br}$) (0.037 g, 0.063 mmol), anhydrous InCl$_3$ (0.019 g, 0.094 mmol), 2 mL toluene and a magnetic stir bar. This was allowed to stir for 30 min and a suspension of 5 equiv of potassium pyridin-2-ylmethoxide (0.047 g, 0.31 mmol) in 2 mL toluene was added to the reaction. The mixture was stirred at room temperature for 16 h, and remaining salt was filtered off using a glass filter paper. The solution was then evaporated under vacuum to afford a yellow solid. This was further purified with successive washings with hexanes to remove any residual 2-pyridinemethanol and dried in vacuo. (yield: 0.026 g, 51%). $^1$H NMR (400 MHz, CDCl$_3$, 25° C.) δ 9.50-9.48 (1H, d, ArH (pyr)), 8.58-8.57 (1H, d, ArH (pyr)) 8.33 (1H, s, N=CH), 8.13 (1H, s, N=CH), 7.75-7.68 (2H, m, ArH (pyr)), 7.65 (1H, s, ArH), 7.57 (1H, s, ArH), 7.04 (1H, s, ArH), 6.99 (1H, s, ArH), 4.77 (2H, s, —CH$_2$— of —OCH$_2$Pyr), 4.41-4.35 (1H, m, —CH— of DACH), 3.12-3.08 (1H, m, —CH— of DACH), 2.37-2.30 (1H, m, —CH$_2$— of DACH), 2.09-2.02 (1H, m, —CH$_2$— of DACH), 1.84-1.77 (2H, m, —CH$_2$— of DACH), 1.71-1.44 (4H, m (overlapping), —CH$_2$— of DACH), 1.25 (9H, s, ArC(CH$_3$)$_3$), 1.23 (9H, s, ArC(CH$_3$)$_3$). $^{13}$C {$^1$H}NMR (151 MHz, CDCl$_3$, 25° C.): δ 169.1, 164.1, 163.7, 163.2, 148.6, 138.2, 137.9, 137.6, 134.7, 134.5, 130.7, 130.2, 122.3, 120.7, 118.8, 118.2, 117.8, 67.4, 64.5, 63.7, 33.7, 31.3, 29.9, 27.4, 24.7, 23.7. Anal. calcd (found) for C$_{34}$H$_{40}$Br$_2$InN$_3$O$_3$: C, 50.21 (50.38); H, 4.96 (5.00); N, 5.17 (5.51).

Solution Structures of Salen Indium Alkoxide Complexes:

Procedure for reaction of pyridine with (R,R)-6:

In a 20 mL scintillation vial, (R,R)-6 (10 mg, 7 10$^{-3}$ mmol) was dissolved in neat pyridine (5 mL) and the solution was transferred to Teflon capped flask with a stir bar. The Teflon sealed flask was taken out of a glove box, stirred under reflux for 16 h. Thereafter the reaction was dried under vacuum and a NMR sample was prepared of the contents in CDCl$_3$ and a $^1$H NMR spectrum was acquired.

Procedure for reaction of ethyl acetate with (R,R)-6:

A 20 mL scintillation vial was charged with (R,R)-6 (10 mg, 7×10$^3$ mmol), ethyl acetate (5 mL) and a Teflon stir bar. The reaction was allowed to stir at room temperature for 16 h. Thereafter the reaction was dried under vacuum and a NMR sample was prepared of the contents in CDCl$_3$ and a $^1$H NMR spectrum was acquired.

Representative procedure for sample preparation for PGSE NMR spectroscopy (±)-6:

In a 1.00 mL volumetric flask, 6.2 mg of (±)-6 (0.0044 mmol, 0.0044 M) was dissolved and made up to the line with a standard solution of tetrakis(trimethylsilyl)silane (TMSS) (0.94 mM in CD$_2$Cl$_2$) which was previously prepared. TMSS was used as an internal standard. A 0.5 mL volume of this solution of (±)-6 in TMSS was transferred into a NMR tube, which was sealed with a Teflon cap for spectroscopy.

Procedure for calculating the diffusion coefficient and radii of a compound from PGSE NMR and X-ray data:

Translational diffusion coefficients (D$_t$) were calculated from plots of ln(I/I$_0$) vs. $\gamma^2\delta^2 G^2[\Delta-(\delta/3)]\times 10^{-10}$ (m$^2$ s) (FIG. 12). A modified Stokes-Einstein equation (1) was used to calculate the $c^{sa}r_H^{sa}$ value [Macchioni, A. et al., Chem. Soc. Rev. 2008, 37, 479]. Equation 2 was used to determine f$_s$. A plot of $c^{sa} r_H^{sa}$ vs. $r_H^{sa}$ based on equation 3 reported by Chen et al. was used to $r_H^{sa}$ [Chen, H. C.; Chen, S. H., J. Phys. Chem. 1984, 88, 5118].

$$c^{sa} r_H^{sa} = \frac{D_t^{st} c^{st} f_s^{st} r_H^{st}}{D_t^{sa} f_s^{sa}} \quad (1)$$

D$_t^{st}$=translational diffusion coefficient of internal standard (TMSS, D$_t^{st}$≈14.2×10$^{-10}$ m$^2$ s$^{-1}$, CD$_2$Cl$_2$, 25° C.); c$^{st}$=internal standard size correction factor (TMSS, c$^{st}$=5.1); f$_s^{st}$=internal standard size and shape correction factor (TMSS, f$_s^{st}$=1); r$_H^{st}$=internal standard hydrodynamic radius (TMSS, 4.51 Å); D$_t^{sa}$=translational diffusion coefficient of sample (CD$_2$Cl$_2$, 25° C.); c$^{sa}$=sample size correction factor; f$_s^{sa}$=sample size and shape correction factor calculated from eq (2); r$_H^{sa}$=sample hydrodynamic radius $$f_s = \frac{\sqrt{1-\left(\frac{b}{a}\right)^2}}{\left(\frac{b}{a}\right)^{\frac{2}{3}} \ln\frac{1+\sqrt{1-\left(\frac{b}{a}\right)^2}}{\left(\frac{b}{a}\right)}} \quad (2)$$

a=major semiaxes of a prolate ellipsoid estimated from X-ray crystal structure; b=minor semiaxes of a prolate ellipsoid estimated from X-ray crystal structure $$cr_H = \frac{6 r_H}{1 + 0.695\left(\frac{r_{solv}}{r_H}\right)^{2.234}} \quad (3)$$

r$_{solv}$=hydrodynamic radius of the solvent (CH$_2$Cl$_2$=2.49 Å); r$_H$=hydrodynamic radius of sample It was shown that the nuclearity of indium complexes can have an impact on their reactivity and selectivity in lactide polymerization [A. F. Douglas, et al., Angew. Chem. Int. Ed., 2008, 47, 2290-2293; I. Yu, et al., J Am. Chem. Soc, 2012, 134, 12758-12773; K. M. Osten, et al., Dalton Trans., 2012, 41, 8123-8134; K. M. Osten, et al., Inorg. Chem., 2014, 53, 9897-9906; K. M. Osten, et al., Dalton Trans., 2015, 44, 6126-6139]. Previously, it was determined that complex 6 was dinuclear in solution by using diffusion coefficient determined using Pulsed Gradient Spin Echo (PGSE) NMR spectroscopy [D. C. Aluthge, et al.i, Inorg. Chem., 2014, 53, 6828-6836]. Using the same methodology (FIG. 12), diffusion coefficients (D$_t$) for complexes 7-11 and 13 were obtained and compared to D$_t$ values of species with known solution structures (Table 3). D$_t$ values of ethoxide-bridged complexes 6-10 were similar, with values 20-30% smaller than those for the proligands, confirming the dinuclear nature of these complexes (Table 3, entries 5-9). In contrast, complexes 11 and 13 had D$_t$ values similar to those of the proligand and of complex (±)-1, which indicated that these complexes remained mononuclear in solution (Table 3, entries 3-4).

It was found that alkoxide-bridged dimers had different stabilities in solution, which could affect their reactivity with lactide. $^1$H NMR spectrum of (R,R)-6 in THF-d$_8$ showed no indication of dissociation. When (R,R)-6 was stirred in refluxing pyridine for 16 h no changes in the complex were observed in the $^1$H NMR spectrum. However, a similar reaction in neat ethyl acetate showed that ~20% of the compound was converted to other products. This suggested that, while the dinuclear ethoxide complex was stable in solution, it could dissociate in the presence of esters, such as, for example, ethyl acetate and lactide.

Crossover Experiment Between Complex R,R-6 and Complexes (R,R)-8 and (R,R)-10, Respectively Representative procedure for crossover experiment:

In two 20 mL scintillation vials, (R,R)-6 (5.2 mg, 3.7×10$^{-3}$ mmol) and (R,R)-8 (6.3 mg, 3.7×10$^{-3}$ mmol) were weighed separately. A volume of 0.3 mL of $CD_2Cl_2$ was added to each vial and the contents were mixed inside Teflon sealed J-young tube and taken to the NMR spectrometer immediately to acquire spectra.

Relative stability of these complexes were investigated further by using crossover experiments between the t-butyl substituted complex, (R,R)-6, and the adamantyl, and brom-substituted analogues (R,R)-8 and (R,R)-10, respectively (FIG. 13). The (R,R)-6/(R,R)-8 pair with bulkier ortho substituents showed almost complete crossover in 10 min. The (R,R)-6/(R,R)-10 pair showed no evidence of a crossover product in this period, and only minor crossover after 16 h. This suggested that $[(ONNO_{Br})In(OEt)]_2$ was less prone to dissociation than the bulkier analogues.

Lactide Polymerization Studies

Representative procedure for ROP of lactide—Large scale samples for GPC and $^1H\{^1H\}$ NMR studies:

In a 20 mL scintillation vial charged with a stir bar, rac-6 (5.0 mg, 0.035 mmol) was dissolved in 2 mL of $CH_2Cl_2$. rac-lactide (0.205 g, 1.42 mmol) in 2 mL of $CH_2Cl_2$ was added to the stirring solution. The reaction was allowed to proceed for 4 h, after which time the reaction was quenched with a few drops of HCl (1.5 M) in diethyl ether. A 0.5 mL sample of the reaction mixture was evaporated under vacuum for 3 hours and was dissolved in $CDCl_3$. $^1H\{^1H\}$ NMR spectrum of the methine region was obtained on a Bruker 600 MHz spectrometer. An analogous procedure was followed for the polymerization of rac-LA (lactic acid) with other catalysts. Thereafter, the mixture was evaporated under vacuum and polymer was isolated by washing three times with cold methanol. The isolated polymer was subsequently dried under vacuum for 4 h prior to GPC analysis.

Depolymerization Experiments:

In the glovebox, a 200 mg sample of isolated, dry poly (lactic acid) (synthesized using (R,R)-6, Table 5, entry1) was dissolved in 3 mL of $CH_2Cl_2$. To this stirring solution, (R,R)-6 (5 mg, 0.004 mmol) dissolved in 1 mL $CH_2Cl_2$ was added. ([(R,R)-6]~1 mM to replicate polymerization conditions.) A control reaction was setup simultaneously, without addition of (R,R)-6. Total volume was kept the same in both reactions. After 16 h, reactions were quenched with a drop of HCl (1.5 M in $Et_2O$), and polymer samples were isolated through the addition of cold methanol. Polymers were dried under vacuum for 8 h prior to GPC analysis (Table 5).

Representative procedure for determination of glass transition temperature ($T_g$) of polymers:

Approximately 2-3 mg of each sample was weighed and sealed in an aluminum pan. Experiments were carried out under a nitrogen atmosphere. Samples were heated at a rate of 10° C./min from 40 to 200° C. and then held isothermally for 5 min to destroy any residual crystal nuclei before cooling at 5° C./min. Transition and melting temperatures were obtained from a second heating sequence, performed at 10° C./min.

Determination of Polymer Tacticity:

Representative analysis of homonuclear decoupled $^1H\{^1H\}$ NMR spectra to determine tacticity (FIG. 14), wherein: for Method A, only equations [rmm]* and [rmr]* were used; for Method B, a deconvolution program was used incorporating all equations (described below):

Method of Analysis #1 [F. A. Bovey, P. A. Mirau, NMR of Polymers; Academic Press, San Diego, 1996]:

Equations used:

$$[mmm]=(P_m)^2+P_rP_m/2$$

$$[mmr]=P_rP_m/2$$

$$[rmm]^*=P_rP_m/2$$

$$[rmr]^*=(P_r)^2/2$$

$$[mrm]=((P_r)^2+P_rP_m)/2$$

$$P_r=\sqrt{(2/1.00+3.99+50.9)}=0.189$$

$$P_m=2(3.99/55.89)/0.189=0.76$$

*Effectively only these two equations were used in the calculations as other peaks cannot be accurately integrated (Method A; see below).

Method of Analysis #2 [Coudane, J. et al., Polym. Sci., Part A: Polym. Chem. 1997, 35, 1651]:

Equations used:

$$[mmm]=P_m(P_m+1)/2$$

$$[mmr]=P_m(1-P_m)/2$$

$$[rmm]=P_m(1-P_m)/2$$

$$[rmr]=(1-P_m)^2/2$$

$$[mrm]=(1-P_m)/2$$

| Peak | Integration | $P_m$ |
| --- | --- | --- |
| rmr | 0.02 | 0.80 |
| rmm | 0.07 | 0.83 |
| mmr | 0.03 | 0.93 |
| mmm | 0.80 | 0.86 |
| mrm | 0.08 | 0.84 |

All five peaks above were used in the calculations. Spectral deconvolution was used in integration of all 5 peaks. All deconvolutions were computed using NMR processing software MesRenoVa 10.0.1 with generalized Lorentzian line fitting. Efforts were made to minimize the residual error ~1% (Method B; see below).

Impact of Ligand Substituents on Selectivity:

With a range of steric bulks substituting the above described Salen-In complexes, impact of steric bulk of ligand substituents on isoselective polymerizations of racemic lactide (rac-LA) was investigated (Table 4). Gel permeation chromatographic (GPC) analysis of the polymers generated with catalysts (R,R)-7-12 showed good molecular weight control. Polymer dispersities were similar to those obtained for (R,R)-6, and indicated transesterification [D. C. Aluthge, et al., Chem. Commun., 2013, 49, 4295-4297]. It was found that, polymerization reactions that were not quenched after full conversion could undergo depolymerization, which affected molecular weights and poly dispersity indexes (PDIs). If an isolated polymer was redissolved and stirred for 16 h at room temperature along with (R,R)-6, a 30% decrease in the molecular weight is observed (Table 5).

It was found that the above described catalysts were isoselective. $P_m$ values were calculated by substituting integrations of tetrad sequences, determined using $^1H\{^1H\}$NMR spectroscopy. Tacticity of PLA was calculated using a set of equations derived using a Bernoullian statistical model [B. M. Chamberlain, et al., *J. Am. Chem. Soc.*, 2001, 123, 3229-3238; F. A. Bovey and P. A. Mirau, *NMR of Polymers*, Academic Press, San Diego, 1996]. While use of these equations in direct interpretation of integrations of $^1H\{^1H\}$ NMR spectra of PLA was well established [J. Coudane, et al., *J. Polym. Sci., Part A: Polym. Chem.*, 1997, 35, 1651-1658; M. T. Zell, et al., *Macromolecules*, 2002, 35, 7700-7707 E], other reports used a different methodology of peak deconvolution for calculating tacticity [H. B. Wang, et al., *Macromolecules*, 2014, 47, 7750-7764; N. Maudoux, et al., *Chem. Eur. J.*, 2014, 20, 6131-6147; C. Bakewell, et al., *J. Am. Chem. Soc.*, 2012, 134, 20577-20580; C. Bakewell, et al., *Angew. Chem. Int. Ed.*, 2014, 53, 9226-9230; J. Coudane, et al., *J. Polym. Sci., Part A: Polym. Chem.*, 1997, 35, 1651-1658; H. R. Kricheldorf, et al., *Polymer*, 1992, 33, 2817-2824; A. M. Goldys and D. J. Dixon, *Macromolecules*, 2014, 47, 1277-1284; T. R. Jensen, et al., *Chem. Commun.*, 2004, 2504-2505].

This issue had arisen partly due to the fact that, with most commonly available NMR instruments, mmr, mmm, mrm resonances overlap and cannot be integrated separately. Therefore, calculation of $P_m$ values can be based on integration of rmr and rmm resonances in a majority of systems where perfectly isotactic PLA is not formed and stereoerrors are present (Method A).

Accuracy of $P_m$ values calculated using deconvoluted spectra (Method B) depends on the accuracy and the applicability of the deconvolution algorithm and spectral resolution; this limitation was encountered for the systems herein described. Inspection of results in Table 4 showed that the deconvolution methodology had inflated the $P_m$ values. For example, inspection of entries 1 and 3 shows that catalysts 6 and 8 had nearly identical $P_m$ values generated from Method A, with different values from Method B. This discrepancy widens when comparing entries 3 and 5, with identical values for Method B and different values for Method A.

Another inconsistency of Method B arose from the relationship between $P_m$ and $P_r$ values: a general form of the equations delineated above used $P_m$ and $P_r$ as two independent variables, requiring use of at least two different equations to calculate tacticity [B. M. Chamberlain, et al., *J Am. Chem. Soc.*, 2001, 123, 3229-3238; F. A. Bovey and P. A. Mirau, *NMR of Polymers*, Academic Press, San Diego, 1996]. However, in order to apply Method B, the relationship $P_m=1-P_r$ must be true. These equations were reduced to expressions containing a single variable $P_m$; values for each of the five resonances delineated above were calculated and averaged to give a final $P_m$ value for the polymer [J. Coudane, et al., *J Polym. Sci., Part A: Polym. Chem.*, 1997, 35, 1651-1658]. This derivation, however, was only valid for a system with exclusive site control where a single statistical event does not impact the other; it was not for those where both site and chain-end control may be operative, such as the systems described herein [F. A. Bovey and P. A. Mirau, *NMR of Polymers*, Academic Press, San Diego, 1996].

It was acknowledged that there was no ideal way to calculate tacticities based on the above equations due to non-ideal behaviours of natural systems, and thus concluded that any comparison of literature $P_m$ values must be carried out with consistency and transparency.

It was considered that polymer melting point may be a stronger arbiter of isotacticity in PLA. For the herein described systems, polymers generated from rac-LA with most stereoselective catalysts, (R,R)-6 and (R,R)-8, were amorphous ($T_g$~55° C.) (for example, see FIG. 15). In comparison, Williams et al. have reported systems with similar $P_m$ values obtained using peak deconvolution methodology which were crystalline having $T_m$ values>170° C. As such, a comparison of the two systems using only $P_m$ values obtained using peak deconvolution may be insufficient [C. Bakewell, et al., *J. Am. Chem. Soc.*, 2012, 134, 20577-20580; C. Bakewell, et al., *Angew. Chem. Int. Ed.*, 2014, 53, 9226-9230].

A comparison of selectivities listed in Table 4 using Method A showed that a decrease in ligand steric hinderance correlated to decreased $P_m$ values, while increasing steric bulk of the ligands did not result in an appreciable increase in $P_m$ values above ~0.75. A similar observation was made by Chen-Xin Cai et at., *Chem. Commun.*, 2004, pp. 330-331, in a series of aluminum salen catalysts with a chiral diphenyl ethylene backbone for lactide polymerization, where changing the ortho substituent from t-butyl group to a methyl functionality decreased isoselectivity from $P_m$~0.9 to ~0.8 [Maudoux, et al., *Chem. Eur. J.*, 2014, 20, 6131-6147]. This suggested that, although the ortho substituents of the salicylaldehyde moieties played a role in imparting stereoselectivity, a mechanism for control of selectivity may he more nuanced.

Differences in ligand steric bulk had an impact on rates of propagation (Table 6). Cumyl-substituted complex (R,R)-9 required longer reaction times for reaching full conversion than adamantyl substituted complex (R,R)-8 under the same reaction conditions. It was considered that this may be due to a more sterically congested ligand environment, which hindered approach of lactide to the metal centre. In situ monitoring of catalysts (R,R)-8 and (R,R)-9 showed first order rates for ring opening polymerization of L-, D-, and rac-LA similar to those observed for (R,R)-6 (FIG. 16). Plot for (R,R)-8 showed a brief initiation period followed by linear propagation, while for (R,R)-9, the initiation period was not observable. Both catalysts polymerized L-LA more rapidly than D-LA, with $k_{L-LA}/k_{D-LA}$ values of 4 and 6, respectively, for (R,R)-8 and (R,R)-9 (Table 6, entries 1, 2 and 4, 5).

It was considered that a closer examination of polymerization behaviours of [(ONNO$_{Br}$)InOEt]$_2$ (R,R)-10 and [(ONNO$_{Me}$)InOEt]2 (R,R)-7 could elucidate the impact of decreased steric bulk on reaction rates (Table 4, entries 7-10). Both (R,R)-10 and (R,R)-7 polymerized 200 equiv of rac-LA in double the time required for bulkier (R,R)-6 under identical conditions. Furthermore, catalysts 7 and 10 generated polymers with higher than expected molecular weights at low monomer loading (Table 4, entries 7 and 9).

In situ monitoring of catalysts (R,R)-7 and (R,R)-10 showed that rates of polymerization of rac-LA for said catalysts did not have a first order dependence on lactide concentration (FIG. 20). First order plots for polymerization of L-, D- and rac-LA with both catalysts showed relatively longer initiation periods (>1 h) compared to (R,R)-6, with (R,R)-10; this was consistent with the higher than expected molecular weights of the polymers. While first order rate constants cannot be calculated due to the curved nature of the plots, a qualitative assessment of the plots suggested that (R,R)-10 did not show a marked preference for one enantiomer of lactide over the other. This was consistent with the essentially atactic nature of the polymers generated ($P_m$~0.55). Complex (R,R)-7, which generated PLA with a isotacticity of $P_m$~0.60, showed a higher rate for polymerization of L-LA. These observations, in conjunction with the shorter initiation periods observed for bulkier complexes (R,R)-6, (R,R)-8, and (R,R)-9, suggested that bulkier complexes may undergo more facile initiation.

Nature of the Propagating Species:

Although complexes 6-10 were dinuclear in solution, as described above, it was found that there was an equilibrium between said complexes' dimeric and monomeric forms, which could be perturbed with addition of donors such as ethyl acetate (described above). It was found that this equilibrium could also be perturbed in the presence of lactide. In previous work with asymmetrically-bridged dinulcear indium complexes supported by tridentate ligands, it was shown that propagating species in the presence of lactide was dinuclear [I. Yu, et al., *J Am. Chem. Soc*, 2012, 134, 12758-12773], and that nuclearity of the propagating species was consequential in controlling the macro- and microstructure of PLA generated [K. M. Osten, et al., *Dalton Trans.*, 2012, 41, 8123-8134; K. M. Osten, et al., *Inorg. Chem.*, 2014, 53, 9897-9906; K. M. Osten, et al., *Dalton Trans.*, 2015, 44, 6126-6139]. Thus, it was considered that it was necessary to determine nuclearity of the propagating species to determine mechanism of polymerization and origin of initiation periods in the herein described Salen-In systems. It was considered that, if a dinuclear complex [(ONNO$_R$)In(OEt)]$_2$ and its mononuclear analogue (ONNO$_R$)InOCH$_2$Pyr showed the same reactivity and selectivity, they may share a similar or same propagating species.

Polymerization data for [(ONNO$_{tBu}$)In(OEt)]2 (R,R)-6 and (ONNO$_{tBu}$)InOCH$_2$Pyr (R,R)-11 were relatively similar (Table 4, entries 1, 2 and 11, 12). Both complexes showed living behaviour for polymerization of rac-LA (FIG. 17). Polymers generated with both catalysts were isotactically enriched, with P$_m$ values of ~0.75. MALDI-TOF spectra of PLA oligomers made with both catalysts showed peaks corresponding to [H(C$_3$H$_4$O)$_n$(OZ)H]$^+$ (Z=OEt or OCH$_2$Pyr) separated by m/z~72, which indicated extensive transesterification (for example, see FIG. 18). k$_{obs}$ values and k$_{L-LA}$/k$_{D-LA}$ ratios (both 5) were consistent with (R,R)-6 and (R,R)-11 having the same propagating species.

A difference between complexes 6 and 11 was a slight initiation period observed for 6, which was not observed for 11 (FIGS. 16 and 19). This distinction was magnified for the less bulky complexes (ONNO$_{Br}$)InOCH$_2$Pyr (R,R)-13 and [(ONNO$_{Br}$) InOEt]$_2$ (R,R)-10. Mononuclear complex (R,R)-13 lacked a prolonged initiation period of its dinuclear analogue (FIGS. 19 and 20), and was more active than other Salen-In catalysts investigated (Table 6, entries 10-12). Unlike (R,R)-10, molecular weights of polymers made with (R,R)-13 at low lactide loadings matched expected values closely (Table 4, entries 7,13), which was consistent with a lack of initiation period. Complexes (R,R)-10 and 13 showed no preference for either enantiomer of lactide; polymers generated with both catalysts were essentially atactic; this indicated that an initiation period does not affect overall selectivity (Table 4, entries 13-14).

In view of the foregoing, a mechanism was proposed where during the initiation step, dinuclear complexes dissociate in the presence of lactide to form mononuclear propagating species (FIG. 21). It was considered that equilibria between monomeric and dimeric forms of the herein described catalysts were dictated by the steric bulk of the ligand substituents, given that initiation periods were longer for less bulky dinuclear complexes 7 and 10, as compared to complexes 6 and 8. The bulkier cumyl-substituted dimer 9 did not exhibit an observable initiation period. When mononuclear catalysts 11 and 13 were used, the initiation periods were also not observable, strongly suggesting that the initiation period was caused by a monomer-dimer equilibrium, and that the active species were mononuclear.

As such, it was observed that, with possibility of aggregation eliminated, propagation rates for mononuclear catalysts were dependent on ligand steric environments. The sterically bulky complex (ONNO$_{SiPh3}$)InOCH$_2$Pyr (R,R)-12 was the least active catalyst of the herein described complexes, achieving >90% conversion in 24 hours (Table 4, entries 15-16). In contrast, (ONNO$_{Br}$)InOCH$_2$Pyr (R,R)-13, with the lowest steric bulk, had the highest reaction rate. This disparity was attributed to the bulky ortho-phenolate groups hindering reactivity of the monomer with the metal center. It was found that a decrease in rate did not affect selectivity: catalyst (R,R)-12 generated isotactic PLA with P$_m$~0.75.

Similarities in isoselectivity of complexes 11 and 12 was investigated by examining the mononuclear complexes' structures, as these were considered the propagating species (FIG. 11). It was considered that the coordination environment around the indium centres was flexible, and instead of generating a C$_2$ symmetric axis, the ligand created a C$_1$ symmetric steric environment that prevented steric control of lactide coordination to the indium centres.

CONCLUSIONS

Structure/activity relationship were investigated for the herein described systems of dinuclear and mononuclear Salen-In complexes. It was demonstrated that said complexes were effective catalysts for the isoselective polymerization of racemic lactide [P. Mehrkhodavandi, et al., Pat., PCT/CA2013/050191, 2013].

In particular, a generally applicable methodology was developed for preventing aggregation by using a coordinating alkoxide, pyridin-2-ylmethoxide. These mononuclear catalysts showed no initiation period and facilitated the determination, unlike their tridentate counterparts, the propagating species for tetradentate indium salen complexes is mononuclear.

The results above elude to the mononuclear salen complexes described herein performing as polymerization catalysts at least as well as the dimer salen complexes disclosed in PCT application PCT/CA2013/050191. Consequently, without being bound by theory, it has been postulated that the mononuclear salen complexes described herein would perform well in reactions the dimer complexes have demonstrated success as a catalyst, as disclosed in PCT application PCT/CA2013/050191, even if said reactions have not been expressly described here.

TABLE 1

Polymerization data from Initial Studies of Homonuclear Salen-In Catalysts

|   | Catalyst | Time (h) | Conv (%) | M$_{ntheo}$ (kDa) | M$_{nGPC}$ (kDa) | PDI | P$_m$ |
|---|---|---|---|---|---|---|---|
| 1 | (R,R)-2 | 1.0 | 98 | 28.2 | 36.9 | 1.23 | 0.76 |
| 2 | (R,R)-2 | 2.0 | 95 | 54.7 | 48.6 | 1.26 | 0.74 |
| 3 | (R,R)-4 | 24 | 76 | — | — | — | 0.75 |

TABLE 2

Selected crystallographic parameters of X-ray structures for Complexes (R,R)-2, -3, -7, -11, and -13

| | (R,R)-2·CH₃CN | (±)-3 | (R,R)-7 | (R,R)-11 | (R,R)-12 |
|---|---|---|---|---|---|
| empirical formula | $C_{34}H_{46}N_4O_2InCl$ | $C_{48}H_{64}N_2O_2InCl$ | $C_{73}H_{103.50}N_{8.5}O_6In_2$ | $C_{42}H_{58}N_3O_3In$ | $C_{64}H_{58}N_3O_3Si_2In$ |
| Fw | 693.02 | 851.28 | 1425.78 | 767.73 | 1088.13 |
| T (K) | 90 | 90 | 90 | 90 | 90 |
| a (Å) | 36.780(4) | 11.7715(13) | 15.0752(9) | 9.192(2) | 12.019(5) |
| b (Å) | 8.3688(8) | 12.7462(15) | 22.4148(14) | 16.465(4) | 20.066(9) |
| c (Å) | 24.188(2) | 15.4167(17) | 23.2893(13) | 25.858(6) | 23.278(11) |
| □ (deg) | 90 | 105.421(2) | 90 | 90 | 90 |
| □ (deg) | 115.260(2) | 96.436(2) | 90 | 90 | 90 |
| □ (deg) | 90 | 103.430(2) | 90 | 90 | 90 |
| volume (Å³) | 6733.3(11) | 2131.3(4) | 7869.6(8) | 3913.6(15) | 5614(4) |
| Z | 8 | 2 | 4 | 4 | 4 |
| crystal system | monoclinic | triclinic | orthorhombic | orthorhombic | orthorhombic |
| space group | C 2 (#5) | P-1(#2) | P 21 21 21 | P 21 21 21 | P 21 21 21 |
| $d_{calc}$ (g/cm³) | 1.367 | 1.327 | 1.203 | 1.303 | 1.287 |
| μ (MoKα) (cm⁻¹) | 8.16 | 6.57 | 6.37 | 6.44 | 5.11 |
| 2□max (deg) | 60.2 | 60.3 | 60 | 58.6 | 51 |
| absorption correction ($T_{min}$, $T_{max}$) | 0.8152, 0.8705 | 0.857, 0.900 | 0.518, 0.846 | 0.8356, 0.9256 | 0.7981, 0.8231 |
| total no. of reflections | 133172 | 141946 | 42732 | 48390 | 46482 |
| no. of indep reflections ($R_{int}$) | 9766 (0.0322) | 12569 (0.0310) | 21833 (0.0437) | 10690 (0.0511) | 10262 (0.067) |
| residuals (refined on F², all data): $R_1$; $wR_2$ | 0.0228; 0.0487 | 0.0357; 0.0913 | 0.1120; 0.0670 | 0.0572:0.0388 | 0.1458:0.0647 |
| GOF | 1.026 | 1.392 | 1.02 | 1.023 | 0.722 |
| no. observations [I > 2s(I)] | 18669 | 12105 | 8453 | 9566 | 8759 |
| residuals (refined on F²): $R_1^a$; $wR_2^b$ | 0.0202; 0.0473 | 0.0343; 0.0908 | 0.1033; 0.0469 | 0.0550; 0.0307 | 0.1324; 0.0497 |

[a] $R_1 = \Sigma ||F_o| - |F_c||/\Sigma |F_o|$;
[b] $wR_2 = [\Sigma(w(F_o^2 - F_c^2)^2)/\Sigma w(F_o^2)^2]^{1/2}$.

TABLE 3

Diffusion constants and hydrodynamic radii of compounds calculated using PGSE NMR spectroscopy.

| | Compound | $D_t^a$ (×10⁻¹⁰ m²s⁻¹) | $r_H^b$ | $r_{X-ray}^c$ |
|---|---|---|---|---|
| 1 | $H_2(ONNO_{tBu})^d$ | 9.5(3) | 6.1 | 5.9 |
| 2 | $(ONNO_{tBu})InCl$ (±)-1[e] | 9.1(2) | 6.4 | 5.9 |
| 3 | $(ONNO_{Br})InOCH_2Pyr$ (R,R)-13 | 8.6(5) | 6.6 | — |
| 4 | $(ONNO_{tBu})InOCH_2Pyr$ (R,R)-11 | 8.5(2) | 6.7 | 6.2 |
| 5 | $[(ONNO_{Br})InOEt]_2$ (R,R)-10 | 6.9(4) | 8.1 | — |
| 6 | $[(ONNO_{Me})InOEt]_2$ (R,R)-7 | 7.0(4) | 8.0 | 7.8 |
| 7 | $[(ONNO_{tBu})InOEt]_2$ (±)-6[e] | 6.5(5) | 8.5 | 8.3 |
| 8 | $[(ONNO_{Ad})InOEt]_2$ (R,R)-8 | 6.3(5) | 8.8 | — |
| 9 | $[(ONNO_{Cm})InOEt]_2$ (R,R)-9 | 6.0(4) | 9.2 | — |

[a] $D_t$ was determined using PGSE NMR spectroscopy with tetrakis(trimethylsilyl)silane (TMSS) as an internal standard. [Compound] = 4.5 mM samples were prepared in 0.94 mM TMSS solution in $CD_2Cl_2$. $D_t$ is calculated from slopes of plots of $ln(I/I_0)$ vs. $\gamma^2\delta^2G^2[\Delta - (\delta/3)] \times 10^{-10}$ (m²·s).
[b] Calculated from $D_t$ values using a modified Stokes-Einstein equation (see SI).
[c] Calculated, where solid-state data is available, from the crystal structure unit cell volume (V) as well as the number of the compound of interest (n) occupying the unit cell assuming spherical shape $(3 V/4\pi n)^{1/3}$.
[d] J. W. Yoon, et al., Acta Crystallogr., Sect. C: Cryst. Struct. Commun., 1997, 53, 1685-1687.
[e] D. C. Aluthge, et al., Chem. Commun., 2013, 49, 4295-4297

TABLE 4

Polymerization of rac-lactide with Salen-In complexes.

| | Catalyst[a] | M:I | Time (h) | Conv[b] (%) | $M_{ntheo}$ (kDa) | $M_{nGPC}^c$ (kDa) | Đ | $P_m^d$ | $P_m^e$ |
|---|---|---|---|---|---|---|---|---|---|
| 1 | $[(ONNO_{tBu})InOEt]_2$ (R,R)-6 | 200 | 1 | 99 | 28.5 | 34.9 | 1.39 | 0.76 | 0.85 |
| 2 | $[(ONNO_{tBu})InOEt]_2$ (R,R)-6 | 600 | 4 | 99 | 85.5 | 89.5 | 1.52 | 0.75 | — |
| 3 | $[(ONNO_{Ad})InOEt]_2$ (R,R)-8 | 200 | 1 | 98 | 28.2 | 36.3 | 1.42 | 0.77 | 0.80 |
| 4 | $[(ONNO_{Ad})InOEt]_2$ (R,R)-8 | 500 | 2 | 99 | 71.3 | 69.4 | 1.33 | 0.74 | — |

TABLE 4-continued

Polymerization of rac-lactide with Salen-In complexes.

| Catalyst[a] | M:I | Time (h) | Conv[b] (%) | $M_{ntheo}$ (kDa) | $M_{nGPC}$[c] (kDa) | Đ | $P_m^d$ | $P_m^e$ |
|---|---|---|---|---|---|---|---|---|
| 5 [(ONNO$_{Cm}$)InOEt]$_2$ (R,R)-9 | 200 | 2 | 97 | 27.9 | 27.9 | 1.56 | 0.73 | — |
| 6 [(ONNO$_{Cm}$)InOEt]$_2$ (R,R)-9 | 500 | 5 | 98 | 70.6 | 79.0 | 1.42 | 0.72 | 0.80 |
| 7 [(ONNO$_{Br}$)InOEt]$_2$ (R,R)-10 | 200 | 2 | 97 | 27.9 | 52.9 | 1.15 | 0.55 | — |
| 8 [(ONNO$_{Br}$)InOEt]$_2$ (R,R)-10 | 500 | 5 | 99 | 71.3 | 97.0 | 1.35 | 0.57 | 0.70 |
| 9 [(ONNO$_{Me}$)InOEt]$_2$ (R,R)-7 | 200 | 2 | 98 | 28.2 | 47.5 | 1.19 | 0.60 | — |
| 10 [(ONNO$_{Me}$)InOEt]$_2$ (R,R)-7 | 500 | 5 | 99 | 71.3 | 91.7 | 1.29 | 0.62 | 0.71 |
| 11 (ONNO$_{tBu}$)InOCH$_2$Pyr (R,R)-11 | 200 | 1 | 98 | 28.5 | 36.7 | 1.27 | 0.74 | 0.78 |
| 12 (ONNO$_{tBu}$)InOCH$_2$Pyr (R,R)-11 | 600 | 4 | 97 | 83.5 | 86.1 | 1.37 | 0.75 | — |
| 13 (ONNO$_{Br}$)InOCH$_2$Pyr (R,R)-13 | 200 | 0.5 | 98 | 28.2 | 35.8 | 1.15 | 0.59 | 0.69 |
| 14 (ONNO$_{Br}$)InOCH$_2$Pyr (R,R)-13 | 500 | 0.5 | 98 | 70.6 | 70.4 | 1.25 | 0.56 | — |
| 15 (ONNO$_{SiPh3}$)InOCH$_2$Pyr (R,R)-12 | 200 | 16 | 75 | — | — | — | 0.73 | — |
| 16 (ONNO$_{SiPh3}$)InOCH$_2$Pyr (R,R)-12 | 200 | 24 | 93 | 26.8 | 36.7 | 1.30 | 0.75 | — |

[a]In CH$_2$Cl$_2$ at 25° C., [catalyst] ≈ 1 mM.
[b]Conversions were determined by $^1$H NMR spectroscopy. $M_{ntheo}$ = molecular weight of chain-end + 144 gmol$^{-1}$ × 200 × conversion.
[c]In THF (2 mg mL$^{-1}$) and molecular weights were determined by GPC-LLS (flow rate = 0.5 mL min$^{-1}$). Universal calibration was carried out with polystyrene standards, laser light scattering detector data, and concentration detector. Each experiment is duplicated to ensure precision.
[d]Calculated according to Method A, using the relative integrals of rmr and rmm resonances (See SI).
[e]Calculated using Method B after performing peak deconvolution to integrate all five peaks in the methine region of $^1$H{$^1$H}NMR spectra.

TABLE 5

GPC data for depolymerisation experiments

| Entry | Description | $M_{nGPC}$ (×10$^5$)[a] | PDI |
|---|---|---|---|
| 1 | Polymer prior to reaction | 1.70 | 1.10 |
| 2 | Polymer isolated after reaction with (R,R)-6 | 1.14 | 1.14 |
| 3 | Polymer isolated from control experiment | 1.79 | 1.09 |

[a]In THF (2 mg mL$^{-1}$) and molecular weights were determined by GPC-LLS (flow rate = 0.5 mL min$^{-1}$.) Universal calibration was carried out with polystyrene standards, laser light scattering detector data, and concentration detector. Each experiment is duplicated to ensure accuracy.

TABLE 6

Rate constants for polymerization of D-, L-, and rac-LA with (R,R)-8, (R,R)-9, (R,R)-11 and (R,R)-13

| Catalyst[a] | M[b] | $k_{obs}$ (×10$^4$ s$^{-1}$) |
|---|---|---|
| 1 [(ONNO$_{Ad}$)InOEt]$_2$(R,R)-8 | D-LA | 9.4 (2) |
| 2 [(ONNO$_{Ad}$)InOEt]$_2$(R,R)-8 | L-LA | 38 (8) |
| 3 [(ONNO$_{Ad}$)InOEt]$_2$(R,R)-8 | rac-LA | 9.4 (2) |
| 4 [(ONNO$_{Cm}$)InOEt]$_2$(R,R)-9 | D-LA | 2.4 (5) |
| 5 [(ONNO$_{Cm}$)InOEt]$_2$(R,R)-9 | L-LA | 14 (3) |
| 6 [(ONNO$_{Cm}$)InOEt]$_2$(R,R)-9 | rac-LA | 2.7 (5) |
| 7 (ONNO$_{tBu}$)InOCH$_2$Pyr (R,R)-11 | D-LA | 6.1 (12) |
| 8 (ONNO$_{tBu}$)InOCH$_2$Pyr (R,R)-11 | L-LA | 29 (6) |
| 9 (ONNO$_{tBu}$)InOCH$_2$Pyr (R,R)-11 | rac-LA | 6.9 (14) |
| 10 (ONNO$_{Br}$)InOCH$_2$Pyr (R,R)-13 | D-LA | 53 (11) |
| 11 (ONNO$_{Br}$)InOCH$_2$Pyr (R,R)-13 | L-LA | 52 (10) |
| 12 (ONNO$_{Br}$)InOCH$_2$Pyr (R,R)-13 | rac-LA | 62 (12) |

All reactions were carried out with 200 equiv of monomer (M) in CD$_2$Cl$_2$ at 25° C. and followed to 90% conversion by $^1$H NMR spectroscopy.
[a][Catalyst] = 0.0011M,
[b][M] = 0.45M.

All publications, patents and patent applications mentioned in this Specification are indicative of the level of skill of those skilled in the art to which this invention pertains and are herein incorporated by reference to the same extent as if each individual publication, patent, or patent application was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A complex having a structure of formula (Ia):

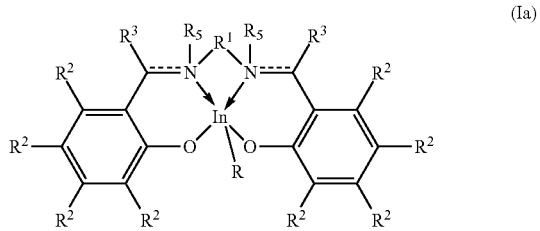

wherein the dashed line represents an optional double bond;

$R^1$ is an optionally substituted $C_{2-5}$ alkylene,

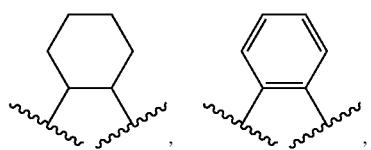

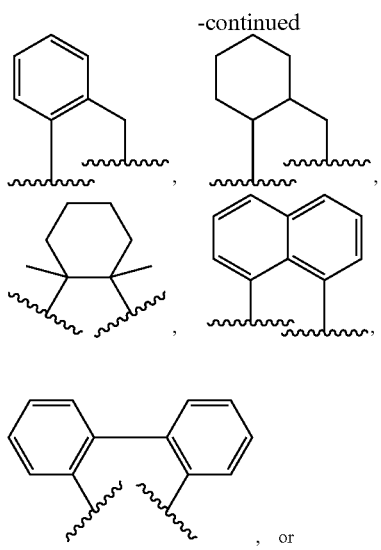

each $R^2$ is independently hydrogen, halogen, optionally substituted linear or branched $C_{1-18}$ alkyl, optionally substituted cyclic $C_{3-18}$ alkyl, or optionally substituted phenyl or $SiR'$, where $R'$ is alkyl or aryl;

each $R^3$ is hydrogen or optionally substituted linear or branched $C_{1-18}$ alkyl, or optionally substituted cyclic $C_{3-18}$ alkyl;

R is a coordinating alkoxide of formula $OR^4$, wherein $R^4$ comprises at least one coordinating atom that forms a dative bond with In; and each $R^5$ is independently hydrogen, optionally substituted linear or branched $C_{1-18}$ alkyl, optionally substituted cyclic $C_{3-18}$ alkyl or, when there is a C—N double bond, absent.

2. The complex of claim 1, having a structure of formula (Ib):

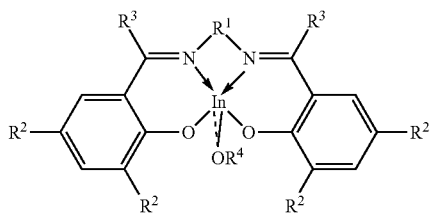

wherein,
the dashed line represents a dative bond between a coordinating atom in $R^4$ and In;

$R^4$ is bonded to O, and is an optionally substituted aminoalkyl or aminoaryl, optionally substituted thioalkyl or thioaryl, optionally substituted phosphinoalkyl or phosphinoaryl, or optionally substituted ether radical, which forms a dative bond with In via the respective heteroatom; or, $R^4$ is bonded to O, and has the structure of formula (Ic)

(Ic)

[structure of formula (Ic)]

wherein
n is 0 to 8;

each Z is independently absent, at least one lone pair of electrons, or a hydrogen, halogen, hydroxide, optionally substituted linear or branched $C_{1-18}$ alkyl, optionally substituted cyclic $C_{3-18}$ alkyl, optionally substituted phenyl or $SiR'$, where $R'$ is alkyl or aryl, optionally substituted heteroaryl, optionally substituted $C_{1-18}$ amino, $C_{1-18}$ alkyl alkoxide; or, any two Z, together with the atoms to which they are attached, combine to form a cycle or heterocycle;

X is absent, optionally substituted linear or branched $C_{1-8}$ alkyl, optionally substituted cyclic $C_{3-8}$ alkyl, optionally substituted aryl, or optionally substituted heteroaryl; and each Y is independently C or a coordinating atom, wherein at least two Y are C, and at least one Y coordinates to In.

3. The complex of claim 1 wherein $R^1$ is

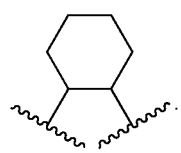 [SMILES: *C1CCCCC1*]

4. The complex of claim 1, wherein at least one $R^2$ is a halogen, an optionally substituted $C_{1-5}$ alkyl, an optionally substituted aryl, an optionally substituted $C_3$-$C_{12}$ cyclic alkyl, or $Si(aryl)_3$; $R^3$ is H and $R^4$ is $C_{1-3}$ heteroaryl-substituted alkylene; or, each $R^2$ is H, or $C_{1-5}$ alkyl, $R^3$ is H, and $R^4$ is $C_{1-3}$ heteroaryl-substituted alkylene.

5. The complex of claim 1 wherein $R^1$ is chiral and enantiomerically enriched, or wherein $R^1$ is chiral and racemic, or wherein $R^1$ is achiral.

6. The complex of claim 5, wherein the stereochemistry of $R^1$ is (R,R).

7. The complex of claim 1 having the structure
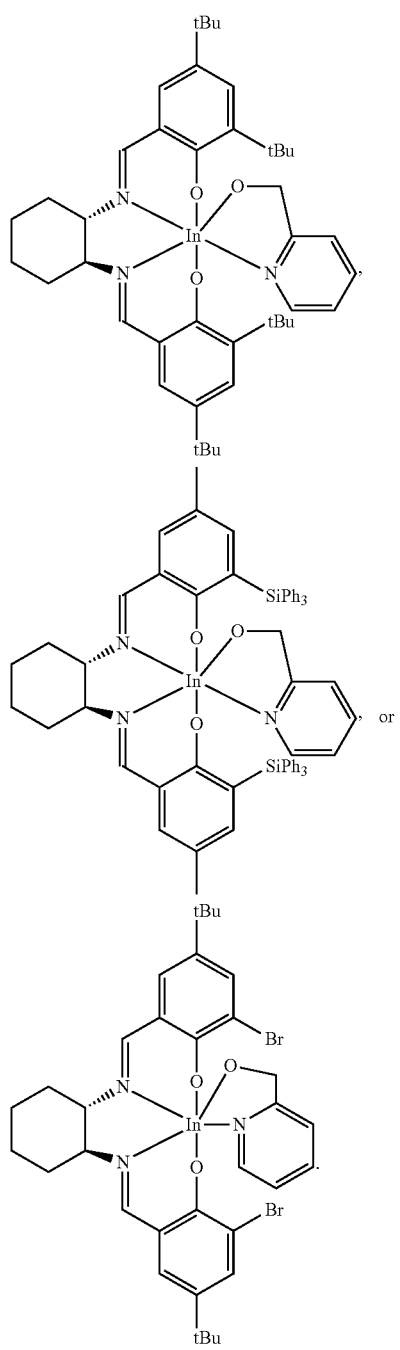
8. The complex of claim 1, comprising a ligand that is:
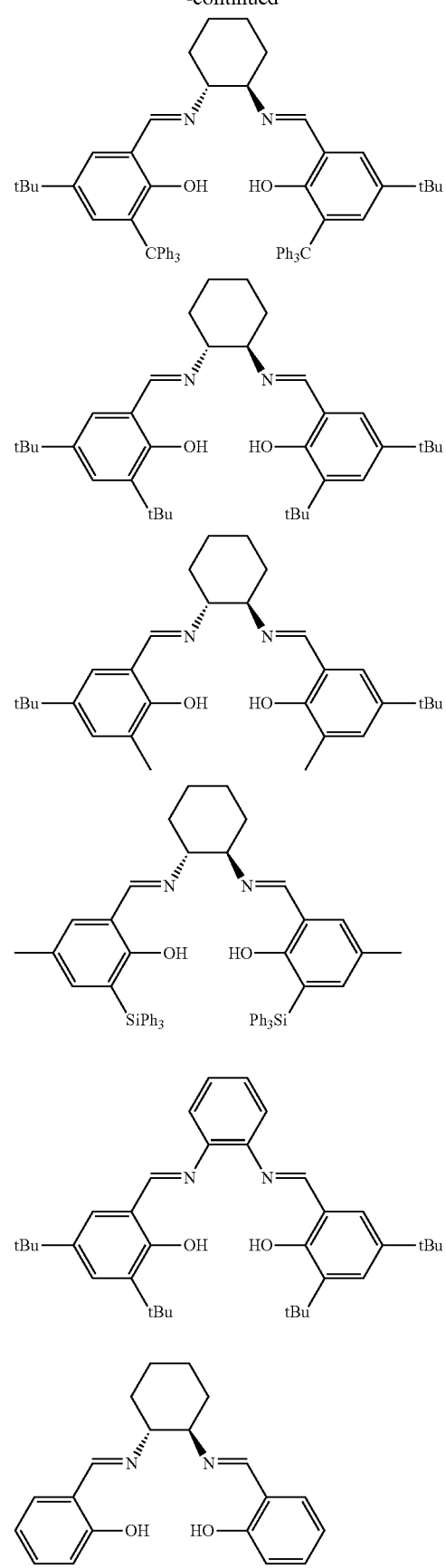

-continued

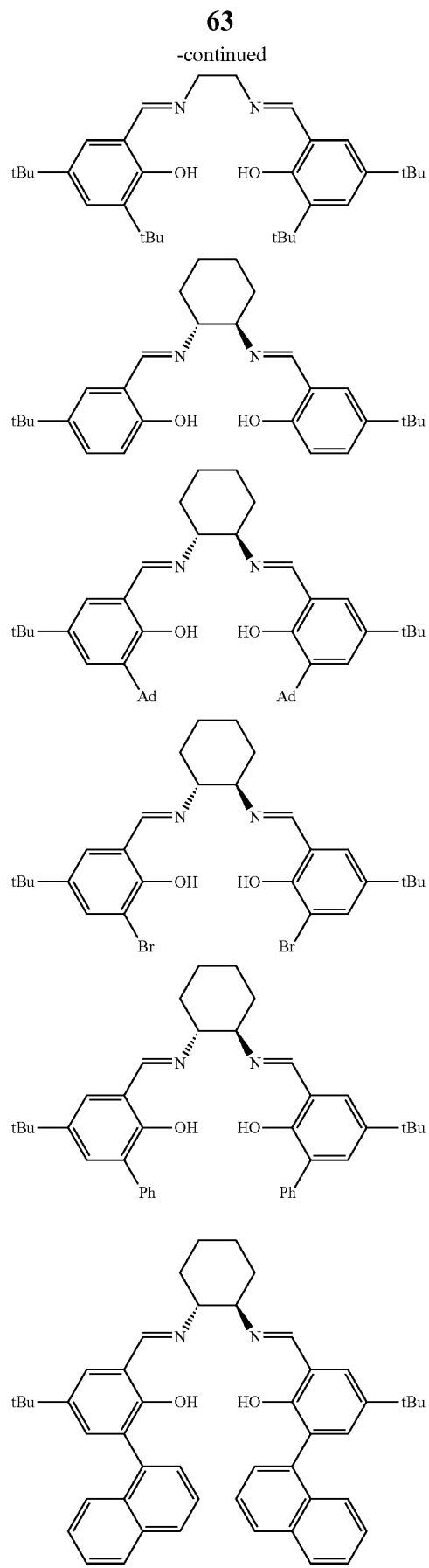

-continued

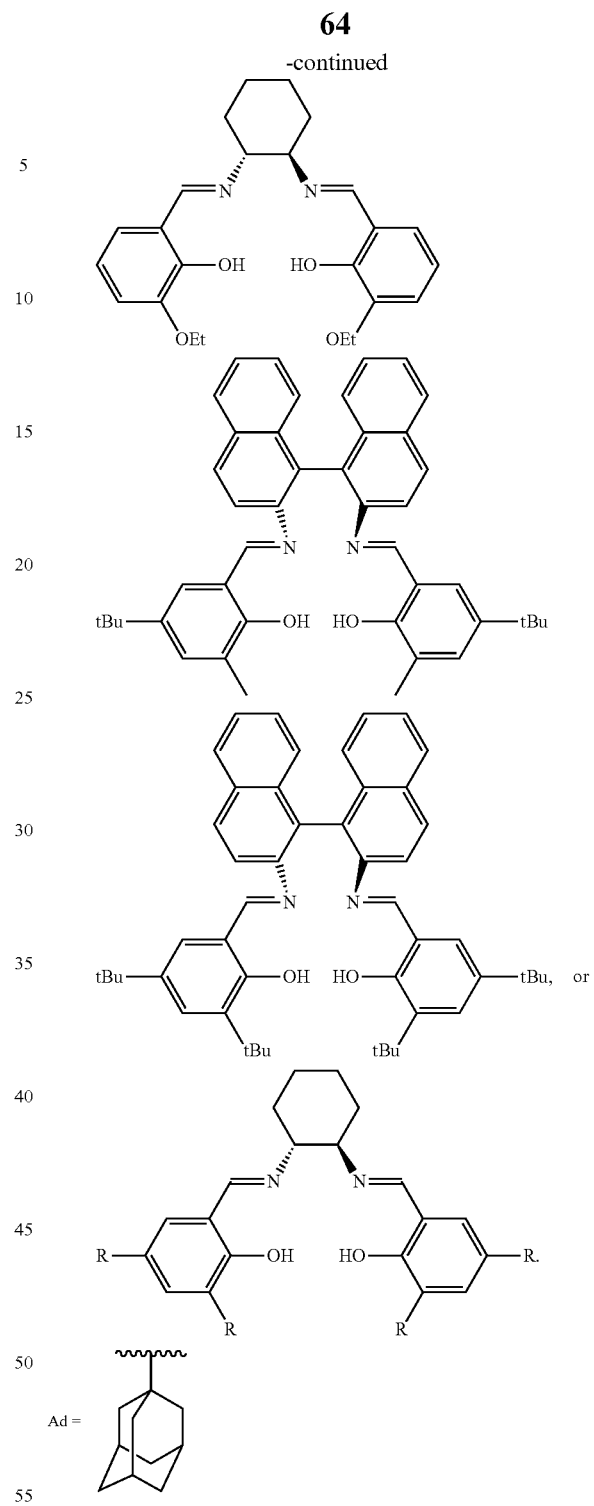

9. A method of ring-opening polymerization comprising polymerizing a cyclic ester monomer, or combination of two or more cyclic ester monomers, in the presence of a complex of claim 1, under conditions suitable for ring-opening polymerization.

10. The method of claim 9, wherein the presence of the complex provides a short, or negligible, initiation period for polymerization.

11. The method of claim 9, wherein when a combination of two or more cyclic ester monomers are polymerized, the different monomers are polymerized simultaneously or sequentially.

12. The method of claim 9, wherein the cyclic ester monomer is a lactide and the polymerization product is a polylactic acid.

13. The method of claim 12, further comprising one or more of the following characteristics:
   (a) wherein the lactide is L-lactide, D-lactide, meso-lactide, rac-lactide, a non-equal mixture of L and D lactides, or a mixture of L, D, and meso-lactides;
   (b) wherein the polylactic acid is isotactically enriched;
   (c) wherein the polylactic acid is isotactically enriched and the isotactic enrichment is between about 0.6 and about 1.0, or between about 0.7 and about 1.0;
   (d) wherein the polylactic acid has a polydispersity index of less than about 2.0, or less than about 1.7, or less than about 1.5; and
   (e) wherein the polylactic acid has a molecular weight of greater than about 300, or greater than about 10,000, or from about 300 to about 10,000,000, or from about 10,000 to about 1,000,000, or from about 20,000 to about 150,000, or from about 28,800 to about 144,000.

14. The method of claim 9, wherein the polymerization is performed in the absence of solvent.

15. The method of claim 9, wherein the polymerization is an immortal polymerization.

16. The method of claim 9, wherein the product is a copolymer.

17. The method of claim 16, wherein the product is a random copolymer or a block copolymer.

18. A method for preparing a block copolymer, comprising:
   (a) polymerizing a first cyclic ester monomer using a first complex of claim 1 under conditions suitable for ring-opening polymerization of the first cyclic ester monomer to form a first polymer block of the block copolymer; and
   (b) polymerizing a second cyclic ester monomer, different from the first cyclic ester monomer, a second complex of claim 1 under conditions suitable for ring-opening polymerization of the second cyclic ester monomer to form a second polymer block of the block copolymer.

19. The method of claim 18, wherein the first cyclic ester monomer is lactide, D-lactide, L-lactide, meso-lactide, rac-lactide, a non-equal mixture of L and D lactides, a mixture of L, D, and meso-lactides, β-butyrolactone, or 4-(but-3-en-1-yl)oxetan-2-one; and the second cyclic ester monomer is, lactide, D-lactide, L-lactide, meso-lactide, rac-lactide, a non-equal mixture of L and D lactides, a mixture of L, D, and meso-lactides, β-butyrolactone, or 4-(but-3-en-1-yl)oxetan-2-one.

20. The method of claim 18, additionally comprising the step of
   (c) polymerizing a third cyclic ester monomer, different from the first and second cyclic ester monomer, with a third complex of claim 1 under conditions suitable for ring-opening polymerization of the third cyclic ester monomer to form a third polymer block of the block copolymer; and wherein the third complex for step (c) is the same as the first and second complexes used in steps (a) and/or (b).

21. The method of claim 20, wherein the third cyclic ester monomer is lactide, D-lactide, L-lactide, meso-lactide, rac-lactide, a non-equal mixture of L and D lactides, a mixture of L, D, and meso-lactides, β-butyrolactone, or 4-(but-3-en-1-yl)oxetan-2-one.

22. A method of producing a complex having the structure of formula (Ia):

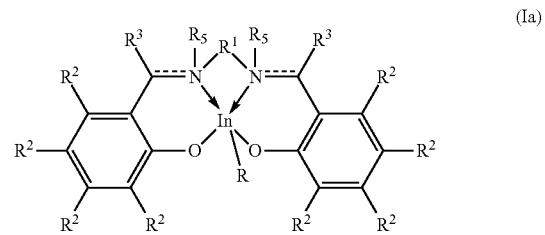

wherein
the dashed line represents an optional double bond;
$R^1$ is an optionally substituted $C_{2-5}$ alkylene,

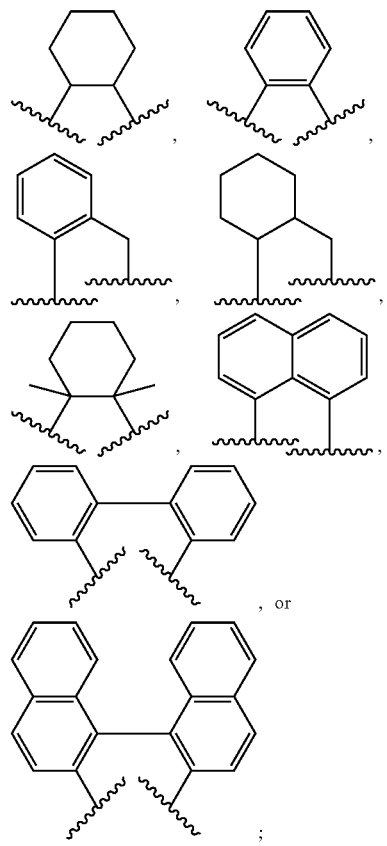

each $R^2$ is independently hydrogen, halogen, optionally substituted linear or branched $C_{1-18}$ alkyl, optionally substituted cyclic $C_{3-18}$ alkyl, optionally substituted phenyl or SiR', where R' is alkyl or aryl;

each $R^3$ is hydrogen or optionally substituted linear or branched $C_{1-18}$ alkyl, optionally substituted cyclic $C_{3-18}$ alkyl;

R is a coordinating alkoxide of formula $OR^4$, wherein $R^4$ comprises at least one coordinating atom that forms a dative bond with In; and each $R^5$ is independently hydrogen, optionally substituted linear or branched $C_{1-18}$ alkyl, optionally substituted cyclic $C_{3-18}$ alkyl or, when there is a C—N double bond, absent, comprising:

reacting a compound of formula (IIa) with a strong base to give a diphenoxide

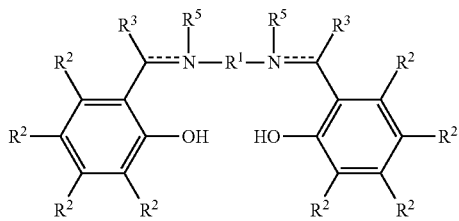

IIa complexing the diphenoxide of step a) with an indium salt $InX_3$ to give an indium complex of formula (IIb),

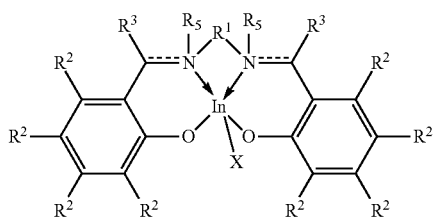

IIb wherein X is an anion, and reacting the indium complex of formula (IIb) with a salt of $R^4OM$ wherein: M is a metal cation or $NR^6_4{}^+$, wherein $R^6$ is an alkyl; and, $R^4$ is as defined above.

23. The method of claim 22 wherein the acceptable anion is fluorine, chlorine, bromine, iodine, triflate or an alkoxide.

24. A method of producing a complex having the structure of formula (Ia):

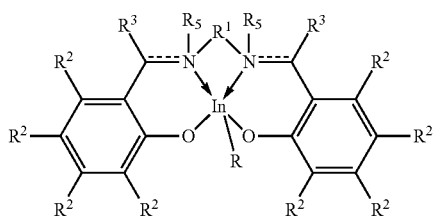

(Ia)

wherein the dashed line represents an optional double bond;

$R^1$ is an optionally substituted $C_{2-5}$ alkylene,

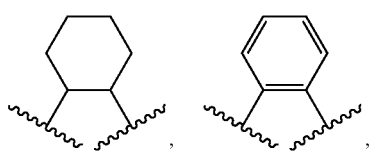

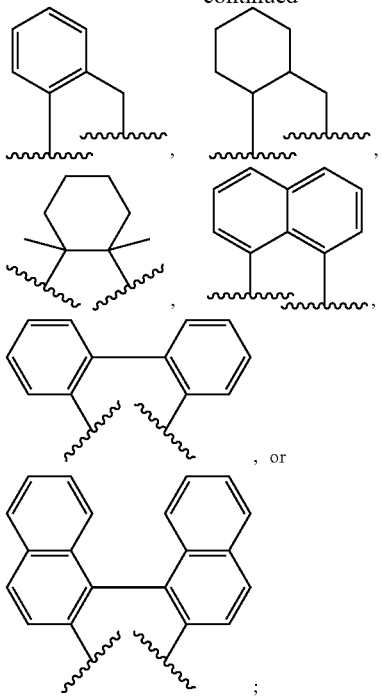

each $R^2$ is independently hydrogen, halogen, optionally substituted linear or branched $C_{1-18}$ alkyl, optionally substituted cyclic $C_{3-18}$ alkyl, optionally substituted phenyl or SiR', where R' is alkyl or aryl;

each $R^3$ is hydrogen or optionally substituted linear or branched $C_{1-18}$ alkyl, optionally substituted cyclic $C_{3-18}$ alkyl;

R is a coordinating alkoxide of formula $OR^4$, wherein $R^4$ comprises at least one coordinating atom that forms a dative bond with In; and each $R^5$ is independently hydrogen, optionally substituted linear or branched $C_{1-18}$ alkyl, optionally substituted cyclic $C_{3-18}$ alkyl or, when there is a C—N double bond, absent, comprising:

reacting a compound of formula (IIa)

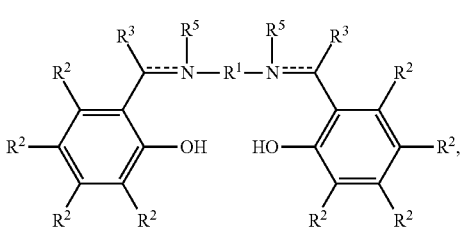

IIa wherein $R^2$, $R^3$, and $R^5$ are as defined above, with an indium salt $InX_3$; and a salt of $R^4OM$ wherein M is a metal cation or $NR^6_4{}^+$, wherein $R^6$ is an alkyl, and $R^4$ is as defined above.

25. The method of claim 24, wherein the synthesis is a one-pot synthesis of a complex having the structure of formula (Ia).

26. The complex of claim 1 wherein each $R^2$ is independently hydrogen, halogen, optionally substituted linear or branched $C_{1-10}$ alkyl, optionally substituted cyclic $C_{3-18}$ alkyl, or optionally substituted phenyl or SiR', where R' is alkyl or aryl.

27. The complex of claim 1 wherein each $R^2$ is independently hydrogen, halogen, optionally substituted linear or branched $C_{1-18}$ alkyl, optionally substituted cyclic $C_{3-12}$ alkyl, or optionally substituted phenyl or SiR', where R' is alkyl or aryl.

28. The complex of claim 1 wherein each $R^3$ is hydrogen or optionally substituted linear or branched $C_{1-10}$ alkyl, or optionally substituted cyclic $C_{3-18}$ alkyl.

29. The complex of claim 1 wherein each $R^3$ is hydrogen or optionally substituted linear or branched $C_{1-18}$ alkyl, or optionally substituted cyclic $C_{3-12}$ alkyl.

30. The complex of claim 1 wherein each $R^5$ is independently hydrogen, optionally substituted linear or branched $C_{1-10}$ alkyl, optionally substituted cyclic $C_{3-18}$ alkyl or, when there is a C—N double bond, absent.

31. The complex of claim 1 wherein each $R^5$ is independently hydrogen, optionally substituted linear or branched $C_{1-18}$ alkyl, optionally substituted cyclic $C_{3-12}$ alkyl or, when there is a C—N double bond, absent.

32. The complex of claim 2 wherein each Z is independently absent, at least one lone pair of electrons, or a hydrogen, halogen, hydroxide, optionally substituted linear or branched $C_{1-10}$ alkyl, optionally substituted cyclic $C_{3-18}$ alkyl, optionally substituted phenyl or SiR', where R' is alkyl or aryl, optionally substituted heteroaryl, optionally substituted $C_{1-18}$ amino, $C_{1-18}$ alkyl alkoxide; or, any two Z, together with the atoms to which they are attached, combine to form a cycle or heterocycle.

33. The complex of claim 2 wherein each Z is independently absent, at least one lone pair of electrons, or a hydrogen, halogen, hydroxide, optionally substituted linear or branched $C_{1-18}$ alkyl, optionally substituted cyclic $C_{3-12}$ alkyl, optionally substituted phenyl or SiR', where R' is alkyl or aryl, optionally substituted heteroaryl, optionally substituted $C_{1-18}$ amino, $C_{1-18}$ alkyl alkoxide; or, any two Z, together with the atoms to which they are attached, combine to form a cycle or heterocycle.

34. The method of claim 22 wherein each $R^2$ is independently hydrogen, halogen, optionally substituted linear or branched $C_{1-10}$ alkyl, optionally substituted cyclic $C_{3-18}$ alkyl, optionally substituted phenyl or SiR', where R' is alkyl or aryl.

35. The method of claim 22 wherein each $R^2$ is independently hydrogen, halogen, optionally substituted linear or branched $C_{1-18}$ alkyl, optionally substituted cyclic $C_{3-12}$ alkyl, optionally substituted phenyl or SiR', where R' is alkyl or aryl.

36. The method of claim 22 wherein each $R^3$ is hydrogen or optionally substituted linear or branched $C_{1-10}$ alkyl, optionally substituted cyclic $C_{3-18}$.

37. The method of claim 22 wherein each $R^3$ is hydrogen or optionally substituted linear or branched $C_{1-18}$ alkyl, optionally substituted cyclic $C_{3-12}$ alkyl.

38. The method of claim 22 wherein each $R^5$ is independently hydrogen, optionally substituted linear or branched $C_{1-10}$ alkyl, optionally substituted cyclic $C_{3-18}$ alkyl or, when there is a C—N double bond, absent.

39. The method of claim 22 wherein each $R^5$ is independently hydrogen, optionally substituted linear or branched $C_{1-18}$ alkyl, optionally substituted cyclic $C_{3-12}$ alkyl or, when there is a C—N double bond, absent.

40. The method of claim 22 wherein the metal cation comprises $Li^+$, $Na^+$ or $K^+$.

41. The method of claim 24 wherein each $R^2$ is independently hydrogen, halogen, optionally substituted linear or branched $C_{1-10}$ alkyl, optionally substituted cyclic $C_{3-18}$ alkyl, optionally substituted phenyl or SiR', where R' is alkyl or aryl.

42. The method of claim 24 wherein each $R^2$ is independently hydrogen, halogen, optionally substituted linear or branched $C_{1-18}$ alkyl, optionally substituted cyclic $C_{3-12}$ alkyl, optionally substituted phenyl or SiR', where R' is alkyl or aryl.

43. The method of claim 24 wherein each $R^3$ is hydrogen or optionally substituted linear or branched $C_{1-10}$ alkyl, optionally substituted cyclic $C_{3-18}$ alkyl.

44. The method of claim 24 wherein each $R^3$ is hydrogen or optionally substituted linear or branched $C_{1-18}$ alkyl optionally substituted cyclic $C_{3-12}$ alkyl.

45. The method of claim 24 wherein each $R^5$ is independently hydrogen, optionally substituted linear or branched $C_{1-10}$ alkyl, optionally substituted cyclic $C_{3-18}$ alkyl or, when there is a C—N double bond, absent.

46. The method of claim 24 wherein each $R^5$ is independently hydrogen, optionally substituted linear or branched $C_{1-18}$ alkyl, optionally substituted cyclic $C_{3-12}$ alkyl or, when there is a C—N double bond, absent.

47. The method of claim 24 wherein the metal cation comprises $Li^+$, $Na^+$ or $K^+$.

* * * * *